United States Patent [19]
Sung et al.

[11] Patent Number: 5,866,408
[45] Date of Patent: Feb. 2, 1999

[54] MODIFICATION OF XYLANASE TO IMPROVE THERMOPHILICITY, ALKOPHILICITY AND THERMOSTABILITY

[75] Inventors: Wing L. Sung, Gloucester; Makoto Yaguchi, Ottawa, both of Canada; Kazuhiko Ishikawa, Tsukuba, Japan

[73] Assignee: National Research Council of Canada, Ottawa, Canada

[21] Appl. No.: 47,370

[22] Filed: Mar. 25, 1998

Related U.S. Application Data

[62] Division of Ser. No. 709,912, Sep. 9, 1996, Pat. No. 5,759,840.

[51] Int. Cl.$^6$ .................................. C12N 9/24; D21C 3/00
[52] U.S. Cl. ............................................. 435/278; 435/200
[58] Field of Search ...................................... 435/200, 278

[56] References Cited

U.S. PATENT DOCUMENTS

| | | | |
|---|---|---|---|
| 5,306,633 | 4/1994 | Gottschalk et al. | 435/200 |
| 5,405,769 | 4/1995 | Campbell et al. | 435/200 |
| 5,759,840 | 6/1998 | Sung et al. | 435/200 |

FOREIGN PATENT DOCUMENTS

| | | |
|---|---|---|
| 0 473 545 A2 | 4/1992 | European Pat. Off. . |
| WO 94/24270 | 10/1994 | WIPO . |
| WO 95/12668 | 5/1995 | WIPO . |

OTHER PUBLICATIONS

Arase, A., Yomo, T., Urabe, I., Hata, Y., Katsube, Y. and Okada, H. (1993) *FEBS Lett.* 316:123–127.
Fontes, C.M.G.A., Hazelwood, G.P., Morag, E., Hall, J., Hirst, B.H., and Gilbert, H.J. (1995) *Biochem. J.* 307:151–158.
Gilkes, et al (1991). *Microbiol. Review* 55:303–315.
Irwin, D., Jung, E. D. and Wilson, D. B. (1994) *Appl. Environ. Microbiol.* 60:763–770.
Lever, M. (1972) *Analytical Biochemistry* 47:273–279.
Lüthi, E., Jasmat, N. B., and Bergquist, P. L. (1990) *Appl. Environ. Microbiol.* 56:2677–2683.
Mathrani, I.M. and Ahring, B.K. (1992) *Appl. Microbiol. Biotechnol.* 38:23–27.
Nissen, A.M., Anker, L., Munk, N., Lange, N.K. in *Xylans and Xylanases*, edited by J. Visser, G. Beldman, M.A. Kustrers–van–Someran, and A.G.J. Voragen, published by Elsevier, Amsterdam, 1992, pp. 325–337.
Sakka, K., Kojima Y., Kondo, T., Karita, S., Ohomiya, K. Shimada, K. (1993) *Biosci. Biotech. Biochem.* 57:273–277.
Simpson, H. D., Haufler, U. R., and Daniel, R. M. (1991) *Biochem. J.* (1991) 277:413–417.
Sung. W. L.. Yao. F.–L., Zahab, D. M. and Narang, S. A. (1986) *Proc. Natl. Acad. Sci. USA* 83:561–565.
Sung, W. L., Luk, C. K., Zahab, D. M. and Wakarchuk, W. (1993) *Protein Expression Purif.* 4:200–206.
Sung, W. L., Luk, C. K., Chan, B., Wakarchuk, W., Yaguchi, M., Campbell, R., Willick, G., Ishikawa, K. and Zahab, D. M. (1995) *Biochem. Cell. Biol.* 73:253–259.
Tolan et al (1995) *Pulp and Paper Canada,* 96:107–110, Dec. 1995.
Wakarchuk, W.W., Campbell, R.L., Sung, W.L., Davoodi, J., and Yaguchi, M. (1994) *Protein Science* 3:467–475.
Wakarchuck W. W., Sung, W. L., Campbell, R. L., Cunningham, A., Watson, D. C. and Yaguchi, M. (1994) *Protein Engineering* 7:1379–1386.
Winterhalter C. and Liebl, W. (1995) *Appl. Environ. Bicrobiol.* 61:1810–1815.
Zappe, H., Jones, W. A., and Woods, D. R. (1987) *Appl. Microbiol. Biotechnol.* 27:57–63.
Zappe, H., Jones, W. A., and Woods, D. R. (1990) *Nucleic Acids Res.* 18:2179.
Moreau et al., (1994) *Enzyme Microb. Technol.* 16:420–424.
Gilbert, et al., (1993) *Appl. Microbiol. Biotechnol.,* pp. 508–514.
Oliver, et al., (1985) *A Dictionary of Genetic Engineering,* p. 121.

*Primary Examiner*—Karen Cochrane Carlson
*Assistant Examiner*—Einar Stole
*Attorney, Agent, or Firm*—Fitzpatrick, Cella, Harper & Scinto

[57] ABSTRACT

Producing a xylanase enzyme of superior performance in the bleaching of pulp. More specifically, a modified xylanase of Family 11 that shows improved thermophilicity, alkalophilicity, and thermostability as compared to the natural xylanase. The modified xylanases contain any of three types of modifications: (1) changing amino acids 10, 27, and 29 of *Trichoderma reesei* xylanase II or the corresponding amino acids of another Family 11 xylanase, where these amino acids are changed to histidine, methionine, and leucine, respectively; (2) substitution of amino acids in the N-terminal region with amino acids from another xylanase enzyme. In a preferred embodiment, substitution of the natural *Bacillus circulans* or *Trichoderma reesei* xylanase with a short sequence of amino acids from *Thermomonospora fusca* xylanase yielded chimeric xylanases with higher thermophilicity and alkalophilicity; (3) an extension upstream of the N-terminus of up to 10 amino acids. In a preferred embodiment, extension of the N-terminus of the xylanase with the tripeptide glycine-arginine-arginine improved its performance.

8 Claims, 26 Drawing Sheets

Abbreviations of species

Bp  Bacillus pumilus
Ca  Clostridium acetobutylicum P262 XynB
Cs  Clostridium stercorarium xynA
Rf  Ruminococcus flavefaciens
Tr2 Trichoderma reesei XYN II
Tv  Trichoderma viride
Th  Trichoderma harzianum
Sc  Schizophyllum commune Xylanase A
An  Aspergillus niger, var. awamori
At  Aspergillus tubigensis
Tr1 Trichoderma reesei XYN I
Ss  Streptomyces sp. 36a
S1B Streptomyces lividans Xln B
S1C Streptomyces lividans Xln C
Tf  Thermomonospora fusca TfxA
Bc  Bacillus circulans
Bs  Bacillus subtilis

Aligned amino acid sequences numbering from N-terminus

First section

| Lowest amino acid # | Highest amino acid # |
|---|---|
| Ca  23 | S AFNTQAAP  31 |
| Cs   1 | G  1 |

FIG. 1-1

Second Section

| | Lowest amino acid # | | | Highest amino acid # |
|---|---|---|---|---|---|
| Bp | 1 | RTITNNEMGN | HSGYDYELWK | DYGNT-SMTL | NNGGAFSAGW | N--NIGNA | 45 |
| Ca | 32 | KTITSNEIGV | NGGYDYELWK | DYGNT-SMTL | KNGGAFSCQW | S--NIGNA | 76 |
| Cs | 2 | RIIYDNETGT | HGGYDYELWK | DYGNT-IMEL | NDGGTFSCQW | S--NIGNA | 46 |
| Rf | 1 | SAADQQTRGN | VGGYDYEMWN | QNGQGQASMN | PGAGSFTCSW | S--NIENF | 46 |
| Tr2 | 1 | QTIQPGTGY | NNGYFYSYWN | DGHGGVTYTN | GPGGQFSVNW | S--NSGNF | 45 |
| Tv | 1 | QTIQPGTGF | NNGYFYSYWN | DGHGGVTYTN | GPGGQFSVNW | S--NSGNF | 45 |
| Th | 1 | QTIGPGTGY | SNGYYYSYWN | DGHAGVTYTN | GGGGSFTVNW | S--NSGNF | 45 |
| Sc | 1 | SGTPSSTGT | DGGYYYSWWT | DGAGDATYQN | NGGGSYTLTW | SG-NNGNL | 46 |
| An | 1 | S | AGINYVQNYN | GNLGDFTY-D | ESAGTFSMYW | EDGVSSDF | 37 |
| AT | 1 | S | AGINYVQNYN | QNLGDFTY-D | ESAGTFSMYW | EDGVSSDF | 37 |
| Tr1 | 1 | | ASINYDQNYQ | TGG-QVSYS- | PSNTGFSVNW | N--TQDDF | 34 |
| Ss | 1 | ATTIT-NETGY | D-GMYYSFWT | DGGGSVSMTL | NGGGSYSTRW | T--NCGNF | 45 |
| S1B | 1 | DTVVTTNQEGT | NNGYYYSFWT | DSQGTVSMNM | GSGGQYSTSW | R--NTGNF | 47 |
| S1C | 1 | ATTITTNQTGT | D-GMYYSFWT | DGGGSVSMTL | NGGGSYSTQW | T--NCGNF | 46 |
| Tf | 1 | AVTSNETGY | HDGYFYSFWT | DAPGTVSMEL | GPGGNYSTSW | R--NTGNF | 45 |
| Bc | 1 | | ASTDYWQNWT | DGGGIVNAVN | GSGGNYSVNW | S--NTGNF | 36 |
| Bs | 1 | | ASTDYWQNWT | DGGGIVNAVN | GSGGNYSVNW | S--NTGNF | 36 |

Third section

| | Lowest amino acid # | | | | | Highest amino acid # | |
|---|---|---|---|---|---|---|---|
| Bp | 46 | LFRK-GKKFD | ST-RTHHQLG | NISINYNASF | N-PSGNSYLC | VYGWTQSP | 90 |
| Ca | 77 | LFRK-GKKFN | DT-QTYKQLG | NISVNYNCNY | Q-PYGNSYLC | VYGWTSSP | 121 |
| Cs | 47 | LFRK-GRKFN | SD-KTYQELG | DIVVEYGCDY | N-PNGNSYLC | VYGWTRNF | 91 |
| Rf | 47 | LARM-GKNYD | SQKKNYKAFG | NIVLTYDVEY | T-PRGNSYMC | VYGWTRNP | 92 |
| Tr2 | 46 | VGGK-GWQPG | TKNKV----- | ---INFS-GS | YNPNGNSYLS | VYGWSRNP | 83 |
| Tv | 46 | VGGK-GWQPG | TKNKV----- | ---INFS-GS | YNPNGNSYLS | VYGWSRNP | 83 |
| Th | 46 | VGGK-GWQPG | TKNKV----- | ---INFS-GS | YNPNGNSYLS | IYGWSRNP | 83 |
| Sc | 47 | VGGK-GWNPG | AASRS----- | ---ISYS-GT | YQPNGNSYLS | VYGWTRSS | 84 |
| An | 38 | VVGL-GWTTG | SSNA------ | ---ITYSAEY | SASGSSSYLA | VYGWVNYP | 76 |
| At | 38 | VVGVGGWTTG | SSNA------ | ---ITYSAEY | SASGSASYLA | VYGWVNYP | 76 |
| Trl | 35 | VVGV-GWTTG | SSAP------ | ---INFGGSF | SVNSGTGLLS | VYGWSTNP | 72 |
| Ss | 46 | VAGK-GWANG | GR-RT----- | ---VRYT-GW | FNPSGNGYGC | LYGWTSNP | 82 |
| S1B | 48 | VAGK-GWANG | GR-RT----- | ---VQYS-GS | FNPSGNAYLA | LYGWTSNP | 84 |
| S1C | 47 | VAGK-GWSTG | DGN------- | ---VRYN-GY | FNPVGNGYGC | LYGWTSNP | 82 |
| Tf | 46 | VAGK-GWATG | GR-RT----- | ---VTYS-AS | FNPSGNAYLT | LYGWTRNP | 82 |
| Bc | 37 | VVGK-GWTTG | SPFRT----- | ---INYNAGV | WAPNGNGYLT | LYGWTRSP | 75 |
| Bs | 37 | VVGK-GWTTG | SPFRT----- | ---INYNAGV | WAPNGNGYLT | LYGWTRSP | 75 |

Fourth Section

| | Lowest amino acid # | | | Highest amino acid # | |
|---|---|---|---|---|---|
| Bp | 91 | LAEYYIVDSW | GTYR-PT--G | AYKGSFYADG GTYDIYETTR | VNQPSIIG 135 |
| Ca | 122 | LVEYYVIDSW | GSWRPP--GG | TSKGTITVDG GIYDIYETTR | INQPSIQG 167 |
| Cs | 92 | LVEYYIVESW | GSWRPP--GA | TPKGTITQWMAGTYEIYETTR | VNQPSIDG 138 |
| Rf | 93 | LMEYYIVEGW | GDWRPPGNDG | EVKGTVSANG NTYDIRKTMR | YNQPSLDG 140 |
| Tr2 | 84 | LIEYYIVENF | GTYN-PSTGA | TKLGEVTSDG SVYDIYRTQR | VNQPSIIG 130 |
| Tv | 84 | LIEYYIVENF | GTYN-PSTGA | TKLGEVTSDG SVYDIYRTQR | VNQPSIIG 130 |
| Th | 84 | LIEYYIVENF | GTYN-PSTGA | TKLGEVTSDG SVYDIYRTQR | VNQPSIIG 130 |
| Sc | 85 | LIEYYIVESY | GSYD-PSSAA | SHKGSVTCNG ATYDILSTWR | YNAPSIDG 131 |
| An | 77 | GAEYYIVEDY | GDYN-PCSSA | TSLGTVYSDG STYQVCTDTR | INEPSITG 123 |
| At | 77 | QAEYYIVEDY | GDYN-PCSSA | TSLGTVYSDG STYQVCTDTR | INEPSITG 123 |
| Tr1 | 73 | LVEYYIMEDN | HNY--PAQ-G | TVKGTVTSDG ATYTIWENTR | VNEPSIQG 117 |
| Ss | 83 | LVEYYIVDNW | GSYR-PT--G | ETRGTVTSDG GTYDIYKTTR | YNAPSVEA 127 |
| S1B | 85 | LVEYYIVDNW | GTYR-PT--G | EYKGTVTSDG GTYDIYKTTR | VNKPSVEG 129 |
| S1C | 83 | LVEYYIVDNW | GSYR-PT--G | TYKGTVSSDG GTYDIYQTTR | YNAPSVEG 127 |
| Tf | 83 | LVEYYIVESW | GTYR-PT--G | TYMGTVTTDG GTYDIYKTTR | YNAPSIEG 127 |
| Bc | 76 | LIEYYVVDSW | GTYR-PT--G | TYKGTVKSDG GTYDIYTTTR | YNAPSIDG 120 |
| Bs | 76 | LIEYYVVDSW | GTYR-PT--G | TYKGTVKSDG GTYDIYTTTR | YNAPSIDG 120 |

FIG. 1-4

Fifth Section

| | Lowest amino acid # | | | Highest amino acid # |
|---|---|---|---|---|
| Bp  | 136 | -IATFKQYWS VRQTKRTS-- | ------GTVS | VSAHFRKWES LGMPM-GK 173 |
| Ca  | 168 | -NTTFKQYWS VRRTKRTS-- | ------GTIS | VSKHFAAWES KGMPL-GK 206 |
| Cs  | 139 | -TATFQQYWS VRTSKRTS-- | ------GTIS | VTEHFKQWER MGMRM-GK 177 |
| Rf  | 141 | -TATFPQYWS VRQTSGSANN | QTNYMKGTID | VSKHFDAWSA AGLDMSGT 187 |
| Tr2 | 131 | -TATFYQYWS VRRNHR-S-S | ------GSVN | TANHFNAWAQ QGLTL-GT 168 |
| Tv  | 131 | -TATFYQYWS VRRTHR-S-S | ------GSVN | TANHFNAWAQ QGLTL-GT 168 |
| Th  | 131 | -TATFYQYWS VRRNHR-S-S | ------GSVN | TANHFNAWAS HGLTL-GT 168 |
| Sc  | 132 | -TQTFEQFWS VRNPKKAPGG | SIS----GTVD | VQCHFDAWKG LGMNLGSE 175 |
| An  | 124 | -TSTFTQYFS VRESTRTS-- | ------GTVT | VANHFNFWAQ HGFGN-SD 162 |
| At  | 124 | -TSTFTQYFS VRESTRTS-- | ------GTVT | VANHFNFWAH HGFHN-SD 162 |
| Tr1 | 118 | -TATFNQYIS VRNSPR-T-S | ------GTVT | VQNHFN--WAS LGLHLGQM 155 |
| Ss  | 128 | -PAAFDQYWS VRQSKVT--S | ------GTIT | TGNHFDAWAR AGMMMGNF 166 |
| S1B | 130 | TR-TFDQYWS VRQSKR-TG- | ------GTIT | TGNHFDAWAR AGMPLGNF 168 |
| S1C | 128 | TK-TFQQYWS VRQSKVTSGS | ------GTIT | TGNHFDAWAR AGMMMGQF 168 |
| Tf  | 128 | TR-TFDQYWS VRQSKRTS-- | ------GTIT | AGNHFDAWAR HGMHLGTH 166 |
| Bc  | 121 | DRTTFTQYWS VRQSKRPTGS | N------ATIT | FTNHVNAWKS HGMNLGSN 163 |
| Bs  | 121 | DRTTFTQYWS VRQSKRPTGS | N------ATIT | FSNHVNAWKS HGMNLGSN 163 |

*FIG. 1-5*

Sixth Section

| | Lowest amino acid # | | | Highest amino acid # |
|---|---|---|---|---|
| Bp | 174 | MYETAFTVEG | YQSSGSANVM | TNQLFIGN 201 |
| Ca | 207 | MHETAFNIEG | YQSSGKADVN | SMSINIGK 233 |
| Cs | 178 | MYEVALTVEG | YQSSGYANVY | KNEIRIGANP...... |
| Rf | 188 | LYEVSLNIEG | YRSNGSANVK | SVSV 211 |
| Tr2 | 169 | MDYQIVAVEG | YFSSGSASI- | TVS 190 |
| Tv | 169 | MDYQIVAVEG | YFSSGSASI- | TVS 190 |
| Th | 169 | MDYQIVAVEG | YFSSGSASI- | TVS 190 |
| Sc | 176 | HNYQIVATEG | YQSSGTATI- | TVT 197 |
| An | 163 | FNYQVMAVEA | WSGAGSASV- | TISS 184 |
| At | 163 | FNYQVVAVEA | WSGAGSAAV- | TISS 184 |
| Tr1 | 156 | MNYQVVAVEG | WGGGSASQ- | SVSN 178 |
| Ss | 167 | RYYMINATEG | YQSSGSTI- | TVSG 189 |
| S1B | 169 | SYYMINATEG | YQSSGTSSI- | TVSG...... |
| S1C | 169 | RYYMINATEG | YQSSGSSNI- | NVGG...... |
| Tf | 167 | D-YMIMATEG | YQSSGSSNVT | TVSG 191 |
| Bc | 164 | WAYQVMATEG | YQSSGSSNV- | LGTS...... |
| Bs | 164 | WAYQVMATEG | YQSSGSSNV- | TVW 185 |
|  |  |  |  | TVW 185 |

```
         3   4   5   6   7   8   9   10  11  12  13  14  15  16
     A   S   I   G   P   G   T   G   F   N   N   G   Y   F   Y   S
                                    XyTv-1
    CT  AGC ATA GGA CCA GGA ACC GGT TTC AAC AAC GGT TAC TTT TAC AGC
     G  TAT CCT GGT CCT TGG CCA AAG TTG TTG CCA ATG AAA ATG TCG
        NheI                AgeI              XyTv-8

17  18  19  20  21  22  23  24  25  26  27  28  29  30  31  32
     Y   W   N   D   G   H   G   G   V   T   Y   T   N   G   P   G
                        XyTv-2
    TAT TGG AAC GAT GGC CAT GGT GGT GTT ACC TAT ACA AAC GGG CCC GGA
    ATA ACC TTG CTA CCG GTA CCA CCA CAA TGG ATA TGT TTG CCC GGG CCT
                        NcoI                      XyTv-7    ApaI 33  34  35  36  37  38  39  40  41  42  43  44  45  46  47  48
     G   Q   F   S   V   N   W   S   N   S   G   N   F   V   G   G
    GGC CAA TTT AGC GTC AAT TGG TCT AAC TCC GGA AAC TTC GTA GGT GGA
    CCG GTT AAA TCG CAG TTA ACC AGA TTG AGG CCT TTG AAG CAT CCA CCT
                                MunI        BspEI
```

```
       XyTv-3
49  50  51  52  53  54  55  56  57  58  59  60  61  62  63  64
 K   G   W   Q   P   G   T   K   N   K   V   I   N   F   S   G
AAA GGT TGG CAA CCC GGG ACC AAA AAT AAG GTG ATC AAC TTC TCT GGA
TTT CCA ACC GTT GGG CCC TGG TTT TTA TTC CAC TAG TTG AAG AGA CCT
                        XmaI                         XyTv-6
65  66  67  68  69  70  71  72  73  74  75  76  77  78  79  80
 S   Y   N   P   N   G   N   S   Y   L   S   V   Y   G   W   S
TCT TAT AAT CCG AAT GGG AAT TCA TAC TTA AGC GTC TAT GGC TGG TCT
AGA ATA TTA GGC TTA CCC TTA AGT ATG AAT TCG CAG ATA CCG ACC AGA
        XyTv-5          EcoRI       AflII
81  82  83  84  85  86  87  88  89  90  91  92  93  94  95
 R   N   P   L   I   E   Y   Y   I   V   E   N   F   G   T
AGA AAC CCA CTG ATT GAA TAT TAC ATT GTC GAA AAT TTC GGT AC
TCT TTG GGT GAC TAA CTT ATA ATG TAA CAG CTT TTA AAG C
XbaI                                                KpnI
```

*FIG. 3-2*

```
                                        XyTv-101
       92   93   94   95   96   97   98   99  100  101  102  103  104  105
   V   D    N    F    G    T    Y    N    P    S    T    G    A    T    K    L
TC GAC  AAT  TTC  GGT  ACC  TAC  AAT  CCG  AGT  ACC  GGC  GCC  ACA  AAA  TTA
 G TTA  AAG  CCA  TGG  ATG  TTA  GGC  TCA  TGG  CCG  CGG  TGT  TTT  AAT
   SalI          KpnI                       XyTv-110          KasI/NarI

XyTv-102
      106  107  108  109  110  111  112  113  114  115  116  117  118  119  120  121
   G   E    V    T    S    D    G    S    V    Y    D    I    Y    R    T    Q
GGC GAA  GTC  ACT  AGT  GAT  GGA  TCC  GTA  TAT  GAT  ATC  TAC  CGT  ACC  CAA
CCG CTT  CAG  TGA  TCA  CTA  CCT  AGG  CAT  ATA  CTA  TAG  ATG  GCA  TGG  GTT
                    SpeI              BamHI                              XyTv-109

XyTv-103
      122  123  124  125  126  127  128  129  130  131  132  133  134  135  136  137
   R   V    N    Q    P    S    I    I    G    T    A    T    F    Y    Q    Y
CGC GTT  AAT  CAG  CCA  TCG  ATC  ATT  GGA  ACC  GCC  ACC  TTT  TAT  CAG  TAC
GCG CAA  TTA  GTC  GGT  AGC  TAG  TAA  CCT  TGG  CGG  TGG  AAA  ATA  GTC  ATG
MluI                       ClaI
```

FIG. 3-3

```
138 139 140 141 142 143 144 145 146 147 148 149 150 151 152 153
 W   S   V   R   R   T   H   R   S   S   G   S   V   N   T   A
TGG AGT GTT AGA CGT ACG CAT CGG AGC TCC GGT TCG GTT AAT ACT GCG
ACC TCA CAA TCT GCA TGC GTA GCC TCG AGG CCA AGC CAA TTA TGA CGC
            BsiWI         SacI
XyTv-108
                XyTv-104

154 155 156 157 158 159 160 161 162 163 164 165 166 167 168 169
 N   H   F   N   A   W   A   Q   Q   G   L   T   L   G   T   M
AAT CAC TTT AAT GCA TGG GCA CAG CAA GGG TTA ACC CTA GGT ACA ATG
TTA GTG AAA TTA CGT ACC CGT GTC GTT CCC AAT TGG GAT CCA TGT TAC
         NsiI                         AvrII
                   XyTv-107

XyTv-105
170 171 172 173 174 175 176 177 178 179 180 181 182 183 184 185
 D   Y   Q   I   V   A   V   E   G   Y   F   S   S   G   S   A
GAT TAT CAA ATC GTA GCG GTG GAA GGC TAC TTC TCG AGT GGT TCC GCT
CTA ATA GTT TAG CAT CGC CAC CTT CCG ATG AAG AGC TCA CCA AGG CGA
                                    XhoI
XyTv-106
```

*FIG. 3-4*

```
186 187 188 189 190
 S   I   T   V   S
AGT ATT ACA GTG AGC TAA A     TCT AG
TCA TAA TGT CAC TCG ATT       TCT AG
                              BglII
```

FIG. 3-5

```
       1   2   3   4   5   6   7   8   9  10  11  12  13  14  15  16
       A   S   T   D   Y   W   Q   N   W   T   D   G   G   G   I   V
      GCT AGC ACA GAT TAC TGG CAA AAC TGG ACA GAC GGT GGC GGT ATC GTT
      CGA TCG TGT CTA ATG ACC GTT TTG ACC TGT CTG CCA CCG CCA TAG CAA
          NheI
                     XY-11
                                                   XY-16

17  18  19  20  21  22  23  24  25  26  27  28  29  30  31  32
       N   A   V   N   G   S   G   G   N   Y   S   V   N   W   S   N
      AAT GCC GTG AAC GGC TCC GGA GGC AAC TAC AGC GTG AAT TGG TCT AAT
      TTA CGG CAC TTG CCG AGG CCT CCG TTG ATG TCG CAC TTA ACC AGA TTA
                             BspEI 33  34  35  36  37  38  39  40  41  42  43  44  45  46  47  48
       T   G   N   F   V   V   G   K   G   W   T   T   G   S   P   F
      ACT GGG AAC TTC GTA GTC GGA AAA GGT TGG ACG ACA GGA TCC CCG TTC
      TGA CCC TTG AAG CAT CAG CCT TTT CCA ACC TGC TGT CCT AGG GGC AAG
                     XY-15                               BamHI
                                         XY-12
```

```
49  50  51  52  53  54  55  56  57  58  59  60  61  62  63  64
 R   T   I   N   Y   N   A   G   V   W   A   P   N   G   N   G
CGT ACG ATC AAC TAC AAC GCT GGC GTT TGG GCC CCG AAT GGT AAC GGT
       GCA TGC TAG TTG ATG TTG CGA CCG CAA ACC CGG GGC TTA CCA TTG CCA
        SplI              XY-14a              ApaI        XY-21

65  66  67  68  69  70  71  72  73  74  75  76  77  78  79  80
 Y   L   T   L   Y   G   W   T   R   S   P   L   I   E   Y   Y
TAC CTG ACA CTG TAT GGC TGG ACG CGT TCG CCA CTG ATT GAA TAT TAC
ATG GAC TGT GAC ATA CCG ACC TGC GCA AGC GGT GAC TAA CTT ATA ATG
                          XY-24         MluI          XY-22

81  82  83  84  85  86  87  88  89  90  91  92  93  94  95  96
 V   V   D   S   W   G   T   Y   R   P   T   G   T   Y   K   G
GTT GTC GAC TCT TGG GGA ACG TAC CGT CCG ACT GGA ACC TAC AAA GGC
CAA CAG CTG AGA ACC CCT TGC ATG GCA GGC TGA CCT TGG ATG TTT CCG
        SalI         XY-23
```

```
                                          XY-3
 97  98  99 100 101 102 103 104 105 106 107 108 109 110 111 112
  T   V   K   S   D   G   G   T   Y   D   I   Y   T   T   T   R
ACA GTC AAA AGC GAT GGT ACC TAT GAC ATC TAC ACC ACA AGA
TGT CAG TTT TCG CTA CCA TGG ATA CTG TAG ATG TGG TGT TCT
                        CCA TGG ATA
                          KpnI            XY-6

113 114 115 116 117 118 119 120 121 122 123 124 125 126 127 128
  Y   N   A   P   S   I   D   G   D   R   T   T   F   T   Q   Y
TAC AAC GCA CCT TCC ATC GAT GGC GAT CGG ACC ACC TTT ACT CAG TAT
ATG TTG CGT GGA AGG TAG CTA CCG CTA GCC TGG TGG AAA TGA GTC ATA
                        TAG CTA
                         ClaI 129 130 131 132 133 134 135 136 137 138 139 140 141 142 143 144
  W   S   V   R   Q   S   K   R   P   T   G   S   N   A   T   I
TGG AGT GTT AGA CAA TCT AAG CGG CCG ACT GGT TCG AAC GCC ACC ATT TAA
ACC TCA CAA TCT GTT AGA TTC GCC GGC TGA CCA AGC TTG CGG TGG TAA
                        AAG CGG CCG ACT GGT TCG
                          EagI           BstBI
```

FIG. 4-3

```
       XY-2
145 146 147 148 149 150 151 152 153 154 155 156 157 158 159 160
 T   F   T   N   H   V   N   A   W   K   S   H   G   M   N   L
ACG TTC ACC AAT CAC GTG AAT GCA TGG AAA TCC CAC GGT ATG AAC CTA
TGC AAG TGG TTA GTG CAC TTA CGT ACC TTT AGG GTG CCA TAC TTG GAT
       XY-5                  NsiI                          AvrII 161 162 163 164 165 166 167 168 169 170 171 172 173 174 175 176
 G   S   N   W   A   Y   Q   V   M   A   T   E   G   Y   Q   S
GGT TCT AAT TGG GCT TAT CAA GTA ATG GCG ACC GAA GGC TAC CAG AGC
CCA AGA TTA ACC CGA ATA GTT CAT TAC CGC TGG CTT CCG ATG GTC TCG
                        XY-4b                                SacI

XY-1
177 178 179 180 181 182 183 184 185
 S   G   S   S   N   V   T   V   W
TCT GGT TCT TCC AAC GTT ACA GTG TGG TAA AGA TCT TGA AGC TTGGACGT
AGA CCA AGA AGG TTG CAA TGT CAC ACC ATT TCT AGA ACT TCG AACCC
              XY-4a                      BglII    HindIII  AatII
```

*FIG. 4-4*

SEQUENCE LISTING ( 1 ) GENERAL INFORMATION:

( i i i ) NUMBER OF SEQUENCES: 54

( 2 ) INFORMATION FOR SEQ ID NO:1:

( i ) SEQUENCE CHARACTERISTICS:
        ( A ) LENGTH: 184 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Aspergillus niger, var. awamori ( x ) PUBLICATION INFORMATION:
        ( A ) AUTHORS: Moat Dr, J
            Dr Roga, M
            Dr Verbakel, J
            Stam, H
            Santos da Silva, M J
            Egmond, M R
            Hagemans, M.L. D
            Gorcom, R.F.M.V.
            Hessing, J.G.M.
            Hondel, C.A.M.J
        ( C ) JOURNAL: Xylan and Xylanase
        ( F ) PAGES: 349-360
        ( G ) DATE: 1992

( x i ) SEQUENCE DESCRIPTION: SEQ ID NO:1:

```
Ser  Ala  Gly  Ile  Asn  Tyr  Val  Gln  Asn  Tyr  Asn  Gly  Asn  Leu  Gly  Asp
 1                 5                        10                      15

Phe  Thr  Tyr  Asp  Glu  Ser  Ala  Gly  Thr  Phe  Ser  Met  Tyr  Trp  Glu  Asp
               20                       25                      30

Gly  Val  Ser  Ser  Asp  Phe  Val  Val  Gly  Leu  Gly  Trp  Thr  Thr  Gly  Ser
          35                       40                      45

Ser  Asn  Ala  Ile  Thr  Tyr  Ser  Ala  Glu  Tyr  Ser  Ala  Ser  Gly  Ser  Ser
     50                       55                      60

Ser  Tyr  Leu  Ala  Val  Tyr  Gly  Trp  Val  Asn  Tyr  Pro  Gly  Ala  Glu  Tyr
65                       70                      75                       80

Tyr  Ile  Val  Glu  Asp  Tyr  Gly  Asp  Tyr  Asn  Pro  Cys  Ser  Ser  Ala  Thr
               85                       90                       95

Ser  Leu  Gly  Thr  Val  Tyr  Ser  Asp  Gly  Ser  Thr  Tyr  Gln  Val  Cys  Thr
               100                      105                     110

Asp  Thr  Arg  Ile  Asn  Glu  Pro  Ser  Ile  Thr  Gly  Thr  Ser  Thr  Phe  Thr
               115                      120                     125

Gln  Tyr  Phe  Ser  Val  Arg  Glu  Ser  Thr  Arg  Thr  Ser  Gly  Thr  Val  Thr
          130                      135                     140

Val  Ala  Asn  His  Phe  Asn  Phe  Trp  Ala  Gln  His  Gly  Phe  Gly  Asn  Ser
145                      150                      155                     160

Asp  Phe  Asn  Tyr  Gln  Val  Met  Ala  Val  Glu  Ala  Trp  Ser  Gly  Ala  Gly
                    165                      170                     175

Ser  Ala  Ser  Val  Thr  Ile  Ser  Ser
                    180
```

( 2 ) INFORMATION FOR SEQ ID NO:2:

( i ) SEQUENCE CHARACTERISTICS:
        ( A ) LENGTH: 185 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Aspergillus tubigensis ( x ) PUBLICATION INFORMATION:
        ( A ) AUTHORS: de Graaff, L.H.
                  van der Broeck, H.C.
                  van Ooijan, A.J.J.
                  Visser, J
        ( C ) JOURNAL: Xylan and Xylanase
        ( F ) PAGES: 235-246
        ( G ) DATE: 1992

( x i ) SEQUENCE DESCRIPTION: SEQ ID NO:2:

```
Ser  Ala  Gly  Ile  Asn  Tyr  Val  Gln  Asn  Tyr  Asn  Gln  Asn  Leu  Gly  Asp
  1              5                        10                       15

Phe  Thr  Tyr  Asp  Glu  Ser  Ala  Gly  Thr  Phe  Ser  Met  Tyr  Trp  Glu  Asp
              20                       25                       30

Gly  Val  Ser  Ser  Asp  Phe  Val  Val  Gly  Leu  Gly  Gly  Trp  Thr  Thr  Gly
         35                       40                       45

Ser  Ser  Asn  Ala  Ile  Thr  Tyr  Ser  Ala  Glu  Tyr  Ser  Ala  Ser  Gly  Ser
 50                       55                       60

Ala  Ser  Tyr  Leu  Ala  Val  Tyr  Gly  Trp  Val  Asn  Tyr  Pro  Gln  Ala  Glu
 65                       70                       75                       80

Tyr  Tyr  Ile  Val  Glu  Asp  Tyr  Gly  Asp  Tyr  Asn  Pro  Cys  Ser  Ser  Ala
                   85                       90                       95

Thr  Ser  Leu  Gly  Thr  Val  Tyr  Ser  Asp  Gly  Ser  Thr  Tyr  Gln  Val  Cys
              100                      105                      110

Thr  Asp  Thr  Arg  Ile  Asn  Glu  Pro  Ser  Ile  Thr  Gly  Thr  Ser  Thr  Phe
              115                      120                      125

Thr  Gln  Tyr  Phe  Ser  Val  Arg  Glu  Ser  Thr  Arg  Thr  Ser  Gly  Thr  Val
         130                      135                      140

Thr  Val  Ala  Asn  His  Phe  Asn  Phe  Trp  Ala  His  His  Gly  Phe  His  Asn
145                      150                      155                      160

Ser  Asp  Phe  Asn  Tyr  Gln  Val  Val  Ala  Val  Glu  Ala  Trp  Ser  Gly  Ala
                   165                      170                      175

Gly  Ser  Ala  Ala  Val  Thr  Ile  Ser  Ser
              180                      185
```

( 2 ) INFORMATION FOR SEQ ID NO:3:

( i ) SEQUENCE CHARACTERISTICS:
        ( A ) LENGTH: 185 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO -continued (iv) ANTI-SENSE: NO (v) FRAGMENT TYPE: internal (vi) ORIGINAL SOURCE:
   (A) ORGANISM: Bacillus circulans (x) PUBLICATION INFORMATION:
   (A) AUTHORS: Yang, R.C.A.
       MacKenzie, C.R.
       Narang, S.A.
   (C) JOURNAL: Nucleic Acid Research
   (D) VOLUME: 16
   (F) PAGES: 7187
   (G) DATE: 1988

(xi) SEQUENCE DESCRIPTION: SEQ ID NO:3:

| Ala | Ser | Thr | Asp | Tyr | Trp | Gln | Asn | Trp | Thr | Asp | Gly | Gly | Gly | Ile | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asn | Ala | Val | Asn | Gly | Ser | Gly | Gly | Asn | Tyr | Ser | Val | Asn | Trp | Ser | Asn |
|     |     |     | 20  |     |     |     |     | 25  |     |     |     |     | 30  |     |     |

| Thr | Gly | Asn | Phe | Val | Val | Gly | Lys | Gly | Trp | Thr | Thr | Gly | Ser | Pro | Phe |
|     |     | 35  |     |     |     |     | 40  |     |     |     |     | 45  |     |     |     |

| Arg | Thr | Ile | Asn | Tyr | Asn | Ala | Gly | Val | Trp | Ala | Pro | Asn | Gly | Asn | Gly |
|     | 50  |     |     |     |     | 55  |     |     |     |     | 60  |     |     |     |     |

| Tyr | Leu | Thr | Leu | Tyr | Gly | Trp | Thr | Arg | Ser | Pro | Leu | Ile | Glu | Tyr | Tyr |
| 65  |     |     |     |     | 70  |     |     |     |     | 75  |     |     |     |     | 80  |

| Val | Val | Asp | Ser | Trp | Gly | Thr | Tyr | Arg | Pro | Thr | Gly | Thr | Tyr | Lys | Gly |
|     |     |     |     | 85  |     |     |     |     | 90  |     |     |     |     | 95  |     |

| Thr | Val | Lys | Ser | Asp | Gly | Gly | Thr | Tyr | Asp | Ile | Tyr | Thr | Thr | Thr | Arg |
|     |     |     | 100 |     |     |     |     | 105 |     |     |     |     | 110 |     |     |

| Tyr | Asn | Ala | Pro | Ser | Ile | Asp | Gly | Asp | Arg | Thr | Thr | Phe | Thr | Gln | Tyr |
|     |     | 115 |     |     |     |     | 120 |     |     |     |     | 125 |     |     |     |

| Trp | Ser | Val | Arg | Gln | Ser | Lys | Arg | Pro | Thr | Gly | Ser | Asn | Ala | Thr | Ile |
|     | 130 |     |     |     |     | 135 |     |     |     |     | 140 |     |     |     |     |

| Thr | Phe | Thr | Asn | His | Val | Asn | Ala | Trp | Lys | Ser | His | Gly | Met | Asn | Leu |
| 145 |     |     |     |     | 150 |     |     |     |     | 155 |     |     |     |     | 160 |

| Gly | Ser | Asn | Trp | Ala | Tyr | Gln | Val | Met | Ala | Thr | Glu | Gly | Tyr | Gln | Ser |
|     |     |     |     | 165 |     |     |     |     | 170 |     |     |     |     | 175 |     |

| Ser | Gly | Ser | Ser | Asn | Val | Thr | Val | Trp |
|     |     |     | 180 |     |     |     |     | 185 |

(2) INFORMATION FOR SEQ ID NO:4:

(i) SEQUENCE CHARACTERISTICS:
   (A) LENGTH: 201 amino acids
   (B) TYPE: amino acid
   (C) STRANDEDNESS: single
   (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
   (A) ORGANISM: Bacillus pumilus (x) PUBLICATION INFORMATION:
   (A) AUTHORS: Fukusaki, E
       Panbangred, W
       Shinmyo, A
       Okada, H
   (C) JOURNAL: FEBS Letters (D) VOLUME: 171
(F) PAGES: 197-201
(G) DATE: 1984

(xi) SEQUENCE DESCRIPTION: SEQ ID NO:4:

| Arg | Thr | Ile | Thr | Asn | Asn | Glu | Met | Gly | Asn | His | Ser | Gly | Tyr | Asp | Tyr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Glu | Leu | Trp | Lys | Asp | Tyr | Gly | Asn | Thr | Ser | Met | Thr | Leu | Asn | Asn | Gly |
|     |     |     | 20  |     |     |     |     | 25  |     |     |     |     |     | 30  |     |
| Gly | Ala | Phe | Ser | Ala | Gly | Trp | Asn | Asn | Ile | Gly | Asn | Ala | Leu | Phe | Arg |
|     |     | 35  |     |     |     |     | 40  |     |     |     |     | 45  |     |     |     |
| Lys | Gly | Lys | Lys | Phe | Asp | Ser | Thr | Arg | Thr | His | His | Gln | Leu | Gly | Asn |
|     | 50  |     |     |     |     | 55  |     |     |     |     | 60  |     |     |     |     |
| Ile | Ser | Ile | Asn | Tyr | Asn | Ala | Ser | Phe | Asn | Pro | Ser | Gly | Asn | Ser | Tyr |
| 65  |     |     |     |     | 70  |     |     |     |     | 75  |     |     |     |     | 80  |
| Leu | Cys | Val | Tyr | Gly | Trp | Thr | Gln | Ser | Pro | Leu | Ala | Glu | Tyr | Tyr | Ile |
|     |     |     |     | 85  |     |     |     |     | 90  |     |     |     |     | 95  |     |
| Val | Asp | Ser | Trp | Gly | Thr | Tyr | Arg | Pro | Thr | Gly | Ala | Tyr | Lys | Gly | Ser |
|     |     |     | 100 |     |     |     |     | 105 |     |     |     |     | 110 |     |     |
| Phe | Tyr | Ala | Asp | Gly | Gly | Thr | Tyr | Asp | Ile | Tyr | Glu | Thr | Thr | Arg | Val |
|     |     | 115 |     |     |     |     | 120 |     |     |     |     | 125 |     |     |     |
| Asn | Gln | Pro | Ser | Ile | Ile | Gly | Ile | Ala | Thr | Phe | Lys | Gln | Tyr | Trp | Ser |
|     | 130 |     |     |     |     | 135 |     |     |     |     | 140 |     |     |     |     |
| Val | Arg | Gln | Thr | Lys | Arg | Thr | Ser | Gly | Thr | Val | Ser | Val | Ser | Ala | His |
| 145 |     |     |     |     | 150 |     |     |     |     | 155 |     |     |     |     | 160 |
| Phe | Arg | Lys | Trp | Glu | Ser | Leu | Gly | Met | Pro | Met | Gly | Lys | Met | Tyr | Glu |
|     |     |     |     | 165 |     |     |     |     | 170 |     |     |     |     | 175 |     |
| Thr | Ala | Phe | Thr | Val | Glu | Gly | Tyr | Gln | Ser | Ser | Gly | Ser | Ala | Asn | Val |
|     |     |     | 180 |     |     |     |     | 185 |     |     |     |     | 190 |     |     |
| Met | Thr | Asn | Gln | Leu | Phe | Ile | Gly | Asn |     |     |     |     |     |     |     |
|     |     | 195 |     |     |     |     | 200 |     |     |     |     |     |     |     |     |

(2) INFORMATION FOR SEQ ID NO:5:

(i) SEQUENCE CHARACTERISTICS:
        (A) LENGTH: 185 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
        (A) ORGANISM: Bacillus subtilus (x) PUBLICATION INFORMATION:
        (A) AUTHORS: Parce, M.G.
                Bourbonnais, R
                Desrochers, M
                Jurasek, L
                Yaguchi, M
        (C) JOURNAL: Arch. Microbiol.
        (D) VOLUME: 144
        (F) PAGES: 201-206
        (G) DATE: 1986

(xi) SEQUENCE DESCRIPTION: SEQ ID NO:5:

| Ala | Ser | Thr | Asp | Tyr | Trp | Gln | Asn | Trp | Thr | Asp | Gly | Gly | Gly | Ile | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

```
Asn  Ala  Val  Asn  Gly  Ser  Gly  Gly  Asn  Tyr  Ser  Val  Asn  Trp  Ser  Asn
               20                      25                      30

Thr  Gly  Asn  Phe  Val  Val  Gly  Lys  Gly  Trp  Thr  Thr  Gly  Ser  Pro  Phe
          35                      40                      45

Arg  Thr  Ile  Asn  Tyr  Asn  Ala  Gly  Val  Trp  Ala  Pro  Asn  Gly  Asn  Gly
     50                      55                      60

Tyr  Leu  Thr  Leu  Tyr  Gly  Trp  Thr  Arg  Ser  Pro  Leu  Ile  Glu  Tyr  Tyr
65                       70                      75                           80

Val  Val  Asp  Ser  Trp  Gly  Thr  Tyr  Arg  Pro  Thr  Gly  Thr  Tyr  Lys  Gly
               85                      90                           95

Thr  Val  Lys  Ser  Asp  Gly  Gly  Thr  Tyr  Asp  Ile  Tyr  Thr  Thr  Thr  Arg
               100                     105                     110

Tyr  Asn  Ala  Pro  Ser  Ile  Asp  Gly  Asp  Arg  Thr  Thr  Phe  Thr  Gln  Tyr
          115                     120                     125

Trp  Ser  Val  Arg  Gln  Ser  Lys  Arg  Pro  Thr  Gly  Ser  Asn  Ala  Thr  Ile
     130                     135                     140

Thr  Phe  Ser  Asn  His  Val  Asn  Ala  Trp  Lys  Ser  His  Gly  Met  Asn  Leu
145                      150                     155                          160

Gly  Ser  Asn  Trp  Ala  Tyr  Gln  Val  Met  Ala  Thr  Glu  Gly  Tyr  Gln  Ser
               165                     170                          175

Ser  Gly  Ser  Ser  Asn  Val  Thr  Val  Trp
               180                     185
```

(2) INFORMATION FOR SEQ ID NO:6:

(i) SEQUENCE CHARACTERISTICS:
        (A) LENGTH: 211 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
        (A) ORGANISM: Clostridium acetobutylicum P262
        (B) STRAIN: Xyn B (x) PUBLICATION INFORMATION:
        (A) AUTHORS: Zappe, H
                Jones, W. A.
                Woods, D. R.
        (C) JOURNAL: Nucleic Acids Res.
        (D) VOLUME: 18
        (F) PAGES: 2719
        (G) DATE: 1990

(xi) SEQUENCE DESCRIPTION: SEQ ID NO:6:

```
Ser  Ala  Phe  Asn  Thr  Gln  Ala  Ala  Pro  Lys  Thr  Ile  Thr  Ser  Asn  Glu
1                        5                       10                      15

Ile  Gly  Val  Asn  Gly  Gly  Tyr  Asp  Tyr  Glu  Leu  Trp  Lys  Asp  Tyr  Gly
               20                      25                      30

Asn  Thr  Ser  Met  Thr  Leu  Lys  Asn  Gly  Gly  Ala  Phe  Ser  Cys  Gln  Trp
          35                      40                      45

Ser  Asn  Ile  Gly  Asn  Ala  Leu  Phe  Arg  Lys  Gly  Lys  Lys  Phe  Asn  Asp
     50                      55                      60

Thr  Gln  Thr  Tyr  Lys  Gln  Leu  Gly  Asn  Ile  Ser  Val  Asn  Tyr  Asn  Cys
65                       70                      75                           80
```

```
Asn Tyr Gln Pro Tyr Gly Asn Ser Tyr Leu Cys Val Tyr Gly Trp Thr
                85                  90                      95

Ser Ser Pro Leu Val Glu Tyr Tyr Ile Val Asp Ser Trp Gly Ser Trp
            100                 105                 110

Arg Pro Pro Gly Gly Thr Ser Lys Gly Thr Ile Thr Val Asp Gly Gly
        115                 120                 125

Ile Tyr Asp Ile Tyr Glu Thr Thr Arg Ile Asn Gln Pro Ser Ile Gln
    130                 135                 140

Gly Asn Thr Thr Phe Lys Gln Tyr Trp Ser Val Arg Arg Thr Lys Arg
145                 150                 155                 160

Thr Ser Gly Thr Ile Ser Val Ser Lys His Phe Ala Ala Trp Glu Ser
            165                 170                 175

Lys Gly Met Pro Leu Gly Lys Met His Glu Thr Ala Phe Asn Ile Glu
            180                 185                 190

Gly Tyr Gln Ser Ser Gly Lys Ala Asp Val Asn Ser Met Ser Ile Asn
            195                 200                 205

Ile Gly Lys
210
```

(2) INFORMATION FOR SEQ ID NO:7:

(i) SEQUENCE CHARACTERISTICS:
        (A) LENGTH: 206 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
        (A) ORGANISM: Clostridium stercorarium
        (B) STRAIN: Xyn A (x) PUBLICATION INFORMATION:
        (A) AUTHORS: Sakka, K
            Kojima, Y
            Kondo, T
            Karita, S
            Ohmiya, K
            Shimada, K
        (C) JOURNAL: Biosci, Biotech, Biochem
        (D) VOLUME: 57
        (F) PAGES: 273-277
        (G) DATE: 1993

(xi) SEQUENCE DESCRIPTION: SEQ ID NO:7:

```
Gly Arg Ile Ile Tyr Asp Asn Glu Thr Gly Thr His Gly Gly Tyr Asp
1               5                   10                  15

Tyr Glu Leu Trp Lys Asp Tyr Gly Asn Thr Ile Met Glu Leu Asn Asp
            20                  25                  30

Gly Gly Thr Phe Ser Cys Gln Trp Ser Asn Ile Gly Asn Ala Leu Phe
            35                  40                  45

Arg Lys Gly Arg Lys Phe Asn Ser Asp Lys Thr Tyr Gln Glu Leu Gly
        50                  55                  60

Asp Ile Val Val Glu Tyr Gly Cys Asp Tyr Asn Pro Asn Gly Asn Ser
65                  70                  75                  80

Tyr Leu Cys Val Tyr Gly Trp Thr Arg Asn Phe Leu Val Glu Tyr Tyr
                85                  90                  95
```

| Ile | Val | Glu | Ser | Trp | Gly | Ser | Trp | Arg | Pro | Pro | Gly | Ala | Thr | Pro | Lys |
|---|---|---|---|---|---|---|---|---|---|---|---|---|---|---|---|
| | | | 100 | | | | | 105 | | | | | 110 | | |

| Gly | Thr | Ile | Thr | Gln | Trp | Met | Ala | Gly | Thr | Tyr | Glu | Ile | Tyr | Glu | Thr |
|---|---|---|---|---|---|---|---|---|---|---|---|---|---|---|---|
| | | 115 | | | | | 120 | | | | | 125 | | | |

| Thr | Arg | Val | Asn | Gln | Pro | Ser | Ile | Asp | Gly | Thr | Ala | Thr | Phe | Gln | Gln |
|---|---|---|---|---|---|---|---|---|---|---|---|---|---|---|---|
| | 130 | | | | | 135 | | | | | 140 | | | | |

| Tyr | Trp | Ser | Val | Arg | Thr | Ser | Lys | Arg | Thr | Ser | Gly | Thr | Ile | Ser | Val |
|---|---|---|---|---|---|---|---|---|---|---|---|---|---|---|---|
| 145 | | | | | | 150 | | | | | 155 | | | | 160 |

| Thr | Glu | His | Phe | Lys | Gln | Trp | Glu | Arg | Met | Gly | Met | Arg | Met | Gly | Lys |
|---|---|---|---|---|---|---|---|---|---|---|---|---|---|---|---|
| | | | | 165 | | | | | 170 | | | | | 175 | |

| Met | Tyr | Glu | Val | Ala | Leu | Thr | Val | Glu | Gly | Tyr | Gln | Ser | Ser | Gly | Tyr |
|---|---|---|---|---|---|---|---|---|---|---|---|---|---|---|---|
| | | | 180 | | | | | 185 | | | | | 190 | | |

| Ala | Asn | Val | Tyr | Lys | Asn | Glu | Ile | Arg | Ile | Gly | Ala | Asn | Pro | | |
|---|---|---|---|---|---|---|---|---|---|---|---|---|---|---|---|
| | | 195 | | | | | 200 | | | | | 205 | | | |

( 2 ) INFORMATION FOR SEQ ID NO:8:

( i ) SEQUENCE CHARACTERISTICS:
        ( A ) LENGTH: 211 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Ruminococcus flavefaciens ( x ) PUBLICATION INFORMATION:
        ( A ) AUTHORS: Zhang, J
                Flint, H. J.
        ( C ) JOURNAL: EMBL database accession number Z11127
        ( G ) DATE: 1992

( x i ) SEQUENCE DESCRIPTION: SEQ ID NO:8:

| Ser | Ala | Ala | Asp | Gln | Gln | Thr | Arg | Gly | Asn | Val | Gly | Gly | Tyr | Asp | Tyr |
|---|---|---|---|---|---|---|---|---|---|---|---|---|---|---|---|
| 1 | | | | 5 | | | | | 10 | | | | | 15 | |

| Glu | Met | Trp | Asn | Gln | Asn | Gly | Gln | Gly | Gln | Ala | Ser | Met | Asn | Pro | Gly |
|---|---|---|---|---|---|---|---|---|---|---|---|---|---|---|---|
| | | | 20 | | | | | 25 | | | | | 30 | | |

| Ala | Gly | Ser | Phe | Thr | Cys | Ser | Trp | Ser | Asn | Ile | Glu | Asn | Phe | Leu | Ala |
|---|---|---|---|---|---|---|---|---|---|---|---|---|---|---|---|
| | | 35 | | | | | 40 | | | | | 45 | | | |

| Arg | Met | Gly | Lys | Asn | Tyr | Asp | Ser | Gln | Lys | Lys | Asn | Tyr | Lys | Ala | Phe |
|---|---|---|---|---|---|---|---|---|---|---|---|---|---|---|---|
| | 50 | | | | | 55 | | | | | 60 | | | | |

| Gly | Asn | Ile | Val | Leu | Thr | Tyr | Asp | Val | Glu | Tyr | Thr | Pro | Arg | Gly | Asn |
|---|---|---|---|---|---|---|---|---|---|---|---|---|---|---|---|
| 65 | | | | | 70 | | | | | 75 | | | | | 80 |

| Ser | Tyr | Met | Cys | Val | Tyr | Gly | Trp | Thr | Arg | Asn | Pro | Leu | Met | Glu | Tyr |
|---|---|---|---|---|---|---|---|---|---|---|---|---|---|---|---|
| | | | | 85 | | | | | 90 | | | | | 95 | |

| Tyr | Ile | Val | Glu | Gly | Trp | Gly | Asp | Trp | Arg | Pro | Pro | Gly | Asn | Asp | Gly |
|---|---|---|---|---|---|---|---|---|---|---|---|---|---|---|---|
| | | | 100 | | | | | 105 | | | | | 110 | | |

| Glu | Val | Lys | Gly | Thr | Val | Ser | Ala | Asn | Gly | Asn | Thr | Tyr | Asp | Ile | Arg |
|---|---|---|---|---|---|---|---|---|---|---|---|---|---|---|---|
| | | | 115 | | | | | 120 | | | | | 125 | | |

| Lys | Thr | Met | Arg | Tyr | Asn | Gln | Pro | Ser | Leu | Asp | Gly | Thr | Ala | Thr | Phe |
|---|---|---|---|---|---|---|---|---|---|---|---|---|---|---|---|
| | 130 | | | | | 135 | | | | | 140 | | | | |

| Pro | Gln | Tyr | Trp | Ser | Val | Arg | Gln | Thr | Ser | Gly | Ser | Ala | Asn | Asn | Gln |
|---|---|---|---|---|---|---|---|---|---|---|---|---|---|---|---|
| 145 | | | | | 150 | | | | | 155 | | | | | 160 |

```
            Thr   Asn   Tyr   Met   Lys   Gly   Thr   Ile   Asp   Val   Ser   Lys   His   Phe   Asp   Ala
                              165                     170                           175

Trp   Ser   Ala   Ala   Gly   Leu   Asp   Met   Ser   Gly   Thr   Leu   Tyr   Glu   Val   Ser
                              180                     185                           190

Leu   Asn   Ile   Glu   Gly   Tyr   Arg   Ser   Asn   Gly   Ser   Ala   Asn   Val   Lys   Ser
                              195                     200                           205

Val   Ser   Val
                        210
```

( 2 ) INFORMATION FOR SEQ ID NO:9:

( i ) SEQUENCE CHARACTERISTICS:
        ( A ) LENGTH: 197 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Schizophyllum commune
        ( B ) STRAIN: Xylanase A ( x ) PUBLICATION INFORMATION:
        ( A ) AUTHORS: Oku, T
                 Yaguchi, M
                 Parse, M
                 Jurasek, L
        ( C ) JOURNAL: Canadian Fed. Biol. Soc. annual meeting
        ( F ) PAGES: Abstract #676
        ( G ) DATE: 1988

( x i ) SEQUENCE DESCRIPTION: SEQ ID NO:9:

```
            Ser   Gly   Thr   Pro   Ser   Ser   Thr   Gly   Thr   Asp   Gly   Gly   Tyr   Tyr   Tyr   Ser
            1                       5                       10                          15

Trp   Trp   Thr   Asp   Gly   Ala   Gly   Asp   Ala   Thr   Tyr   Gln   Asn   Asn   Gly   Gly
                              20                      25                          30

Gly   Ser   Tyr   Thr   Leu   Thr   Trp   Ser   Gly   Asn   Asn   Gly   Asn   Leu   Val   Gly
                        35                            40                          45

Gly   Lys   Gly   Trp   Asn   Pro   Gly   Ala   Ala   Ser   Arg   Ser   Ile   Ser   Tyr   Ser
                  50                            55                      60

Gly   Thr   Tyr   Gln   Pro   Asn   Gly   Asn   Ser   Tyr   Leu   Ser   Val   Tyr   Gly   Trp
            65                            70                      75                          80

Thr   Arg   Ser   Ser   Leu   Ile   Glu   Tyr   Tyr   Ile   Val   Glu   Ser   Tyr   Gly   Ser
                              85                            90                          95

Tyr   Asp   Pro   Ser   Ser   Ala   Ala   Ser   His   Lys   Gly   Ser   Val   Thr   Cys   Asn
                              100                           105                         110

Gly   Ala   Thr   Tyr   Asp   Ile   Leu   Ser   Thr   Trp   Arg   Tyr   Asn   Ala   Pro   Ser
                        115                           120                         125

Ile   Asp   Gly   Thr   Gln   Thr   Phe   Glu   Gln   Phe   Trp   Ser   Val   Arg   Asn   Pro
                  130                           135                     140

Lys   Lys   Ala   Pro   Gly   Gly   Ser   Ile   Ser   Gly   Thr   Val   Asp   Val   Gln   Cys
            145                           150                     155                         160

His   Phe   Asp   Ala   Trp   Lys   Gly   Leu   Gly   Met   Asn   Leu   Gly   Ser   Glu   His
                              165                           170                         175

Asn   Tyr   Gln   Ile   Val   Ala   Thr   Glu   Gly   Tyr   Gln   Ser   Ser   Gly   Thr   Ala
                              180                           185                         190
```

```
            Thr   Ile   Thr   Val   Thr
                        195
```

(2) INFORMATION FOR SEQ ID NO:10:

(i) SEQUENCE CHARACTERISTICS:
        (A) LENGTH: 191 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
        (A) ORGANISM: Streptomyces lividans
        (B) STRAIN: Xln B (x) PUBLICATION INFORMATION:
        (A) AUTHORS: Shareck, F
                  Roy, C
                  Yaguchi, M
                  Morosoli, R
                  Kluepfel, D
        (C) JOURNAL: Gene
        (D) VOLUME: 107
        (F) PAGES: 75-82
        (G) DATE: 1991

(xi) SEQUENCE DESCRIPTION: SEQ ID NO:10:

```
Asp   Thr   Val   Val   Thr   Thr   Asn   Gln   Glu   Gly   Thr   Asn   Asn   Gly   Tyr   Tyr
 1                       5                         10                              15

Tyr   Ser   Phe   Trp   Thr   Asp   Ser   Gln   Gly   Thr   Val   Ser   Met   Asn   Met   Gly
                  20                        25                        30

Ser   Gly   Gly   Gln   Tyr   Ser   Thr   Ser   Trp   Arg   Asn   Thr   Gly   Asn   Phe   Val
            35                        40                              45

Ala   Gly   Lys   Gly   Trp   Ala   Asn   Gly   Gly   Arg   Arg   Thr   Val   Gln   Tyr   Ser
            50                        55                        60

Gly   Ser   Phe   Asn   Pro   Ser   Gly   Asn   Ala   Tyr   Leu   Ala   Leu   Tyr   Gly   Trp
 65                         70                         75                              80

Thr   Ser   Asn   Pro   Leu   Val   Glu   Tyr   Tyr   Ile   Val   Asp   Asn   Trp   Gly   Thr
                        85                         90                              95

Tyr   Arg   Pro   Thr   Gly   Glu   Tyr   Lys   Gly   Thr   Val   Thr   Ser   Asp   Gly   Gly
                  100                       105                       110

Thr   Tyr   Asp   Ile   Tyr   Lys   Thr   Thr   Arg   Val   Asn   Lys   Pro   Ser   Val   Glu
            115                       120                       125

Gly   Thr   Arg   Thr   Phe   Asp   Gln   Tyr   Trp   Ser   Val   Arg   Gln   Ser   Lys   Arg
      130                       135                       140

Thr   Gly   Gly   Thr   Ile   Thr   Thr   Gly   Asn   His   Phe   Asp   Ala   Trp   Ala   Arg
145                         150                       155                             160

Ala   Gly   Met   Pro   Leu   Gly   Asn   Phe   Ser   Tyr   Tyr   Met   Ile   Asn   Ala   Thr
                        165                       170                             175

Glu   Gly   Tyr   Gln   Ser   Ser   Gly   Thr   Ser   Ser   Ile   Asn   Val   Gly   Gly
                  180                       185                       190
```

(2) INFORMATION FOR SEQ ID NO:11:

(i) SEQUENCE CHARACTERISTICS:
        (A) LENGTH: 191 amino acids
        (B) TYPE: amino acid
        (C) STRANDEDNESS: single (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
  (A) ORGANISM: Streptomyces lividans
  (B) STRAIN: Xln C (x) PUBLICATION INFORMATION:
  (A) AUTHORS: Shareck, F
    Roy, C
    Yaguchi, M
    Morosoli, R
    Kluepfel, D
  (C) JOURNAL: Gene
  (D) VOLUME: 107
  (F) PAGES: 75-82
  (G) DATE: 1991

(xi) SEQUENCE DESCRIPTION: SEQ ID NO:11:

```
Ala Thr Thr Ile Thr Thr Asn Gln Thr Gly Thr Asp Gly Met Tyr Tyr
 1           5                   10                  15

Ser Phe Trp Thr Asp Gly Gly Gly Ser Val Ser Met Thr Leu Asn Gly
             20                  25                  30

Gly Gly Ser Tyr Ser Thr Gln Trp Thr Asn Cys Gly Asn Phe Val Ala
         35                  40                  45

Gly Lys Gly Trp Ser Thr Gly Asp Gly Asn Val Arg Tyr Asn Gly Tyr
     50                  55                  60

Phe Asn Pro Val Gly Asn Gly Tyr Gly Cys Leu Tyr Gly Trp Thr Ser
 65                  70                  75                  80

Asn Pro Leu Val Glu Tyr Tyr Ile Val Asp Asn Trp Gly Ser Tyr Arg
                 85                  90                  95

Pro Thr Gly Thr Tyr Lys Gly Thr Val Ser Ser Asp Gly Gly Thr Tyr
            100                 105                 110

Asp Ile Tyr Gln Thr Thr Arg Tyr Asn Ala Pro Ser Val Glu Gly Thr
         115                 120                 125

Lys Thr Phe Gln Gln Tyr Trp Ser Val Arg Gln Ser Lys Val Thr Ser
     130                 135                 140

Gly Ser Gly Thr Ile Thr Thr Gly Asn His Phe Asp Ala Trp Ala Arg
145                 150                 155                 160

Ala Gly Met Asn Met Gly Gln Phe Arg Tyr Tyr Met Ile Asn Ala Thr
                 165                 170                 175

Glu Gly Tyr Gln Ser Ser Gly Ser Ser Asn Ile Thr Val Ser Gly
            180                 185                 190
```

(2) INFORMATION FOR SEQ ID NO:12:

(i) SEQUENCE CHARACTERISTICS:
    (A) LENGTH: 189 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTI-SENSE: NO (v) FRAGMENT TYPE: internal (v i) ORIGINAL SOURCE:
     (A) ORGANISM: Streptomyces sp. 36a (x) PUBLICATION INFORMATION:
     (A) AUTHORS: Nagashima, M
               Okumoto, Y
               Okanishi, M
     (C) JOURNAL: Trends in Actinomycetologia
     (F) PAGES: 91-96
     (G) DATE: 1989

(x i) SEQUENCE DESCRIPTION: SEQ ID NO:12:

| Ala | Thr | Thr | Ile | Thr | Asn | Glu | Thr | Gly | Tyr | Asp | Gly | Met | Tyr | Tyr | Ser |
|---|---|---|---|---|---|---|---|---|---|---|---|---|---|---|---|
| 1 | | | | 5 | | | | | 10 | | | | | 15 | |

| Phe | Trp | Thr | Asp | Gly | Gly | Gly | Ser | Val | Ser | Met | Thr | Leu | Asn | Gly | Gly |
|---|---|---|---|---|---|---|---|---|---|---|---|---|---|---|---|
| | | | 20 | | | | | 25 | | | | | 30 | | |

| Gly | Ser | Tyr | Ser | Thr | Arg | Trp | Thr | Asn | Cys | Gly | Asn | Phe | Val | Ala | Gly |
|---|---|---|---|---|---|---|---|---|---|---|---|---|---|---|---|
| | | 35 | | | | | 40 | | | | | 45 | | | |

| Lys | Gly | Trp | Ala | Asn | Gly | Gly | Arg | Arg | Thr | Val | Arg | Tyr | Thr | Gly | Trp |
|---|---|---|---|---|---|---|---|---|---|---|---|---|---|---|---|
| | 50 | | | | | 55 | | | | | 60 | | | | |

| Phe | Asn | Pro | Ser | Gly | Asn | Gly | Tyr | Gly | Cys | Leu | Tyr | Gly | Trp | Thr | Ser |
|---|---|---|---|---|---|---|---|---|---|---|---|---|---|---|---|
| 65 | | | | | 70 | | | | | 75 | | | | | 80 |

| Asn | Pro | Leu | Val | Glu | Tyr | Tyr | Ile | Val | Asp | Asn | Trp | Gly | Ser | Tyr | Arg |
|---|---|---|---|---|---|---|---|---|---|---|---|---|---|---|---|
| | | | | 85 | | | | | 90 | | | | | 95 | |

| Pro | Thr | Gly | Glu | Thr | Arg | Gly | Thr | Val | His | Ser | Asp | Gly | Gly | Thr | Tyr |
|---|---|---|---|---|---|---|---|---|---|---|---|---|---|---|---|
| | | | 100 | | | | | 105 | | | | | 110 | | |

| Asp | Ile | Tyr | Lys | Thr | Thr | Arg | Tyr | Asn | Ala | Pro | Ser | Val | Glu | Ala | Pro |
|---|---|---|---|---|---|---|---|---|---|---|---|---|---|---|---|
| | | | 115 | | | | | 120 | | | | | 125 | | |

| Ala | Ala | Phe | Asp | Gln | Tyr | Trp | Ser | Val | Arg | Gln | Ser | Lys | Val | Thr | Ser |
|---|---|---|---|---|---|---|---|---|---|---|---|---|---|---|---|
| | 130 | | | | | 135 | | | | | 140 | | | | |

| Gly | Thr | Ile | Thr | Thr | Gly | Asn | His | Phe | Asp | Ala | Trp | Ala | Arg | Ala | Gly |
|---|---|---|---|---|---|---|---|---|---|---|---|---|---|---|---|
| 145 | | | | | 150 | | | | | 155 | | | | | 160 |

| Met | Asn | Met | Gly | Asn | Phe | Arg | Tyr | Tyr | Met | Ile | Asn | Ala | Thr | Glu | Gly |
|---|---|---|---|---|---|---|---|---|---|---|---|---|---|---|---|
| | | | | 165 | | | | | 170 | | | | | 175 | |

| Tyr | Gln | Ser | Ser | Gly | Ser | Ser | Thr | Ile | Thr | Val | Ser | Gly | | | |
|---|---|---|---|---|---|---|---|---|---|---|---|---|---|---|---|
| | | | 180 | | | | | 185 | | | | | | | |

(2) INFORMATION FOR SEQ ID NO:13:

(i) SEQUENCE CHARACTERISTICS:
          (A) LENGTH: 189 amino acids
          (B) TYPE: amino acid
          (C) STRANDEDNESS: single
          (D) TOPOLOGY: linear (i i) MOLECULE TYPE: protein (i i i) HYPOTHETICAL: NO (i v) ANTI-SENSE: NO (v) FRAGMENT TYPE: internal (v i) ORIGINAL SOURCE:
          (A) ORGANISM: Thermomonospora fusca
          (B) STRAIN: Tfx A (x) PUBLICATION INFORMATION:
          (A) AUTHORS: Irwin, D
                    Jung, E. D.
                    Wilson, D. B.
          (C) JOURNAL: Appl. Environ. Microbiol.
          (D) VOLUME: 60
          (F) PAGES: 763-770
          (G) DATE: 1994

(x i) SEQUENCE DESCRIPTION: SEQ ID NO:13:

| | | | | | | | | | | | | | | |
|---|---|---|---|---|---|---|---|---|---|---|---|---|---|---|
| Ala 1 | Val | Thr | Ser | Asn 5 | Glu | Thr | Gly | Tyr | His 10 | Asp | Gly | Tyr | Phe | Tyr Ser 15 |
| Phe | Trp | Thr | Asp 20 | Ala | Pro | Gly | Thr | Val 25 | Ser | Met | Glu | Leu | Gly 30 | Pro Gly |
| Gly | Asn | Tyr 35 | Ser | Thr | Ser | Trp | Arg 40 | Asn | Thr | Gly | Asn | Phe 45 | Val | Ala Gly |
| Lys | Gly 50 | Trp | Ala | Thr | Gly | Gly 55 | Arg | Arg | Thr | Val | Thr 60 | Tyr | Ser | Ala Ser |
| Phe 65 | Asn | Pro | Ser | Gly | Asn 70 | Ala | Tyr | Leu | Thr | Leu 75 | Tyr | Gly | Trp | Thr Arg 80 |
| Asn | Pro | Leu | Val | Glu 85 | Tyr | Tyr | Ile | Val | Glu 90 | Ser | Trp | Gly | Thr | Tyr Arg 95 |
| Pro | Thr | Gly | Thr 100 | Tyr | Met | Gly | Thr | Val 105 | Thr | Thr | Asp | Gly | Gly 110 | Thr Tyr |
| Asp | Ile | Tyr 115 | Lys | Thr | Thr | Arg | Tyr 120 | Asn | Ala | Pro | Ser | Ile 125 | Glu | Gly Thr |
| Arg | Thr 130 | Phe | Asp | Gln | Tyr | Trp 135 | Ser | Val | Arg | Gln | Ser 140 | Lys | Arg | Thr Ser |
| Gly 145 | Thr | Ile | Thr | Ala | Gly 150 | Asn | His | Phe | Asp | Ala 155 | Trp | Ala | Arg | His Gly 160 |
| Met | His | Leu | Gly | Thr 165 | His | Asp | Tyr | Met | Ile 170 | Met | Ala | Thr | Glu | Gly Tyr 175 |
| Gln | Ser | Ser | Gly 180 | Ser | Ser | Asn | Val | Thr 185 | Leu | Gly | Thr | Ser | | |

(2) INFORMATION FOR SEQ ID NO:14:

(i) SEQUENCE CHARACTERISTICS:
        (A) LENGTH: 190 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
        (A) ORGANISM: Thricoderma harzianum (x) PUBLICATION INFORMATION:
        (A) AUTHORS: Yaguchi, M
            Roy, C
            Watson, D. C.
            Rollin, F
            Tan, L. U. L.
            Senior, D. J.
            Saddler, J. N.
        (C) JOURNAL: Xylan and Xylanase
        (F) PAGES: 435-438
        (G) DATE: 1992

(xi) SEQUENCE DESCRIPTION: SEQ ID NO:14:

| | | | | | | | | | | | | | | |
|---|---|---|---|---|---|---|---|---|---|---|---|---|---|---|
| Gln 1 | Thr | Ile | Gly | Pro 5 | Gly | Thr | Gly | Tyr | Ser 10 | Asn | Gly | Tyr | Tyr | Tyr Ser 15 |
| Tyr | Trp | Asn | Asp 20 | Gly | His | Ala | Gly | Val 25 | Thr | Tyr | Thr | Asn | Gly 30 | Gly Gly |
| Gly | Ser | Phe 35 | Thr | Val | Asn | Trp | Ser 40 | Asn | Ser | Gly | Asn | Phe 45 | Val | Gly Gly |

```
Lys  Gly  Trp  Gln  Pro  Gly  Thr  Lys  Asn  Lys  Val  Ile  Asn  Phe  Ser  Gly
     50                       55                      60

Ser  Tyr  Asn  Pro  Asn  Gly  Asn  Ser  Tyr  Leu  Ser  Ile  Tyr  Gly  Trp  Ser
65                       70                      75                            80

Arg  Asn  Pro  Leu  Ile  Glu  Tyr  Tyr  Ile  Val  Glu  Asn  Phe  Gly  Thr  Tyr
                    85                       90                           95

Asn  Pro  Ser  Thr  Gly  Ala  Thr  Lys  Leu  Gly  Glu  Val  Thr  Ser  Asp  Gly
               100                      105                     110

Ser  Val  Tyr  Asp  Ile  Tyr  Arg  Thr  Gln  Arg  Val  Asn  Gln  Pro  Ser  Ile
          115                      120                     125

Ile  Gly  Thr  Ala  Thr  Phe  Tyr  Gln  Tyr  Trp  Ser  Val  Arg  Arg  Asn  His
     130                      135                     140

Arg  Ser  Ser  Gly  Ser  Val  Asn  Thr  Ala  Asn  His  Phe  Asn  Ala  Trp  Ala
145                      150                     155                           160

Ser  His  Gly  Leu  Thr  Leu  Gly  Thr  Met  Asp  Tyr  Gln  Ile  Val  Ala  Val
               165                      170                     175

Glu  Gly  Tyr  Phe  Ser  Ser  Gly  Ser  Ala  Ser  Ile  Thr  Val  Ser
               180                      185                     190
```

( 2 ) INFORMATION FOR SEQ ID NO:15:

( i ) SEQUENCE CHARACTERISTICS:
        ( A ) LENGTH: 178 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Trichoderma reesei
        ( B ) STRAIN: Xyn I ( x ) PUBLICATION INFORMATION:
        ( A ) AUTHORS: Torronene, A
                Mach, R. L.
                Messner, R.
                Gonzalez, R.
                Kalkkinen, N
                Harkki, A
                Kubicek, C. P.
        ( C ) JOURNAL: BioTechnology
        ( D ) VOLUME: 10
        ( F ) PAGES: 1461-1465
        ( G ) DATE: 1992

( x i ) SEQUENCE DESCRIPTION: SEQ ID NO:15:

```
Ala  Ser  Ile  Asn  Tyr  Asp  Gln  Asn  Tyr  Gln  Thr  Gly  Gly  Gln  Val  Ser
1                   5                        10                      15

Tyr  Ser  Pro  Ser  Asn  Thr  Gly  Phe  Ser  Val  Asn  Trp  Asn  Thr  Gln  Asp
               20                      25                      30

Asp  Phe  Val  Val  Gly  Val  Gly  Trp  Thr  Thr  Gly  Ser  Ser  Ala  Pro  Ile
          35                      40                      45

Asn  Phe  Gly  Gly  Ser  Phe  Ser  Val  Asn  Ser  Gly  Thr  Gly  Leu  Leu  Ser
     50                       55                      60

Val  Tyr  Gly  Trp  Ser  Thr  Asn  Pro  Leu  Val  Glu  Tyr  Tyr  Ile  Met  Glu
65                       70                      75                            80

Asp  Asn  His  Asn  Tyr  Pro  Ala  Gln  Gly  Thr  Val  Lys  Gly  Thr  Val  Thr
               85                       90                     95
```

| | | | | | | | | | | | | | | |
|---|---|---|---|---|---|---|---|---|---|---|---|---|---|---|
|Ser|Asp|Gly|Ala|Thr|Tyr|Thr|Ile|Trp|Glu|Asn|Thr|Arg|Val|Asn|Glu|
| | | |100| | | |105| | | |110| | | |

Ser Asp Gly Ala Thr Tyr Thr Ile Trp Glu Asn Thr Arg Val Asn Glu
            100                 105                110

Pro Ser Ile Gln Gly Thr Ala Thr Phe Asn Gln Tyr Ile Ser Val Arg
        115             120                 125

Asn Ser Pro Arg Thr Ser Gly Thr Val Thr Val Gln Asn His Phe Asn
    130             135             140

Trp Ala Ser Leu Gly Leu His Leu Gly Gln Met Met Asn Tyr Gln Val
145                 150                 155                 160

Val Ala Val Glu Gly Trp Gly Gly Ser Gly Ser Ala Ser Gln Ser Val
            165             170                 175

Ser Asn ( 2 ) INFORMATION FOR SEQ ID NO:16:

( i ) SEQUENCE CHARACTERISTICS:
        ( A ) LENGTH: 190 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Trichoderma reesei
        ( B ) STRAIN: Xyn II ( x ) PUBLICATION INFORMATION:
        ( A ) AUTHORS: Torronene, A
                Mach, R. L.
                Messner, R
                Gonzalez, R
                Kalkkinen, N
                Harkki, A
                Kubicek, C. P.
        ( C ) JOURNAL: Biotechnology
        ( D ) VOLUME: 10
        ( F ) PAGES: 1461-1465
        ( G ) DATE: 1992

( x i ) SEQUENCE DESCRIPTION: SEQ ID NO:16:

Gln Thr Ile Gln Pro Gly Thr Gly Tyr Asn Asn Gly Tyr Phe Tyr Ser
1               5                   10                  15

Tyr Trp Asn Asp Gly His Gly Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
    50                  55                  60

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
            85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Asn His
    130                 135                 140

```
Arg  Ser  Ser  Gly  Ser  Val  Asn  Thr  Ala  Asn  His  Phe  Asn  Ala  Trp  Ala
145                 150                      155                           160

Gln  Gln  Gly  Leu  Thr  Leu  Gly  Thr  Met  Asp  Tyr  Gln  Ile  Val  Ala  Val
                    165                      170                      175

Glu  Gly  Tyr  Phe  Ser  Ser  Gly  Ser  Ala  Ser  Ile  Thr  Val  Ser
                    180                      185                 190
```

( 2 ) INFORMATION FOR SEQ ID NO:17:

( i ) SEQUENCE CHARACTERISTICS:
        ( A ) LENGTH: 190 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Trichoderma viride ( x ) PUBLICATION INFORMATION:
        ( A ) AUTHORS: Yaguchi, M
                  Roy, C
                  Ujie, M
                  Watson, D. C.
                  Wakarchuk, W.
        ( C ) JOURNAL: Xylan and Xylanase
        ( F ) PAGES: 149-154
        ( G ) DATE: 1992

( x i ) SEQUENCE DESCRIPTION: SEQ ID NO:17:

```
Gln  Thr  Ile  Gln  Pro  Gly  Thr  Gly  Phe  Asn  Asn  Gly  Tyr  Phe  Tyr  Ser
1                   5                        10                      15

Tyr  Trp  Asn  Asp  Gly  His  Gly  Gly  Val  Thr  Tyr  Thr  Asn  Gly  Pro  Gly
               20                        25                      30

Gly  Gln  Phe  Ser  Val  Asn  Trp  Ser  Asn  Ser  Gly  Asn  Phe  Val  Gly  Gly
               35                        40                      45

Lys  Gly  Trp  Gln  Pro  Gly  Thr  Lys  Asn  Lys  Val  Ile  Asn  Phe  Ser  Gly
     50                        55                      60

Ser  Tyr  Asn  Pro  Asn  Gly  Asn  Ser  Tyr  Leu  Ser  Val  Tyr  Gly  Trp  Ser
65                       70                      75                           80

Arg  Asn  Pro  Leu  Ile  Glu  Tyr  Tyr  Ile  Val  Glu  Asn  Phe  Gly  Thr  Tyr
               85                        90                      95

Asn  Pro  Ser  Thr  Gly  Ala  Thr  Lys  Leu  Gly  Glu  Val  Thr  Ser  Asp  Gly
               100                       105                     110

Ser  Val  Tyr  Asp  Ile  Tyr  Arg  Thr  Gln  Arg  Val  Asn  Gln  Pro  Ser  Ile
               115                       120                     125

Ile  Gly  Thr  Ala  Thr  Phe  Tyr  Gln  Tyr  Trp  Ser  Val  Arg  Arg  Thr  His
               130                       135                     140

Arg  Ser  Ser  Gly  Ser  Val  Asn  Thr  Ala  Asn  His  Phe  Asn  Ala  Trp  Ala
145                 150                      155                           160

Gln  Gln  Gly  Leu  Thr  Leu  Gly  Thr  Met  Asp  Tyr  Gln  Ile  Val  Ala  Val
                    165                      170                      175

Glu  Gly  Tyr  Phe  Ser  Ser  Gly  Ser  Ala  Ser  Ile  Thr  Val  Ser
                    180                      185                 190
```

( 2 ) INFORMATION FOR SEQ ID NO:18:

(i) SEQUENCE CHARACTERISTICS:
    (A) LENGTH: 573 base pairs
    (B) TYPE: nucleic acid
    (C) STRANDEDNESS: double
    (D) TOPOLOGY: circular (ii) MOLECULE TYPE: other nucleic acid
    (A) DESCRIPTION: /desc = "Synthetic DNA"

(iii) HYPOTHETICAL: NO (iv) ANTI-SENSE: NO (vii) IMMEDIATE SOURCE:
    (B) CLONE: pTvX(3-190)

(xi) SEQUENCE DESCRIPTION: SEQ ID NO:18:

| | | | | | | |
|---|---|---|---|---|---|---|
| CTAGCATAGG | ACCAGGAACC | GGTTTCAACA | ACGGTTACTT | TTACAGCTAT | TGGAACGATG | 60 |
| GCCATGGTGG | TGTTACCTAT | ACAAACGGGC | CCGGAGGCCA | ATTTAGCGTC | AATTGGTCTA | 120 |
| ACTCCGGAAA | CTTCGTAGGT | GGAAAAGGTT | GGCAACCCGG | GACCAAAAAT | AAGGTGATCA | 180 |
| ACTTCTCTGG | ATCTTATAAT | CCGAATGGGA | ATTCATACTT | AAGCGTCTAT | GGCTGGTCTA | 240 |
| GAAACCCACT | GATTGAATAT | TACATTGTCG | AAAATTTCGG | TACCTACAAT | CCGAGTACCG | 300 |
| GCGCCACAAA | ATTAGGCGAA | GTCACTAGTG | ATGGATCCGT | ATATGATATC | TACCGTACCC | 360 |
| AACGCGTTAA | TCAGCCATCG | ATCATTGGAA | CCGCCACCTT | TTATCAGTAC | TGGAGTGTTA | 420 |
| GACGTACGCA | TCGGAGCTCC | GGTTCGGTTA | ATACTGCGAA | TCACTTTAAT | GCATGGGCAC | 480 |
| AGCAAGGGTT | AACCCTAGGT | ACAATGGATT | ATCAAATCGT | AGCGGTGGAA | GGCTACTTCT | 540 |
| CGAGTGGTTC | CGCTAGTATT | ACAGTGAGCT | AAA | | | 573 |

(2) INFORMATION FOR SEQ ID NO:19:

(i) SEQUENCE CHARACTERISTICS:
    (A) LENGTH: 579 base pairs
    (B) TYPE: nucleic acid
    (C) STRANDEDNESS: double
    (D) TOPOLOGY: circular (ii) MOLECULE TYPE: other nucleic acid
    (A) DESCRIPTION: /desc = "Synthetic DNA"

(iii) HYPOTHETICAL: NO (iv) ANTI-SENSE: NO (vii) IMMEDIATE SOURCE:
    (B) CLONE: pXYbc (viii) POSITION IN GENOME:
    (C) UNITS: bp (xi) SEQUENCE DESCRIPTION: SEQ ID NO:19:

| | | | | | | |
|---|---|---|---|---|---|---|
| GCTAGCACAG | ATTACTGGCA | AAACTGGACA | GACGGTGGCG | GTATCGTTAA | TGCCGTGAAC | 60 |
| GGCTCCGGAG | GCAACTACAG | CGTGAATTGG | TCTAATACTG | GGAACTTCGT | AGTCGGAAAA | 120 |
| GGTTGGACGA | CAGGATCCCC | GTTCCGTACG | ATCAACTACA | ACGCTGGCGT | TTGGGCCCCG | 180 |
| AATGGTAACG | GTTACCTGAC | ACTGTATGGC | TGGACGCGTT | CGCCACTGAT | TGAATATTAC | 240 |
| GTTGTCGACT | CTTGGGGAAC | GTACCGTCCG | ACTGGAACCT | ACAAAGGCAC | AGTCAAAAGC | 300 |
| GATGGTGGTA | CCTATGACAT | CTACACCACC | ACAAGATACA | ACGCACCTTC | CATCGATGGC | 360 |
| GATCGGACCA | CCTTTACTCA | GTATTGGAGT | GTTAGACAAT | CTAAGCGGCC | GACTGGTTCG | 420 |
| AACGCCACCA | TTACGTTCAC | CAATCACGTG | AATGCATGGA | AATCCCACGG | TATGAACCTA | 480 |
| GGTTCTAATT | GGGCTTATCA | AGTAATGGCG | ACCGAAGGCT | ACCAGAGCTC | TGGTTCTTCC | 540 |

AACGTTACAG TGTGGTAAAG ATCTTGAAGC TTGGGACGT 579

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (iv) ANTI-SENSE: NO (vii) IMMEDIATE SOURCE:
        (B) CLONE: TX-162H-1

(xi) SEQUENCE DESCRIPTION: SEQ ID NO:20:

TGGGCACAGC ACGGGTTAAC C 21

(2) INFORMATION FOR SEQ ID NO:21:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (iv) ANTI-SENSE: NO (vii) IMMEDIATE SOURCE:
        (B) CLONE: TX-162H-2

(xi) SEQUENCE DESCRIPTION: SEQ ID NO:21:

CTAGGGTTAA CCCGTGCTGT GCCCATGCA 29

(2) INFORMATION FOR SEQ ID NO:22:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (iv) ANTI-SENSE: NO (vii) IMMEDIATE SOURCE:
        (B) CLONE: Tfx-1

(xi) SEQUENCE DESCRIPTION: SEQ ID NO:22:

CTAGCCACGC GGCCGTAACT TCAAATGAAA CCGGTTATCA TGACGGCTAT TTCTACAGCT 60

TCTGG 65

(2) INFORMATION FOR SEQ ID NO:23:

(i) SEQUENCE CHARACTERISTICS:
        (A) LENGTH: 38 base pairs
        (B) TYPE: nucleic acid (C) STRANDEDNESS: single
(D) TOPOLOGY: linear (ii) MOLECULE TYPE: other nucleic acid
(A) DESCRIPTION: /desc = "Synthetic DNA"

(iii) HYPOTHETICAL: NO (iv) ANTI-SENSE: NO (vii) IMMEDIATE SOURCE:
(B) CLONE: Tfx-2

(xi) SEQUENCE DESCRIPTION: SEQ ID NO:23:

ACCGATGCAC CGGGAACTGT GTCCATGGAG CTCGGGCC  38

(2) INFORMATION FOR SEQ ID NO:24:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Synthetic DNA"

(iii) HYPOTHETICAL: NO (iv) ANTI-SENSE: NO (vii) IMMEDIATE SOURCE:
(B) CLONE: Tfx-3

(xi) SEQUENCE DESCRIPTION: SEQ ID NO:24:

TCATGATAAC CGGTTTCATT TGAAGTTACG GCCGCGTGG  39

(2) INFORMATION FOR SEQ ID NO:25:

(i) SEQUENCE CHARACTERISTICS:
(A) LENGTH: 56 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Synthetic DNA"

(iii) HYPOTHETICAL: NO (iv) ANTI-SENSE: NO (vii) IMMEDIATE SOURCE:
(B) CLONE: Tfx-4

(xi) SEQUENCE DESCRIPTION: SEQ ID NO:25:

CGAGCTCCAT GGACACAGTT CCCGGTGCAT CGGTCCAGAA GCTGTAGAAA TAGCCG  56

(2) INFORMATION FOR SEQ ID NO:26:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Synthetic DNA"

(iii) HYPOTHETICAL: NO (iv) ANTI-SENSE: NO (vii) IMMEDIATE SOURCE:

( B ) CLONE: Tfx(1-6)-1

( x i ) SEQUENCE DESCRIPTION: SEQ ID NO:26:

CTAGCTAAGG AGGCTGCAGA TGGCAGTAAC ATCAAATGAA A    41

( 2 ) INFORMATION FOR SEQ ID NO:27:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i v ) ANTI-SENSE: NO ( v i i ) IMMEDIATE SOURCE:
        ( B ) CLONE: Tfx(1-6)-2

( x i ) SEQUENCE DESCRIPTION: SEQ ID NO:27:

CCGGTTTCAT TTGATGTTAC TGCCATCTGC AGCCTCCTTA G    41

( 2 ) INFORMATION FOR SEQ ID NO:28:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i v ) ANTI-SENSE: NO ( v i i ) IMMEDIATE SOURCE:
        ( B ) CLONE: TX-1f ( x i ) SEQUENCE DESCRIPTION: SEQ ID NO:28:

CTAGCTAAGG AGGCTGCAGA TGCAAACAAT ACAACCAGGA A    41

( 2 ) INFORMATION FOR SEQ ID NO:29:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i v ) ANTI-SENSE: NO ( v i i ) IMMEDIATE SOURCE:
        ( B ) CLONE: TX-8f ( x i ) SEQUENCE DESCRIPTION: SEQ ID NO:29:

CCGGTTCCTG GTTGTATTGT TTGCATCTGC AGCCTCCTTA G    41

( 2 ) INFORMATION FOR SEQ ID NO:30:

( i ) SEQUENCE CHARACTERISTICS:
        ( A ) LENGTH: 29 base pairs (B) TYPE: nucleic acid
(C) STRANDEDNESS: single
(D) TOPOLOGY: linear (ii) MOLECULE TYPE: other nucleic acid
(A) DESCRIPTION: /desc = "Synthetic DNA"

(iii) HYPOTHETICAL: NO (iv) ANTI-SENSE: NO (vii) IMMEDIATE SOURCE:
(B) CLONE: TX-26SMEL-1

(xi) SEQUENCE DESCRIPTION: SEQ ID NO:30:

CATGGTGGTG TGAGCATGGA GCTCGGGCC 29

(2) INFORMATION FOR SEQ ID NO:31:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Synthetic DNA"

(iii) HYPOTHETICAL: NO (iv) ANTI-SENSE: NO (vii) IMMEDIATE SOURCE:
(B) CLONE: TX-28E/29L-1

(xi) SEQUENCE DESCRIPTION: SEQ ID NO:31:

CGAGCTCGTA GGTCACACCA C 21

(2) INFORMATION FOR SEQ ID NO:32:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Synthetic DNA"

(iii) HYPOTHETICAL: NO (iv) ANTI-SENSE: NO (vii) IMMEDIATE SOURCE:
(B) CLONE: TX-27M/29L-1

(xi) SEQUENCE DESCRIPTION: SEQ ID NO:32:

CATGGAGGCG TCACAATGAC TCTGGGGCC 29

(2) INFORMATION FOR SEQ ID NO:33:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Synthetic DNA"

(iii) HYPOTHETICAL: NO (iv) ANTI-SENSE: NO (v i i) IMMEDIATE SOURCE:
                (B) CLONE: TX-27M/29L-2

(x i) SEQUENCE DESCRIPTION: SEQ ID NO:33:

CCAGAGTCAT TGTGACGCCT C                                                                    21

(2) INFORMATION FOR SEQ ID NO:34:

(i) SEQUENCE CHARACTERISTICS:
                (A) LENGTH: 29 base pairs
                (B) TYPE: nucleic acid
                (C) STRANDEDNESS: single
                (D) TOPOLOGY: linear (i i) MOLECULE TYPE: other nucleic acid
                (A) DESCRIPTION: /desc = "Synthetic DNA"

(i i i) HYPOTHETICAL: NO (i v) ANTI-SENSE: NO (v i i) IMMEDIATE SOURCE:
                (B) CLONE: TX-27M-1

(x i) SEQUENCE DESCRIPTION: SEQ ID NO:34:

CATGGAGGCG TCACAATGAC TAATGGGCC                                                             29

(2) INFORMATION FOR SEQ ID NO:35:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (i i) MOLECULE TYPE: other nucleic acid
                (A) DESCRIPTION: /desc = "Synthetic DNA"

(i i i) HYPOTHETICAL: NO (i v) ANTI-SENSE: NO (v i i) IMMEDIATE SOURCE:
                (B) CLONE: TX-27M-2

(x i) SEQUENCE DESCRIPTION: SEQ ID NO:35:

CATTAGTCAT TGTGACGCCT C                                                                    21

(2) INFORMATION FOR SEQ ID NO:36:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (i i) MOLECULE TYPE: other nucleic acid
                (A) DESCRIPTION: /desc = "Synthetic DNA"

(i i i) HYPOTHETICAL: NO (i v) ANTI-SENSE: NO (v i i) IMMEDIATE SOURCE:
                (B) CLONE: Tf-(-1)R-1

(x i) SEQUENCE DESCRIPTION: SEQ ID NO:36:

CTAGCGCAAG AGCAGTAACA AGTAACGAGA                                                            30

(2) INFORMATION FOR SEQ ID NO:37:

(i) SEQUENCE CHARACTERISTICS:

(A) LENGTH: 30 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "Synthetic DNA"

(iii) HYPOTHETICAL: NO (iv) ANTI-SENSE: NO (vii) IMMEDIATE SOURCE:
                (B) CLONE: Tf-(-1)R-2

(xi) SEQUENCE DESCRIPTION: SEQ ID NO:37:

CCGGTCTCGT TACTTGTTAC TGCTCTTGCG                30

(2) INFORMATION FOR SEQ ID NO:38:

(i) SEQUENCE CHARACTERISTICS:
                (A) LENGTH: 47 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "Synthetic DNA"

(iii) HYPOTHETICAL: NO (iv) ANTI-SENSE: NO (vii) IMMEDIATE SOURCE:
                (B) CLONE: CaTf-(-1)R-1

(xi) SEQUENCE DESCRIPTION: SEQ ID NO:38:

CTAGCGCATT CAACACACAG GCCGCTCCTC GAGCTGTCAC CAGCAAC                47

(2) INFORMATION FOR SEQ ID NO:39:

(i) SEQUENCE CHARACTERISTICS:
                (A) LENGTH: 51 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "Synthetic DNA"

(iii) HYPOTHETICAL: NO (iv) ANTI-SENSE: NO (vii) IMMEDIATE SOURCE:
                (B) CLONE: CaTf-(-1)R2

(xi) SEQUENCE DESCRIPTION: SEQ ID NO:39:

CCGGTCTCGT TGCTGGTGAC AGCTCGAGGA GCGGCCTGTG TGTTGAATGC G                51

(2) INFORMATION FOR SEQ ID NO:40:

(i) SEQUENCE CHARACTERISTICS:
                (A) LENGTH: 54 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "Synthetic DNA"

(iii) HYPOTHETICAL: NO (iv) ANTI-SENSE: NO ( v i i ) IMMEDIATE SOURCE:
( B ) CLONE: GRR-Tf(1-6)-1

( x i ) SEQUENCE DESCRIPTION: SEQ ID NO:40:

ACTCTGCAGA TGGGAAGAAG GGCCGTAACT TCAAATGAAA CCGGTTATCA TGAC    54

( 2 ) INFORMATION FOR SEQ ID NO:41:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( i i i ) HYPOTHETICAL: NO ( i v ) ANTI-SENSE: NO ( v i i ) IMMEDIATE SOURCE:
( B ) CLONE: Uni-PCR-1r ( x i ) SEQUENCE DESCRIPTION: SEQ ID NO:41:

GAAAAGTGCC ACCTGACGTC CCAAGCTT    28

( 2 ) INFORMATION FOR SEQ ID NO:42:

( i ) SEQUENCE CHARACTERISTICS:
( A ) LENGTH: 73 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( i i i ) HYPOTHETICAL: NO ( i v ) ANTI-SENSE: NO ( v i i ) IMMEDIATE SOURCE:
( B ) CLONE: TX10HD-2

( x i ) SEQUENCE DESCRIPTION: SEQ ID NO:42:

CCGGTTTCCA CGACGGTTAC TTTTACAGCT ATTGGAACGA CGGCCATGGA GGAGTAACTT    60

ACACCAATGG GCC    73

( 2 ) INFORMATION FOR SEQ ID NO:43:

( i ) SEQUENCE CHARACTERISTICS:
( A ) LENGTH: 65 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( i i i ) HYPOTHETICAL: NO ( i v ) ANTI-SENSE: NO ( v i i ) IMMEDIATE SOURCE:
( B ) CLONE: TX10HD-1

( x i ) SEQUENCE DESCRIPTION: SEQ ID NO:43:

CATTGGTGTA AGTTACTCCT CCATGGCCGT CGTTCCAATA GCTGTAAAAG TAACCGTCGT    60

GGAAA    65

( 2 ) INFORMATION FOR SEQ ID NO:44:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i v ) ANTI-SENSE: NO ( v i i ) IMMEDIATE SOURCE:
        ( B ) CLONE: TX10HD/N-1

( x i ) SEQUENCE DESCRIPTION: SEQ ID NO:44:

```
GAAACCGGTT   ACCACRACGG   TTACTTTTAC   AGCTATTGGA   ACGATGGCC                    49
```

( 2 ) INFORMATION FOR SEQ ID NO:45:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i v ) ANTI-SENSE: NO ( v i i ) IMMEDIATE SOURCE:
        ( B ) CLONE: TrX1f ( x i ) SEQUENCE DESCRIPTION: SEQ ID NO:45:

```
CTAGCTAAGG   AGGCTGCAGA   TGCAAACAAT   ACAACCAGGA   A                            41
```

( 2 ) INFORMATION FOR SEQ ID NO:46:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i v ) ANTI-SENSE: NO ( v i i ) IMMEDIATE SOURCE:
        ( B ) CLONE: TrX8f ( x i ) SEQUENCE DESCRIPTION: SEQ ID NO:46:

```
CCGGTTCCTG   GTTGTATTGT   TTGCATCTGC   AGCCTCCTTA   G                            41
```

( 2 ) INFORMATION FOR SEQ ID NO:47:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid (A) DESCRIPTION: /desc = "Synthetic DNA"

(iii) HYPOTHETICAL: NO (iv) ANTI-SENSE: NO (vii) IMMEDIATE SOURCE:
                    (B) CLONE: Tfx-2b (xi) SEQUENCE DESCRIPTION: SEQ ID NO:47:

ACCGATGCCC CGGGAACTGT GAGTATGGAG CTCGGCC                37

(2) INFORMATION FOR SEQ ID NO:48:

(i) SEQUENCE CHARACTERISTICS:
                    (A) LENGTH: 63 base pairs
                    (B) TYPE: nucleic acid
                    (C) STRANDEDNESS: single
                    (D) TOPOLOGY: linear (ii) MOLECULE TYPE: other nucleic acid
                    (A) DESCRIPTION: /desc = "Synthetic DNA"

(iii) HYPOTHETICAL: NO (iv) ANTI-SENSE: NO (vii) IMMEDIATE SOURCE:
                    (B) CLONE: Tfx-4b (xi) SEQUENCE DESCRIPTION: SEQ ID NO:48:

CCGGGGCCGA GCTCCATACT CACAGTTCCC GGGGCATCGG TCCAGAAGCT GTAGAAATAG        60

CCG        63

(2) INFORMATION FOR SEQ ID NO:49:

(i) SEQUENCE CHARACTERISTICS:
                    (A) LENGTH: 30 base pairs
                    (B) TYPE: nucleic acid
                    (C) STRANDEDNESS: single
                    (D) TOPOLOGY: linear (ii) MOLECULE TYPE: other nucleic acid
                    (A) DESCRIPTION: /desc = "Synthetic DNA"

(iii) HYPOTHETICAL: NO (iv) ANTI-SENSE: NO (vii) IMMEDIATE SOURCE:
                    (B) CLONE: Tf-(-1)K-1

(xi) SEQUENCE DESCRIPTION: SEQ ID NO:49:

CTAGCGCAAA AGCAGTAACA AGTAACGAGA        30

(2) INFORMATION FOR SEQ ID NO:50:

(i) SEQUENCE CHARACTERISTICS:
                    (A) LENGTH: 30 base pairs
                    (B) TYPE: nucleic acid
                    (C) STRANDEDNESS: single
                    (D) TOPOLOGY: linear (ii) MOLECULE TYPE: other nucleic acid
                    (A) DESCRIPTION: /desc = "Synthetic DNA"

(iii) HYPOTHETICAL: NO (iv) ANTI-SENSE: NO (vii) IMMEDIATE SOURCE:
                    (B) CLONE: Tf-(-1)K-2

( x i ) SEQUENCE DESCRIPTION: SEQ ID NO:50:

CCGGTCTCGT TACTTGTTAC TGCTTTTGCG 30

( 2 ) INFORMATION FOR SEQ ID NO:51:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i v ) ANTI-SENSE: NO ( v i i ) IMMEDIATE SOURCE:
        ( B ) CLONE: Tf-(-1)D-1

( x i ) SEQUENCE DESCRIPTION: SEQ ID NO:51:

CTAGCGCAGA TGCAGTAACA AGTAACGAGA 30

( 2 ) INFORMATION FOR SEQ ID NO:52:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i v ) ANTI-SENSE: NO ( v i i ) IMMEDIATE SOURCE:
        ( B ) CLONE: Tf-(-1)E-2

( x i ) SEQUENCE DESCRIPTION: SEQ ID NO:52:

CCGGTCTCGT TACTTGTTAC TGCTTCTGCG 30

( 2 ) INFORMATION FOR SEQ ID NO:53:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i v ) ANTI-SENSE: NO ( v i i ) IMMEDIATE SOURCE:
        ( B ) CLONE: CaTf-PCR-1

( x i ) SEQUENCE DESCRIPTION: SEQ ID NO:53:

CCCGCTAGCG CATTCAACAC ACAAGCARGT SSAAGGGCCG TAACTTCAAA TGAAACCGGT 60

T 61

( 2 ) INFORMATION FOR SEQ ID NO:54:

( i ) SEQUENCE CHARACTERISTICS:
        ( A ) LENGTH: 39 base pairs ( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( i i i ) HYPOTHETICAL: NO ( i v ) ANTI-SENSE: NO ( v i i ) IMMEDIATE SOURCE:
( B ) CLONE: Xy-14a ( x i ) SEQUENCE DESCRIPTION: SEQ ID NO:54:

ATTCGGGGCC CAAACGCCAG CGTTGTAGTT GATCGTACG       3 9

MODIFICATION OF XYLANASE TO IMPROVE THERMOPHILICITY, ALKOPHILICITY AND THERMOSTABILITY

This application is a division of application Ser. No. 08/709,912 filed Sep. 9, 1996, now U.S. Pat. No. 5,759,840.

BACKGROUND OF THE INVENTION

1. Field of the Invention

The field of the invention is the modification of proteins by protein engineering. In particular, the invention concerns modified xylanase enzymes with improved performance at conditions of high temperature and pH. Xylanase enzymes are used to enhance the bleaching of pulp to make white paper. The invention enables xylanase enzymes to be produced with the benefits of enhanced bleaching associated with Family 11 xylanases, but with activity at higher temperature and pH conditions more suitable to the needs of a pulp mill's operation than xylanases currently available.

2. Brief Description of the Prior Art

Xylanase enzymes have been used commercially since 1991 to enhance the bleaching of pulp to make bright white paper. These enzymes are added to the pulp before the pulp is bleached, and remove a portion of the xylan in the pulp. This action allows the subsequent bleaching chemicals, including chlorine, chlorine dioxide, hydrogen peroxide, oxygen, ozone, and sodium hydroxide, to bleach the pulp more efficiently than in the absence of xylanase treatment. The enhanced efficiency of bleaching has allowed mills to reduce the amount of chlorine-based chemicals to use, which decreases the amount of toxic organochlorine compounds in the mill's effluent, as well as produce whiter pulp or allow the mill to save money on its bleaching chemicals. The commercial use of xylanase enzymes for bleaching has been reviewed by Tolan, et al, Pulp and Paper Canada, December 1995.

Xylanase enzymes have been reported from nearly 100 different microbes. The xylanase enzymes are classified into several of the more than 40 families of glycosyl hydrolase enzymes. The glycosyl hydrolase enzymes, which include xylanases, mannanases, amylases, beta-glucanases, cellulases, and other carbohydrases, are classified based on such properties as the sequence of amino acids, the three dimensional structure and the geometry of the catalytic site (Gilkes, et al, (1991) Microbiol. Reviews 55: 303–315).

Of particular interest for pulp bleaching applications are the enzymes classified in Family 11. All of these are xylanases and are known as the "Family 11 xylanases". Some publications refer to these synonymously as the Family G xylanases, but we shall use the term Family 11.

TABLE 1 lists the Family 11 xylanases known at the present time. Most of them are of molecular mass of about 21,000 Da. Three of the Family 11 xylanases- *Clostridium stercorarium* XynA, *Streptomyces lividans* XynB, and *Thermomonospora fusca* XynA-have a higher molecular mass of 31,000 to 50,000 Da. However, these xylanases have a catalytic core sequence of about 21,000 Da similar to the other Family 11 xylanases. The amino acid sequences of the Family 11 xylanases (or, for the larger enzymes, the catalytic core) show a high degree of similarity (FIG. 1). The Family 11 xylanases, which are of bacterial, yeast, or fungal origin, share the same general molecular structure (see FIG. 2, of CAMPBELL et al. U.S. Pat. No. 5,405,769).

TABLE 1

Family 11 xylanases

| Microbe | Xylanase |
| --- | --- |
| *Aspergillus niger* | Xyn A |
| *Aspergillus kawachii* | Xyn C |
| *Aspergillus tubigensis* | Xyn A |
| *Bacillus circulans* | Xyn A |
| *Bacillus pumilus* | Xyn A |
| *Bacillus subtilis* | Xyn A |
| *Cellulomonas fimi* | Xyn D |
| Chainia spp. | Xyn |
| *Clostridium acetobutylicum* | Xyn B |
| *Clostridium stercorarium* | Xyn A |
| *Fibrobacter succinogenes* | Xyn C |
| *Neocallimastix patriciarum* | Xyn A |
| *Nocardiopsis dassonvillei* | Xyn II |
| *Ruminococcus flavefaciens* | Xyn A |
| *Schizophyllum commune* | Xyn |
| *Streptomyces lividans* | Xyn B |
| *Streptomyces lividans* | Xyn C |
| Streptomyces Sp. No 36a | Xyn |
| *Streptomyces thermoviolaceus* | Xyn II |
| *Thermomonospora fusca* | Xyn A |
| *Trichoderma harzianum* | Xyn |
| *Trichoderma reesei* | Xyn I |
| *Trichoderma reesei* | Xyn II |
| *Trichoderma viride* | Xyn |

An enzyme is classified in Family 11 if it possesses the amino acids common to Family 11, including two glutamic acid (E) residues serving as the essential catalytic residues. These E residues are amino acids 86 and 177 by *Trichoderma reesei* xynII numbering. The corresponding location of the key E residues for other Family 11 xylanases is easily determined by aligning the amino acid sequences, a procedure familiar to those skilled in the art. The amino acids common to Family 11 xylanases are indicated in bold type in FIG. 1 (Wakarchuk, et al, Protein Science 3:467–475 (1994).

The Family 11 xylanases have several advantages over other xylanases in pulp bleaching applications. Most of the Family 11 xylanases are smaller than xylanases in other families. The small size relative to other xylanases is probably beneficial in penetrating the pulp fibers to release xylan from the pulp and enhance the bleaching. The Family 11 xylanases are also "pure" xylanases in terms of their catalytic activity. Unlike the xylanase enzymes in other families, these enzymes hydrolyze only xylan and do not hydrolyze cellulose. Cellulose hydrolysis damages the pulp and is unacceptable in a commercial mill. Among the Family 11 xylanases, the xylanases made by the wood-rotting fungus Trichoderma have been the most widely used in enhancing pulp bleaching. In particular, *Trichoderma reesei* xylanase II (Xyn II), with molecular weight 21,000 and isoelectric point 9.1, has been widely used.

In spite of the advantages of Family 11 xylanases in pulp bleaching, these enzymes have significant drawbacks. The range of temperature and pH that the enzymes exhibits activity on pulp are 45° C. to 55° C. and pH 5.0 to 7.5. A small proportion of mills have operated historically within these ranges. Typically, however, the pulp is at a temperature of 60° C. to 70° C. and a pH of 10 to 12. In some mills the adjustment of temperature and pH are acceptable and routine. However, in many mills achieving the desired treatment conditions causes severe problems.

Depending upon how the bleaching is carried out, cooling of the pulp to temperatures below 60° C. can decrease the efficiency of bleaching to an unacceptable extent. For example, if a mill is bleaching entirely with chlorine dioxide and has a retention time of less than 20 minutes in the chlorination tower, the minimum temperature for adequate bleaching is 60° C. If such a mill cannot heat the pulp between the enzyme treatment and the chlorination, which is often the case, then lower temperatures for the enzyme treatment stage are unacceptable.

Sulfuric acid is used to control the pH of the pulp. Depending on the metallurgy of the equipment, the use of sulfuric acid to control the pH can corrode the steel pipes and other equipment. Sulfuric acid is also a safety hazard.

Another minor problem with using these enzymes, and in particular *Trichoderma reesei* xylanase for bleaching applications is the low thermostability. There is the possibility that the warm ambient temperatures in the mills can inactivate the enzymes after several weeks storage. This problem is not as important as the difficulties of adjusting the temperature and pH of the pulp, but must be taken into account by using refrigerated storage or adding stabilizer compounds to the enzyme.

Therefore, the use of xylanase enzymes, particularly Family 11 xylanase enzymes, active at higher pH and temperature ranges than *Trichoderma reesei* Xyn II would be desirable. It would allow mills that operate outside of the active ranges of Trichoderma xylanase to be able to carry out xylanase treatment and obtain the benefits associated with the treatment. It would also allow mills to carry out xylanase treatment using less sulfuric acid and cooling water than is currently the case, saving production costs and increasing controllability and storage stability.

Before discussing the approaches that have been taken to improving the properties of xylanase enzymes, it is useful to define the following terms.

Thermophilicity is defined herein as the ability of an enzyme to be active at a high temperature. For example, xylanase #1 has more thermophilicity than xylanase #2 if it is capable of hydrolyzing xylan at a higher temperature than xylanase #2. Thermophilicity relates to enzyme activity in the presence of substrate. In the present invention, the substrate can be pulp xylan or purified xylan.

It is important to specify the substrate for purposes of defining the thermophilicity. Most xylanase enzymes are effective at higher temperatures in the hydrolysis of pure xylan than in the treatment of pulp. This is due to a combination of factors relating to the substrates (i.e. inhibitors present in the pulp) and to the length of time, pH, and other aspects of the procedures used to carry out the tests. Quantitative measures of thermophilicity refer herein to pure xylan substrates unless otherwise indicated.

Thermostability is defined herein as the ability of an enzyme to be stored incubated at a high temperature in the absence of xylan substrate, and then exhibit xylanase activity when returned to standard assay conditions. For example, xylanase #1 is more thermostable than xylanase #2 if it can be held at 70° C. for 24 hours and retain all of its activity, while xylanase #2 loses all of its activity after 24 hours at 70° C. In contrast to thermophilicity, thermostability relates to the enzyme activity remaining after incubation in the absence of xylan substrate.

These two terms are defined explicitly to overcome confusion in the literature, where the two terms are often used synonymously or to denote each other. Their present usage is consistent with Mathrani and Ahring, Appl. Microbiol. Biotechnol. 38:23–27 (1992).

Alkalophilicity is defined herein as the ability of an enzyme to be active at a high (alkaline) pH. For example, xylanase #1 has more alkalophilicity than xylanas #2 if it is capable of hydrolyzing xylan at a higher pH than xylanase #2. Alkalophilicity is analogous to thermophilicity and relates to enzyme activity in the presence of xylan substrate.

For improving xylanase for pulp bleaching applications, the thermophilicity and alkalophilicity are much more important than the thermostability. Most of the work described in the prior art has focussed only on improving the thermostability Two generic approaches can be taken to make xylanase enzymes with higher pH and temperature ranges. These are: (1) screening naturally-occurring xylanase enzymes with the desired properties, and (2) using protein engineering to improve the properties of existing xylanase enzymes.

Among naturally occurring xylanases, thermostable enzymes have been isolated from thermophilic microbes, such as *Caldocellum saccharolyticum, Thermatoga maritima* and *Thermatoga sp.* strain FjSS3-B.1, all of which grow at 80°–100° C. (Lüthi et al. 1990; Winterhalter et al. 1995; Simpson et al. 1991). However, all are relatively large in size with high molecular mass of 35–120 kDa (320–1100 residues). Some of these xylanases (*C. saccharolyticum* xylanase A) belong to families other than Family 11 and have both xylanase and cellulase activities (Lüthi et al. 1990). Such cellulase activity is undesirable for pulp bleaching. Furthermore, hyperthermostable xylanases which function normally at extremely high temperatures have low activity at the comparatively lower temperatures for pulp bleaching.

Most of the Family 11 xylanases are effective in pulp bleaching applications at 45° C. to 55° C. However, Family 11 also includes at least two thermostable xylanases, both of which happen to have a higher molecular mass than the other Family 11 xylanases. These xylanases are *Thermomonospora fusca* xylanase (known as TfxA) of 296 amino acids and 32,000 Da (Irwin et al.(1994) Appl. Environ Microbiol. 60:763–770; Wilson et al. 1994, WO 95/12668) and *Clostridium stercorarium* xylanase A which is of 511 amino acids and 56,000 Da with an optimum temperature of 70° C. (Sakka et al. (1993) Biosci. Biotech. Biochem. 57:273–277).

These thermostable xylanase enzymes have some features that are potential problems in pulp bleaching applications. First, the large molecular weight might limit the penetration of the enzymes into the pulp fibers. Second, these enzymes have at least a single copy of a cellulose binding domain (CBD) not present in the other Family 11 xylanases. The CBD, located in the extended C-terminus of TfxA, causes precipitation of the protein and loss of activity in storage.

Therefore, those naturally occurring xylanase enzymes have limitations.

An alternative approach is to carry out protein engineering of a well-known xylanase enzyme. By using protein engineering, specific changes can be made to th protein which might improve a desired property, such as temperature or pH range without compromising on secondary properties such as protein solubility.

When carrying out protein engineering to modify protein properties, one must select the general method to use and then the specific sites and modifications to make. The general methods include (1) site-specific mutagenesis, (2) random mutagenesis, (3) chimeric modification, (4) dimerization, and (5) glycosylation. Within each of these general methods, there are an enormous number of options of specific modifications to the protein that one can make. The effects of different mutations on enzyme characteristics, including thermophilicity and alkalophilicity, are often unpredictable. Generally, only a tiny fraction of all possible modifications, if any, provide significant benefit. Therefore, setting out to improve the properties of a protein by protein engineering is a difficult venture, and the limited success to date with Family 11 xylanases reflects this. The work with modified xylanases is described as follows.

Site-specific mutagenesis involves the modification of specific amino acids in a protein. The modifications based on site-specific mutagenesis are known as point mutations. Site-specific mutagenesis of Family 11 xylanases has been used to produce xylanase enzymes of slightly improved thermostability. CAMPBELL et al, (U.S. Pat. No. 5,405,769) described one manner of improvement of *Bacillus circulans* xylanase (abbreviated BcX), a xylanase of Family 11, through two types of modifications. These were (i) intramolecular disulfide bonds, and (ii) site-specific mutations at the N-terminus.

CAMPBELL et al, describes how disulfide bonds may be inserted between amino acids #98 and #152, #100 and #148, and # (−1) and #187, according to the amino acid numbering of *Bacillus circulans* xylanase. The disulfide modifications improved the thermostability of the xylanase at 620° C. However, these disulfide-modified enzymes showed no gain in thermophilicity (Wakarchuck et al. (1994) Protein Engineering 7:1379–1386). Therefore, thermostability and thermophilicity are not necessarily coupled.

CAMPBELL et al, also describes three modifications (designated T3G, D4Y(F) and N8Y(F)) near the N-terminus of BcX generated mutant xylanase with thermostability at 57° C., a small increase of 2° C. In the PCT publication WO 94/24270, which is related to CAMPBELL et al, there is a description of a fourth advantageous modification, S22P, for the improvement of BcX. This set of four modifications (designated TS19a in the document) showed a higher thermostability and thermophilicity than BcX. However, certain factors would limit the application of these modifications in Family 11 xylanases other than BcX. These mutations to convert residues-3, 4, 8 and 22 (BcX amino acid numbering) respectively into Glycine, Tyrosine (or Phenylalanine), Tyrosine (or Phenylalanine) and Proline, respectively, are irrelevant to the majority of the Family 11 xylanases, as they already possess these "good" residues (see FIG. 1). The best illustration of the inadequacy of these modifications is Xyn II of *Trichoderma reesei*, which possesses all four "good" residues, yet is mediocre in thermophilicity and alkalophilicity.

Random mutagenesis involves the modification of amino acids at random within the entire protein. This method was used to produce a Family 11 xylanase with improved thermostability by ARASE et al ((1993) FEBS Lett. 316:123–127), which described modest improvement of thermostability of a *Bacillus pumilus* xylanase (abbreviated BpX) through modifications at residues-12, 26, 38, 48 and 126 (according to the BpX amino acid numbering). However, ARASE et al did not report any improvement in the thermophilicity or alkalophilicity as a result of their particular modifications. The gain in thermostability by the most improved ARASE et al example in a BpX xylanase was small, only allowing the maintenance of 40% of the residual enzymatic activity after incubation at 57° C. for 20 min. For two other BpX xylanases, with the modifications of residues 12 and 26 around the N-terminus, the gain in thermostability represented the maintenance of 1 and 11% residual activity after incubation, respectively. Furthermore, the BpX xylanase with the residue 26 modification has other modifications as well, so the contribution of this sole modification to thermostability, if any, is unclear from ARASE et al.

A chimeric modification involves substituting some of the amino acids of a protein with a sequence of amino acids from another protein. To our knowledge, such an approach has not been carried out with any Family 11 xylanases.

Dimerization involves combining two molecules into a single protein. This technique has been used to link two BcX molecules via an intermolecular disulfide bond (Wakarchuk, et al, Protein Engineering (1994)). The resulting dimeric BcX showed only an insignificant gain in thermostability, much less than BcX with an intramolecular disulfide bond described above.

It is well known that natural glycosylation, the attachment of carbohydrates to a protein, sometimes improves the thermostability of proteins, including in *Trichoderma reesei* xyn II. Synthetic glycosylation has not been used to improve these properties in a Family 11 xylanase.

No matter which method of protein engineering is used, a key aspect is determining which amino acids to modify, because few choices will improve the properties of the enzyme. This point is illustrated by the work of Sung, et al, Biochem. Cell Biol. 73:253–259 (1995), who modified amino acid #19 in *Trichoderma reesei* xylanase II from asparagine to lysine. This modification decreased the thermophilicity of the enzyme by 3° C.

Therefore, in spite of a large amount of effort with Family 11 xylanases, there has not yet been a modified Family 11 xylanase produced with significantly improved thermophilicity and alkalophilicity. Such an enzyme, and in particular an engineered version of *Trichoderma reesei* xyn II, would have immediate application to the commercial process of producing bleached pulp with decreased requirements for bleaching chemicals while meeting the process conditions of the mills. Such an enzyme would also have potential application in other areas. Some examples of these are as animal feed additives to aid in the digestibility of feedstuffs, where high temperature pelleting makes current enzymes unsuited in many cases; and the processing of wheat and corn for starch production, in which the high temperatures destroy current enzymes.

SUMMARY OF THE INVENTION

The present invention relates to modifying certain specific Family 11 xylanases so as to improve thermophilicity, alkalophilicity, and thermostability. The invention has particular utility in creating enzymes that will allow a pulp mill to obtain the benefits of enhanced bleaching, known to be associated with Family 11 xylanases, but at much higher temperatures and at pH conditions which are more suitable to preferred mill operation parameters, than any xylanases currently available.

The utility of the present invention is specific to Family 11 xylanase enzymes having the following, two essential characteristics:

(i): The enzyme is made by Trichoderma, Bacillus, Aspergillus or Streptomyces (ii): The enzyme comprises the amino acid tyrosine or phenylalanine in position 14 by *Trichoderma reesei* xylanase II numbering, or an equivalent position according to the conventional numbering used to designate other xylanases in enzymes of category (i).

For Family 11 xylanases possessing both of these characteristics, either of the following two types of modifications are taught to suprisingly increase thermophilicity, alkalophilicity, and thermostability of the enzyme:

(1) SITE-SPECIFIC MUTAGENESIS: For those selected xylanases with at least 8 amino acid residues in the N-terminus upstream from position 10 (as per *Trichoderma reesei* xylanase II numbering), the modication comprising a substitution of amino acid 10 with another amino acid. A preferred embodiment is to also substitute amino acids 27 and 29 with valine, methionine, isoleucine or leucine, in addition to the essential step of substituting amino acid 10 with a different amino acid. A most preferred embodiment is to substitute histidine, methionine, and leucine, respectively, for the naturally occuring amino acids which are found at positions 10, 27 and 29.

(2) CHIMERIC MODIFICATION: Replacing a sequence of amino acids in the N-terminal region with an equivalently positioned sequence from *Thermomonospora fusca* xylanase A (Tfx) to form a chimeric enzyme. A preferred embodiment extends the chimeric enzyme upstream from the N-terminus with a tripeptide of Glycine-Arginine-Arginine or a sequence of up to 10 amino acids from the N-terminus of *Clostridium acetobutylicum* (CaX).

Surprisingly, the xylanases modified according to the invention have much improved thermophilicity, alkalophilicity, and thermostability over counterpart unmodified enzymes. Some of these modified xylanases have been found to exhibit up to a 28° C. improvement in thermophilicity, and a 2 pH unit improvement of alkalophilicity over the natural xylanase. Furthermore, the ability of some of the modified xylanases to function at 85° C. and pH 9 is significantly better than any of the confirmed thermophilic Family 11 xylanases, including TfxA.

The inventors believe that no modification of a Family 11 xylanase has previously been reported with such suprising improvements in the thermophilicity, alkalophilicity, and thermostability of the Family 11 xylanases.

The modified *Bacillus circulans* xylanases of the present invention in particular are active at much higher temperatures than the 60°–70° C. temperature ranges disclosed for those modified Bacillus xylanases illustrated within ARASE et al. (BpX therein) and CAMPBELL et al. (BcX therein).

Furthermore, the modified xylanases of the invention demonstrate suprisingly improved properties for the problem of treatment of pulp. The modified xylanases also exhibit the overall potency in treating pulp that is typical of Family 11 xylanases at optimum conditions, but not observed with other xylanases.

Protein modifications as taught herein have not been previously reported for Family 11 xylanases, and no prior disclosures have suggested that the improvements as taught herein might be able to increase thermophilicity, alkalophilicity, or thermostability. ARASE, et al ((1993) FEBS Lett. 316:123–127) described modest improvement of thermostability of a *Bacillus pumilus* xylanase (abbreviated BpX) through modifications at residues-12, 26, 38, 48 and 126, according to the BpX amino acid numbering. These correspond to *Trichoderma reesei* xynII residues 11, 26, 38, 48, and 121, respectively, and not residues according to the principles of the present invention. Furthermore, unlike the present inventors, Arase did not report any improvement in the thermophilicity or alkalophilicity as a result of their teachings. The gain in thermostability by the most improved Arase BpX was small, only allowing the maintenance of 40% of the residual enzymatic activity after incubation at 57° C. for 20 min. For two other BpX xylanases, with the modifications of residues 12 (11 in xynII) and 26, the gain in thermostability represented the maintenance of 1 and 11% residual activity after storage, respectively. Furthermore, the BpX xylanase with the residue 26 modification has other modifications as well, so the contribution of this sole modification to thermostability, if any, was unclear.

CAMPBELL, et al., as well as the CAMPBELL, et al PCT publication, illustrate four modifications (designated T3G, D4Y(F), N8Y(F), and S22P) that might be made to *Bacillus circulars* xylanase (BcX). These changes correspond to amino acids 12, 13, 17, and 31 by *Trichoderma reesei* xylanase numbering. The amino acids taught by CAMPBELL, et al already exist in Trichoderma xylanase and most of the other Family 11 xylanases, and are therefore are deemed esssentially irrelevant toward improving the performance of these xylanases.

The CAMPBELL, et al modifications to *Bacillus circulans* xylanase also do not improve enzyme performance nearly as much as the modified *B. circulars* xylanases of the present invention. Examples 6 and 10 show that the modified *Bacillus circulans* xylanases of the present invention have much higher thermophilicity (+14° C.) and alkalophilicity (+1.5 pH unit) than the best of the CAMPBELL, et al xylanases. In addition, at optimum temperature, the modified Bacillus xylanases of the present invention have three fold higher activity than that of CAMPBELL, et al.

Amino acids 10, 27, and 29 have not been previously suggested to be important to the performance of the Family 11 xylanase enzymes. Suprisingly, the inventors have shown that modification of these amino acids in Trichoderma xyn II to histidine, methionine, and leucine, respectively, significantly increases the thermophilicity, alkalophilicity, and thermostability of the enzyme.

It should be noted that while three of the naturally-occurring Family 11 xylanases have these particular amino acids in these positions. (xylanases produced by *Bacillus pumulis, Clostridium stercorarium* (xyn A), and *Thermomonospora fusca*.), none of those three xylanases exhibit the combination of desirable characteristics taught to result from following the present invention. There is no reason to expect that the thermophilicity is due to the presence of these three amino acids, and the natural xylanases do not point to these three amino acids as key to the enzyme performance. While the Clostridium and Thermonospora xylanases are thermophilic, the *B. pumilis* xylanase is not thermophilic, as it has an optimum temperature below 40° C. (Nissen, et al, 1992). In addition to the three common positions mentioned, there are over 75 positions with identical amino acids in the three xylanases. Both of the Clostridium and Thermonospora xylanases contain unique cellulose binding domains which have been postulated to confer thermostability, as in the other Families of xylanases (Fontes, et al, 1995, Biochem. J. 307:151–158).

The inventors do not purport to claim any of the three natural Family 11 xylanases that possess the preferred residues in positions 10, 27, and 29. The invention is restricted to those xylanases with tyrosine or phenylalanine in position 14 by *T. reesei* xyn II, or the corresponding position in other xylanases. This excludes the B pumilis xylanase, which has aspartic acid in this position 14. The invention is also restricted to xylanases made by Trichoderma, Streptomyces, Aspergillus, and Bacillus. This excludes the Thermomonospora and Clostridium xylanases.

In addition to these three xylanases, two others in Family 11 have methionine in position 27 and leucine in position 29. These are *Clostridium acetobutylicum* xynB (optimum temperature 43° C.) and *Streptomyces lividans* xynC (optimum temperature 55° C.). Neither of these enzymes, however, are thermophilic and therefore neither suggests the modifications to positions 27 and 29 will be useful.

The specific choices of histidine, methionine, and leucine in positions 10, 27, and 29 improves the stability of *Tricho-* derma reesei xynII Given, this fact, it will now be recognized by those skilled in the art that any of a number of amino acids substituted into position 10 will improve the properties of the enzyme. It will also be recognized that, given the improvements due to methionine and leucine in positions 27 and 29, any of the hydrophobic, medium sized amino acids, including valine, isoleucine, leucine, and methionine will be beneficial in these positions.

The important discovery in this aspect of the invention is that positions 10, 27, and 29 are important for the stability of *Trichoderma reesei* xynII. Based on this teaching, it will be appreciated by those skilled in the art that this modification will be beneficial to certain other Family 11 xylanases, and that Family 11 xylanases must satisfy two conditions to benefit from this modification.

First, the Family 11 xylanase must possess at least eight amino acid residues upstream from position 10. Several Family 11 xylanases have a truncated N-terminus. The modification to position 10 is not relevant to xylanases with a truncated N-terminus.

Second, the Family 11 xylanase must possess the amino acid tyrosine or phenylalanine in position 14 by *Trichoderma reesei* xylanase II numbering, or the corresponding position in other xylanases. The side chain of tyrosine or phenylalanine at position 14 points directly into the active site of the protein. Tyrosine and phenylalanine are of similar size and each has a six member aromatic ring that potentially may participate in a stacking interaction with the xylose ring when bound to a xylan substrate. The presence of other amino acids in this position causes significant changes to the overall structure of the protein. Therefore, only those Family 11 xylanase enzymes with either of these amino acids in position 14 will be suitable for modifications to position 10, while Family 11 xylanases with other residues in the corresponding position will not be amenable to this modification.

Of the known Family 11 xylanases of Trichoderma, Streptomyces, Bacillus, and Aspergillus, only *Trichoderma reesei* xyn II, *Trichoderma harzianum* xyn, *Trichoderma viride* xyn, *Streptomyces lividans* xyn B, and *Streptomyces lividans* xyn C meet these two conditions. Therefore, these are the only enzymes presently known that are suitable for the modifications to positions 10, 27, and 29 taught herein.

The chimeric xylanases of the invention have not been previously reported, and there is nothing published to suggest that these particular chimeric xylanases would be beneficial in xylanase performance. Even more surprisingly, in some cases, the thermophilicity and alkalophilicity of the chimeric xylanases is better than that of either of the individual xylanases that comprise the chimeric xylanase. Examples of these enzymes are the modified xylanases NI-BX6 and NI-BX7 in Examples 7 and 11.

The important discovery in this aspect of the invention was that chimeric modification of segments of the N-terminal region of *Trichoderma reesei* xylanase II or *Bacillus circulans* xylanase A with *Thermonospora fusca* xylanase A could increase the thermophilicity, alkalophilicity, and thermostability of the enzymes.

Based on this teaching, it will be recognized by those skilled in the art that chimeric xylanases with improved performance can be formed consisting of the Family 11 xylanases from other Trichoderma, Aspergillus, Streptomyces, and Bacillus, strains with *Thermomonospora fusca* xyn A provided that one condition is met. The Family 11 xylanase must possess the amino acid tyrosine or phenylalanine in position 14 by *Trichoderma reesei* xylanase II numbering, or the corresponding position in other xylanases.

The side chain of tyrosine or phenylalanine in position 14 points directly into the active side of the protein. Tyrosine and phenylalanine are of similar size and their six member aromatic ring can potentially participate in a stacking interaction with the xylose ring when bound to the xylan substrate. *T. fusca* xylanase A has phenylalanine in this position. Only those Family 11 xylanase enzymes with either tyrosine or phenylalanine in position 14 will be suitable for forming chimeric xylanases with *T fusca* xylanase A. Family 11 xylanases with other residues in the corresponding position will not be amenable to this modification.

Of the known Family 11 xylanases of Trichoderma, Streptomyces, Bacillus, and Aspergillus, only *Trichoderma reesei* xyn II, *Trichoderma harzianum* xyn, *Trichoderma viride* xyn, *Trichoderma reesei* xyn I, *Streptomyces lividans* xyn B, *Streptomyces lividans* xyn C *Bacillus circulans* xyn A, *Bacillus subtilis* xyn A, *Aspergillus niger* xyn A, *Aspergillus kawachii* xyn A, and *Aspergillus tubigensis* xyn A meet this condition. Therefore, these are the only enzymes presently known that are suitable for the chimeric modifications taught herein.

Upstream extension of the protein has never been reported to enhance the performance of the Family 11 xylanase enzyme, nor has it been reported to be beneficial in other enzymes. There is no reason to expect that adding amino acids upstream of the N-terminus would improve the thermophilicity, alkalophilicity, or thermostability.

There is no reason to expect that upstream extension with the three amino acids glycine-arginine-arginine would improve the performance of the enzyme. This set of three amino acids is not found in any natural xylanases. Two of the natural Family 11 xylanases, *Bacillus pumulis* and *Clostridium stercorarium*, have only a single arginine directly upstream of the N-terminus. Both xylanases do not have the other arginine and glycine which are essential to the improved thermophilicity of both modified BcX and TrX. The Clostridium enzyme is thermophilic, but the Bacillus enzyme is not, so the natural enzymes do not point to this modification.

There is no reason to expect that upstream extension of the N-terminus with a 10 amino acid sequence from *Clostridium acetoburylicum* xyn B (CaX) would improve the thermophilicity of other Family 11 xylanases. CaX has an optimum temperature of only 43° C., which is no better than the other Family 11 xylanases. Therefore, it is surprising that a sequence of amino acids from this enzyme would improve the thermophilicity of these other xylanases.

The upstream extensions described herein were demonstrated on chimeric xylanases formed by substituting an N-terminal sequence from *T. fusca* xylanase A into xylanase II from *T. reesei* and xylanase A from *B. circulans*. It will be recognized by those skilled in the art that said upstream extension will improve the performance of chimeric xylanases that be can be formed by substituting an N-terminal sequence from *T. fusca* xylanase A into a Family 11 xylanase from Trichoderma, Aspergillus, Streptomyces, and Bacillus.

In summary, the inventors have developed unique enzymes with desirable properties for commercial applications to treating pulp to improve its bleaching.

BRIEF DESCRIPTION OF THE DRAWINGS

FIG. 1 shows the multiple amino acid sequence alignment among several Family 11 xylanases. Each letter represents an amino acid, with the standard amino acid abbreviations used. The divisions into sections are chosen arbitrarily to fit the typeset of the page and have no relevance to the structure of the proteins. The 1 to 30 amino acid numbering for *Trichoderma reesei* xyn Ii is indicated. The amino acids common to at least 80% of the Family 11 xylanases listed are indicated in bold. The residues common to all Family 11 xylanases are underlined. For xylanases of *Clostridium stercorarium, Streptomyces lividans* (xynB), and *Thermomonospora fusca*, only the catalytic core sequences are presented.

FIG. 3 shows the synthetic oligonucleotides for the construction of the gene sequence encoding the Trichoderma xylanase in the plasmid pTvX(3-190).

FIG. 4 shows the synthetic oligonucleotides for the construction of the gene sequence encoding the *Bacillus circulans* xylanase BcX in the plasmid pXYbc.

DETAILED DESCRIPTION OF THE PREFERRED EMBODIMENTS

Figure 2:
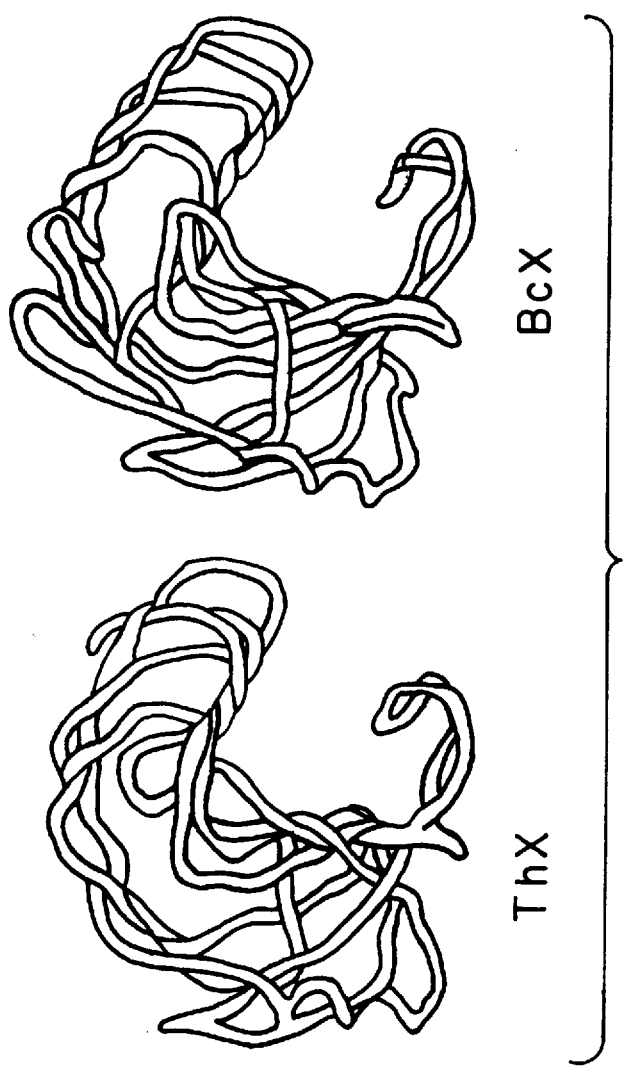
FIG. 2 shows the main chain structures of the fungal *Trichoderma harzianum* xylanase (ThX) and the bacterial *Bacillus circulans* xylanase (BcX).

The invention comprises modified Family 11 xylanase enzymes that exhibit enhanced properties that are important in commercial pulp bleaching applications, namely thermophilicity, alkalophilicity, and thermostability. The modified xylanases exhibit enhanced properties relative to the natural enzymes. The natural enzymes are selected from the group consisting of Family 11 xylanases from Trichoderma, Bacillus, Streptomyces, and Aspergillus. The selection of natural xylanases is further restricted to those xylanases with tyrosine or phenylalanine in position 14 corresponding to the amino acid numbering in *Trichoderma reesei* xylanase II, or the equivalent position in other Family 11 xylanases.

The modifications to the selected xylanase comprise either or both of the following, which are described herein by the amino acid numbering of *Trichoderma reesei* xylanase II and apply to the corresponding aligned amino acids of the other selected Family 11 xylanases:

(1) For selected xylanases with at least 8 amino acid residues in the N-terminus upstream from position 10, substitution of amino acid 10 with another amino acid. (2) Substitution of a sequence of amino acids in the N-terminal region with an equivalently positioned sequence from *Thermomonospora fusca* xylanase A (Tfx) to form a chimeric xylanase, and extending the protein upstream of the N-terminus with a sequence of up to 10 amino acids from another xylanase.

The invention is concerned with modified xylanases and does not claim naturally-occurring xylanases.

In practicing the invention, the starting point is a Family 11 xylanase. An enzyme is classified in Family 11 if it possesses the amino acids common to Family 11, including two glutamic acid (E) residues serving as the essential catalytic residues. These E residues are amino acids 86 and 177 by *Trichoderma reesei* xyn II numbering. The corresponding location of the key E residues for the other Family 11 xylanases is easily determined by aligning the amino acid sequences, a procedure familiar to those skilled in the art. The amino acids common to the Family 11 xylanases are indicated in bold type in FIG. 1. (Wakarchuck, et al, Protein Science 3:467–475 (1994).

The natural Family 11 xylanase used to practice the invention must be among from those Family 11 xylanases made by Trichoderma, Bacillus, Streptomyces, and Aspergillus. The enzyme must also have tyrosine or phenylalanine in position 14 by *Trichoderma xylanase* II numbering, or the corresponding position in other xylanases. The amino acid numbering for *Trichoderma reesei* xyn II is shown in FIG. 1.

The substitution of amino acid 10 refers to this amino acid of *Trichoderma reesei* xylanase II. This modification is claimed only for those selected xylanase enzymes that possess at least 8 amino acid residues upstream of the position corresponding to amino acid 10 in the N-terminus.

In a preferred embodiment, the selected xylanase for this modification consists of *T. reesei* xyn II, *T. harzianum* xyn, *T. viride* xyn, *S. lividans* xyn B, or *S. lividans* xyn C. In a preferred embodiment, in addition to substitution of amino acid 10 with another amino acid, amino acids 27 and 29 are substituted with methionine, isoleucine, leucine, or valine. As with amino acid 10, amino acids 27 and 29 are identified using the *Trichoderma reesei* xylanase II numbering illustrated in FIG. 1.

In a more preferred embodiment, amino acids 10, 27, and 29 are substituted for histidine, methionine, and leucine, respectively. The modified xylanases of this type are identified as NI-TX11, NI-TX12 and NI-TX13 in the Examples.

The chimeric modification of the xylanase consists of removing a sequence of amino acids from the N-terminal region of the selected xylanase and replacing with a sequence of amino acids from the N-terminal region of *Thermomonospora fusca* xylanase A.

As used herein to describe the present invention, the term "N-terminal region" refers to the first 31 amino acids of the *Trichoderma reesei* xylanase II protein closest to the N-terminus. For other Family 11 xylanases, the N-terminal region consists of the amino acids corresponding to the first 31 amino acids of *Trichoderma reesei* xylanase II when the sequences are aligned. The general definition of N-terminal region used in the art is the first ⅓ of the protein closest to the N-terminus. The definition of N-terminal region used in the present invention is consistent with, but necessarily more precise, than the general definition.

The replacement of the amino acids that have been removed is by an amino acid sequence located in the same position relative to the N-terminus of the xylanases from the two microbes. Where the two xylanases have different numbers of amino acids, the replacement sequence of amino acids is at the location that coincides with the original sequence of amino acids when the amino acid sequences of the two enzymes are aligned so as to match as closely as possible. This alignment of amino acids is familiar to those skilled in the art and is illustrated for some of the Family 11 xylanases in FIG. 1.

In a preferred embodiment, the sequence of amino acids 10 to 29 from TrX or equivalent aligned amino acid sequence of another Family 11 xylanase is substituted by the corresponding aligned sequence of amino acids from *Thermomonospora fusca* xylanase A. An example of this modified xylanase is identified as NI-TX4 in the Examples.

In a preferred embodiment, the sequence of amino acids 1 to 29 from TrX or equivalent aligned amino acid sequence of another Family 11 xylanase is substituted by the equivalent aligned sequence of amino acids from *Thermomonospora fusca* xylanase A. An example of this modified xylanase is identified as NI-TX3 in the Examples.

In another preferred embodiment, the 1 to 22 amino acid sequence of *Bacillus circulans* xylanase (BcX) is substituted for the 1 to 31 amino acid sequence of Tfx. These two sequences are aligned based on the sequences in FIG. 1. An example of this modified xylanase is identified as NI-BX2 in the Examples.

In a preferred embodiment, the selected xylanase for this modification consists of *Trichoderma reesei* xyn II, *Trichoderma harzianum* xyn, *Trichoderma viride* xyn, *Streptomyces lividans* xyn B, *Streptomyces lividans* xyn C, *Bacillus circulans* xyn A, *Bacillus subtilis* xyn A, *Aspergillus niger* xyn A, *Aspergillus kawachii* xyn A, or *Aspergillus tubigensis* xyn A.

Upstream extension consists of adding a sequence of up to 10 amino acids to the low molecular mass Family 11 xylanase upstream of the N-terminus. This upstream extension is carried out in combination with a chimeric modification of the selected Family 11 xylanase with *T. fusca* xylanase A described herein.

In a preferred embodiment, a tripeptide comprising glycine-arginine-(arginine or lysine) is added in the upstream extension from the N-terminus of the Family 11 xylanase, and this extension is carried out in combination with a chimeric modification. Examples of modified xylanases with these modifications are NI-TX9 and NI-BX7.

In a preferred embodiment, one to three basic amino acids are added between the N-terminus and a sequence of 5 to 9 amino acids from the Family 11 xylanase *Clostridium acetoburylicum* xynB (CaX), and this extension is carried out in combination with a chimeric modification. Examples of modified xylanases with these modifications are NI-TX8, NI-BX5, and NI-BX6 identified in the Examples.

In a preferred embodiment, a sequence of amino acids ASAR or ASAK are added upstream of the N-terminus and this extension is carried out in combination with a chimeric modification. Examples of modified xylanases with these modifications are NI-TX7, NI-BX3, and NI-BX4.

Another set of preferred embodiments involves using the modified enzymes of the present invention to treat pulp and improve its bleachability. Said enzyme treatment is carried out at temperatures of 55° C. to 75° C. that are not in the acceptable range for enhancing the bleaching of pulp using natural Family 11 xylanases. In a preferred embodiment, said enzyme treatment is carried out at a pH of 7.5 to 9.0 that is not in the acceptable range for enhancing the bleaching of pulp using natural Family 11 xylanases.

It is well known to those skilled in the art that the xylanase enzymes of the invention might be useful in applications outside of pulp bleaching. For example, these enzymes might be useful as animal feed additives to aid in the digestibility of feedstuffs, where high temperature pelleting makes current enzymes unsuited in many cases. In addition, these enzymes might be useful in the processing of wheat and corn for starch production, in which the high process temperatures destroy current enzymes. It is well known to those skilled in the art that in these or other applications, the modified xylanase enzymes of the invention can be used in the presence of other enzymes, including but not limited to cellulase, mannanase, beta-glucanase, and amylase The present invention will be further illustrated by detailed description of the following examples, which are not to be construed as limiting. Modified xylanases according to the Examples are listed in TABLES 2 and 3.

TABLE 2

*Trichoderma reesei* xylanases

| xylanase | description |
| --- | --- |
| natl TrX | natural *T. reesei* xylanase. |
| rec TrX | recombinant TrX produced by *E. coli*, without posttranslational modification. |
| TvX (3–190) | recombinant TrX with 5 different residues: Ala-1, Ser-21, Gly-4, Phe-9, Thr-65 and Thr-143. |
| NI-TX1 | TvX (3–190) with a mutation Q162H. |
| NI-TX2 | chimeric; the (1–29) sequence of NI-TX1 was substituted by the same region of Tfx and the N-terminus was extended upstream with the tetrapeptide ASHA added to positions (−4) to (−1). |
| NI-TX3 | chimeric; the (1–29) sequence of NI-TX1 was substituted by the same region of Tfx. |
| NI-TX4 | chimeric; the (10–29) sequence of NI-TX1 was substituted by the same region of Tfx. |
| NI-TX5 | chimeric; the TYTN aa sequence in the (26–29) sequence of NI-TX1 was substituted by the same region of Tfx. |
| NI-TX6 | NI-TX1 with mutations Y27M and N29L. |
| NI-TX7 | chimeric; NI-TX3 was extended with the tetrapeptide ASAR in the (−4) to (−1) positions |
| NI-TX8 | chimeric; NI-TX3 was extended upstream in the (−10) to (−1) positions, with (i) the *C. acetobutylicum* xynB (23–31) sequence from the (−10) to (−2) positions, and (ii) Arg at the (−1) position (Tfx aa numbering). |
| NI-TX9 | chimeric; NI-TX3 was extended upstream with a tripeptide GRR from the (−3) to (−1) positions (Tfx aa numbering). |
| NI-TX10 | NI-TX1 with mutations N10H and N11D. |
| NI-TX11 | NI-TX1 with mutations N10H, Y27M, and N29L. |
| NI-TX12 | NI-TX1 with mutations N10H, N11D, Y27M, and N29L. |
| NI-TX13 | recombinant TrX with mutations N10H, Y27M, and N29L. |

TABLE 3

Bacillus circulans xylanases

| xylanase | description |
|---|---|
| BcX | wild type B. circulans xylanase. |
| NI-BX1 | chimeric; the (1–22) sequence of BcX was substituted by Tfx(1–31) sequence, and the N-terminus was extended with the tetrapeptide ASHA in the −1 to −4 positions. Modification is same as in NI-TX2. |
| NI-BX2 | chimeric; the (1–22) sequence of BcX was substituted by Tfx (1–31) sequence. Modification is same as in M-TX3. |
| NI-BX3 | chimeric; N-terminus is identical to NI-BX2, but with the N-terminus extended with the tetrapeptide ASAR at the (−4) to (−1) position (Tfx aa numbering). Modification is same as in NI-TX7. |
| NI-BX4 | chimeric; N-terminus is identical to NI-BX2, but with the tetrapeptide ASAK at the (−4) to (−1) positions (Tfx aa numbering). |
| NI-BX5 | chimeric; the N-terminus extension of NI-BX2 was with (i) the C. acetobutylicum xynB (23–31) sequence at the (−10) to (−2) position (Tfx aa numbering), and (ii) Arg at the (−1) position. Modification is same as in NI-TX8. |
| NI-BX6 | chimeric; NI-BX5 with substitution by Arg at the (−2) position and Gly at the (-3) position (Tfx aa numbering). |
| NI-BX7 | chimeric; NI-BX2 was extended upstream with a tripeptide GRR from the (−3) to (−1) positions (Tfx numbering). Modification is same as in NI-TX9. |

Examples 1 through 3 hereafter will describe the production and purification of modified xylanases according to the invention. The suprisingly enhanced thermophilicity, alkalophilicity, and thermostability of modified xylanases NI-TX1 through NI-TX11 and NI-BX1 through NI-BX7 are demonstrated using xylan as the substrate in Examples 4 through 13. The performance of xylanase on a xylan substrate is well known to correlate well with that performance which is observed during actual treatment of pulp. A confirmation of suprisingly enhanced performance using modified xylanases according to the invention in the treatment of pulp, before bleaching, is provided for selected modified xylanases in Examples 14 and 15.

EXAMPLE 1

Construction of the Trichoderma Ressei Modified Xylanases NI-TX

Basic recombinant DNA methods like plasmid preparation, restriction enzyme digestion, polymerase chain reaction, oligonucleotide phosphorylation, ligation, transformation and DNA hybridization were performed according to well-established protocols familiar to those skilled in the art (Sung et al., 1986) or as recommended by the manufacturer of the enzymes or kit. The buffer for many enzymes have been supplied as part of a kit or reconstituted following the instruction of the manufacturers. Restriction enzymes, T4 polynucleotide kinase and T4 DNA ligase were purchased from New England BioLabs LTD, Mississauga, Ont. Gene-Amp PCR reagent kit was purchased from Perkin-Elmer. A precursor plasmid pXYbc, which is a pUC type plasmid with a Bacillus circulars xylanase gene inserted, has previously been prepared and published (Sung et al, 1993; Campbell et a. U.S. Pat. No. 5,405,769 issued on Apr. 11, 1995). A commonly used E. coli strain, HB101 (Clonetech Lab, Palo Alto, Calif.) was used as transformation and expression host for all gene construct. Birchwood xylan was purchased from Sigma (St. Louis, Mo). Hydroxybenzoic acid hydrazide (HBAH) was purchased from Aldricht. Oligonucleotides were prepared with an Applied Biosystem DNA synthesizer, model 380B. Xylanase assays have been performed in a covered circulating water bath (Haake type F 4391) with a fluctuation of ±0.1° C. Temperature of the water bath was confirmed with a thermocouple.

A. Construction of the precursor plasmid pTvX(3-190).

The precursor plasmid pTvX(3-190) for all subsequent mutations has previously prepared and its construction has already been published (Sung et al, 1995). This plasmid is derived from plasmid pXYbc, through a substitution of the Bacillus circulans xylanase gene of the latter by a newly assembled Trichoderma xylanase gene. Expression of this Trichoderma xylanase and other mutant xylanase subsequently described are under the control of the lac promoter. The total assembly of the Trichoderma xylanase gene required two stages, initially for the (92–190) region, then followed by the (1–92) region. The protocol for the construction of this gene is routine and identical to the standard published procedure for many other genes, using enzymatic phosphorylation of overlapping synthetic oligonucleotides which encodes xylanase, followed by their ligation into an appropriately cut plasmid.

Initially ten overlapping oligonucleotides (XyTv-101 to 110) encoding the TvX(92–190) sequence (FIG. 3), were designed with codon usage frequency imitating that of E. coli. The SalI and BglII cohesive ends of two terminal oligonucleotides enabled the enzymatic ligation of the ten fragments to the SalI-BglII linearized plasmid pXYbc. Ten oligonucleotides XyTv-101 to XyTv-110 (50 pmol, 1 μL for each) encoding the (92–190) region of Trichoderma xylanase was phosphorylated in a mixture containing 10× standard kinase buffer (0.4 μL), 1 mM ATP (4 μL), T4 DNA kinase (5 units), and water (3 μL). Phosphorylation reaction was carried out for 1 h at 37° C. The solutions were then combined and heated to 70° C. for 10 min. After being cooled slowly to room temperature, the combined solutions were added to a mixture of 4 mM ATP (3.5 μL), SalI-BglII linearized plasmid pXYbc (0.1 pmol), and T4 DNA ligase (3.5 μL) and incubated at 12° C. for 20 h. Aliquots of the ligation mixture were used to transform E. coli HB101 in YT plate (8 g yeast extract, 5 g bacto-tryptone, 5 g NaCl, 15 g of agar in 1 L of water) containing ampicillin (100 mg/L).

For the preparation of a hybridization probe, one of the oligonucleotide XyTv-110 (10 pmol, 1 μL) was phosphorylated $^{32}$P-ATP (10 pmol, 3 μL) in T4 DNA kinase (1 μL), 10× kinase buffer (1 μL), and water (4 μL) at 37° C. for 1 h.

Transformants were selected randomly for hybridization analysis. Colonies were grown on nylon filters on YT plates with ampicillin overnight. They were then denatured with 0.5N NAOH–1.5M NaCl (10 min) and neutralized with 0.5N Tris-HCl (pH 7.0) –1.5M NaCl (10 min). After irradiation by UV of 254 nm for 8 min, the filters were washed with 6× SSC –0.05% TritonX-100 for 30 min. Cell debris was scraped off completely. After another 30 min. in fresh solution, the duplicate filters were transferred individually into separate mixtures of 6× SSC –1% dextran sulphate –0.05% TritonX-100 –1× Denhardt's hybridization fluid. The $^{32}$P-labelled probe was added to the filter. After 16 h at 45° C., the filter was washed twice with 6× SSC –0.05% TritonX-100 at room temperature for 5 min. and then at 65° C. for 30 min. Positively hybridized clones with the intermediate plasmid pBcX.TvX were identified by autoradiographic analysis.

The above protocol, involving enzymatic phosphorylation of synthetic overlapping oligonucleotides and ligation into a linearized plasmid, has again been used in the assembly of the TX(1–92) region and in the cassette mutagenesis for the subsequent generation of several mutant series NI-TX and NI-BX described in this invention.

17

For the assembly of the TX(1–92) region to complete the full-length Trichoderma gene, the intermediate plasmid pBcX.TvX was linearized by NheI and KpnI endonucleases to release the DNA insert for BcX(1–83). With NheI and KpnI cohesive ends, ten overlapping oligonucleotides (XyTv-1 to −10) encoding the published TvX(3–91) sequence were ligated into the linearized plasmid pBcX-.TvX (FIG. 3), via the protocol described above. The new plasmid pTvX(3–190) therefore harbored a synthetic TvX (3–190) gene. As compared to the natural TrX, the recombinant TvX(3–190) has five different residues: Ala-1, Ser-2, Gly-4, Phe-9, Thr-65 and Thr-143.

For comparison, a gene encoding the natural TrX has also been assembled in the same manner with the five natural residues. This has also been published (Sung et al, 1995). Expression of this gene in *E. coli* generated a recombinant version of TrX (rec. TrX). As indicated below and in the same report by Sung et al (1995), the performance characteristics of both TvX(3–190) and rec. TrX were identical. However, both *E. coli*-expressed xylanases were worse than the natural TrX (natl TrX) in thermophilicity and thermostability, probably due to the lack of posttranslational modification as in the case of natural TrX.

B. Construction of the plasmid pNI-TX1

All mutant xylanases genes including both NI-TX and NI-BX series described below have been constructed via the

18

The mutant NI-TX1 was identical to TvX(3-190) with a single mutation Q162H. The construction of the plasmid pNI-TX1 was through ligation of oligonucleotides TX-162H-1 and TX-162H-2 (shown below) into NsiI/AvrII-linearized plasmid pTvX(3-190) in a cassette mutagenesis.

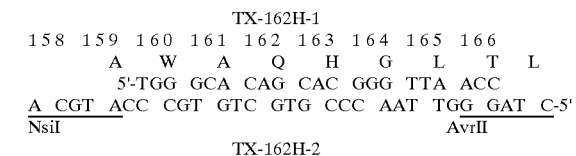

C. Construction of the plasmid pNI-TX2

The mutant NI-TX2 is a modified version of NI-TX1, with (i) the (1–29) sequence of the latter substituted by the Tfx(1–29) sequence and (ii) the N-terminus extended upstream with the tetrapeptide ASHA in positions −4 to −1. The plasmid pNI-TX2 was constructed through the ligation of overlapping oligonucleotides Tfx–1, −2, −3 and −4, that encoded the Tfx(1–29) sequence, to the NheI/ApaI-linearized plasmid of pNI-TX1 in a cassette mutagenesis.

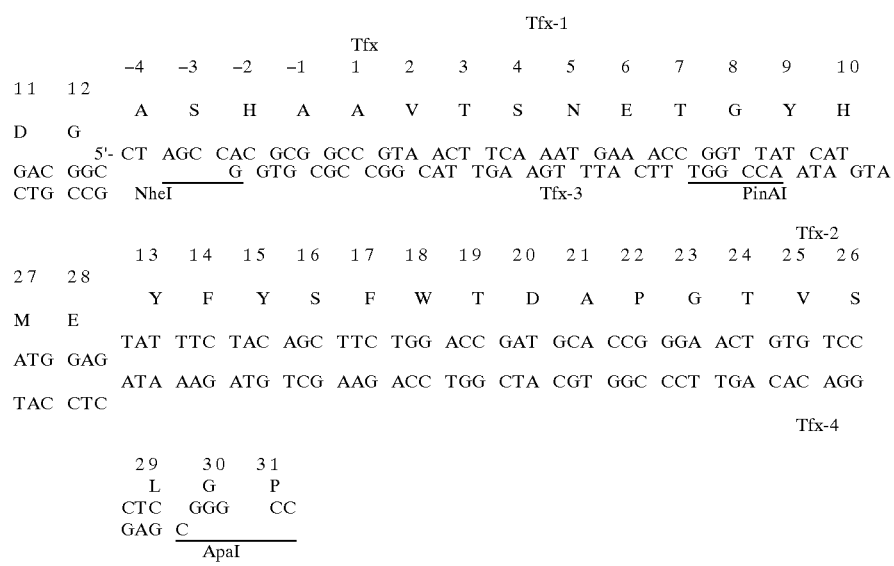

method of cassette mutagenesis. The protocol for the cassette mutagenesis was identical to that for gene assembly fully described above. Such cassette mutagenesis involved (i) enzymatic phosphorylation of overlapping synthetic oligonucleotides, (ii) their ligation with the linearized plasmid, (iii) transformation into the *E. coli* HB101 competent cells, (iv) identification of the mutant transformants via hybridization with the labelled oligonucleotide as probe, and (v) confirmation of the mutation through dideoxy nucleotide sequencing.

D. Construction of the plasmid pNI-TX3

The mutant NI-TX3 is a modified version of NI-TX2, without the extra tetrapeptide ASHA from the (−4) to (−1) positions as in the latter. The plasmid pNI-TX3 was prepared via substitution of the coding sequence for Tfx(1–6) in the NI-TX2 gene with a new coding sequence for TrX (1–6) minus the extra upstream residues. This was accomplished via ligation of the oligonucleotides Tfx(1–6)-1 and Tfx (1–6)-2 into the NheI/PinAI-linearized plasmid pNI-TX2 in a cassette mutagenesis.

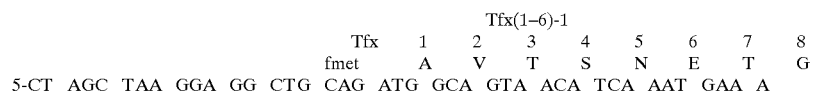

-continued

E. Construction of the plasmid pNI-TX4

The mutant NI-TX4 is a modified version of NI-TX1, with the (10–29) sequence of the latter substituted by the Tfx(10–29) sequence. The plasmid pNI-TX4 was prepared via substitution of the coding sequence for Tfx(1–6) in NI-TX2 gene with that of TrX (1–6). This was accomplished via ligation of the oligonucleotides TX-1f and TX-8f into the NheI/PinAI-linearized plasmid pNI-TX2 in a cassette mutagenesis.

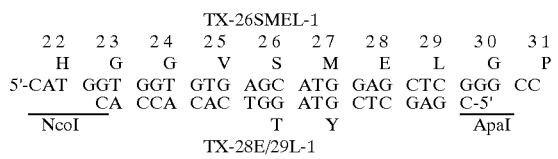

F

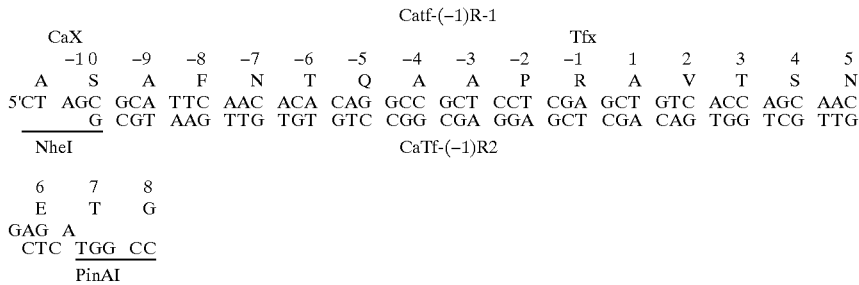

```
                                     Catf-(−1)R-1
   CaX                                                      Tfx
      −10   −9    −8    −7    −6    −5    −4    −3    −2    −1    1     2     3     4     5
    A    S     A     F     N     T     Q     A     A     P     R     A     V     T     S     N
5'CT  AGC  GCA  TTC  AAC  ACA  CAG  GCC  GCT  CCT  CGA  GCT  GTC  ACC  AGC  AAC
         G  CGT  AAG  TTG  TGT  GTC  CGG  CGA  GGA  GCT  CGA  CAG  TGG  TCG  TTG
   NheI                                  CaTf-(−1)R2

6     7     8
  E     T     G
GAG  A
  CTC  TGG  CC
       PinAI
```

K. Construction of the plasmid pNI-TX9

The mutant NI-TX9 is a modified version of NI-TX3, with the N-terminus extended upstream with a tripeptide GRR from the (−3) to (−1) positions (Tfx aa numbering).

PCR primers were constructed to introduce the tripeptide GRR from the (−3) to (−1) positions. The 5' and 3' primers are shown below:

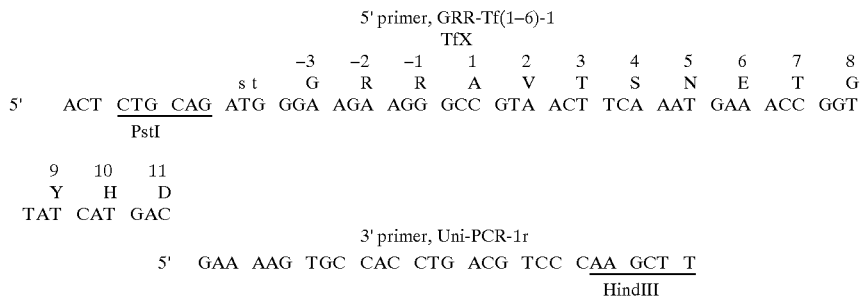

```
                                       5' primer, GRR-Tf(1–6)-1
                                                 TfX
                                   −3    −2    −1     1     2     3     4     5     6     7     8
                             st     G     R     R     A     V     T     S     N     E     T     G
5'   ACT  CTG CAG  ATG  GGA  AGA  AGG  GCC  GTA  ACT  TCA  AAT  GAA  ACC  GGT
          PstI 9    10    11
  Y     H     D
TAT  CAT  GAC
                                       3' primer, Uni-PCR-1r
          5'   GAA  AAG  TGC  CAC  CTG  ACG  TCC  CAA  GCT  T
                                                      HindIII
```

The plasmid pNI-TX2 was used as a template for PCR. The reaction solution contained the plasmid pNI-TX2 DNA (50 ng, 15 $\mu$L), 5 $\mu$L of 10× buffer (100 mM KCl, 100 mM ammonium sulfate, 200 mM Tris-HCl pH 8.8, 40 mM magnesium sulfate, 1% TritonX-100, 100 $\mu$g/ml BSA), 5 $\mu$L of 5 mM dNTPs, 5' primer solution (25 pmol, 2.5 $\mu$L), 3' primer solution (25 pmol, 2.5 $\mu$L) and water (19 $\mu$L).

The reaction was covered with paraffin oil (50 $\mu$L) to prevent evaporation. The reaction mixture was pre-warmed to 94° C. without enzyme for 5 min., then the reaction mixture was cooled to 72° C., then the enzyme DNA polymerase (1 $\mu$L,1U) was added. The reaction was incubated in a temperature cycler for 30 cycles of 94° C. for 1 min., 55° C. for 2 min. and then 72° C. for 2 min. The yield of the PCR product was approximately 1 $\mu$g of a 600 bp fragment. This fragment was purified from an agarose gel.

The resulting PCR product was cut with restriction enzymes PstI and HindIII, and was subsequently ligated into the PstI/HindIII-linearized plasmid pNI-TX3 in a cassette mutagenesis. Transformation in *E. coli* HB101 yielded the plasmid pNI-TX9.

L. Construction of the plasmid pNI-TX10

The mutant NI-TX10 was identical to NI-TX1, but with two single mutations H10N and D11N. The construction of the plasmid pNI-TX12 was through ligation of oligonucleotides TX10HD-1 and TX10HD-2 (shown below) into the PinAI/ApaI-linearized plasmid pNI-TX1 in a cassette mutagenesis.

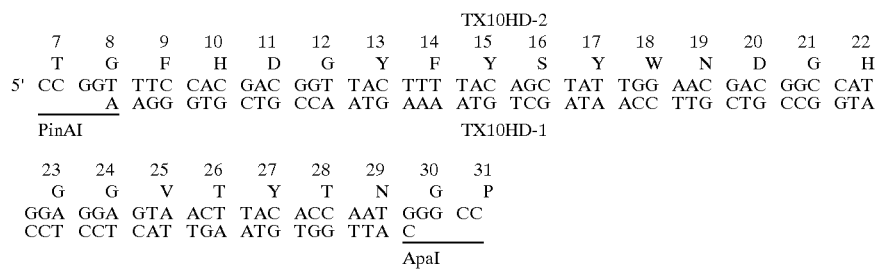

```
                                              TX10HD-2
     7     8     9    10    11    12    13    14    15    16    17    18    19    20    21    22
     T     G     F     H     D     G     Y     F     Y     S     Y     W     N     D     G     H
5'  CC  GGT  TTC  CAC  GAC  GGT  TAC  TTT  TAC  AGC  TAT  TGG  AAC  GAC  GGC  CAT
           A  AGG  GTG  CTG  CCA  ATG  AAA  ATG  TCG  ATA  ACC  TTG  CTG  CCG  GTA
    PinAI                                     TX10HD-1

23    24    25    26    27    28    29    30    31
   G     G     V     T     Y     T     N     G     P
 GGA  GGA  GTA  ACT  TAC  ACC  AAT  GGG  CC
 CCT  CCT  CAT  TGA  ATG  TGG  TTA  C
                                       ApaI
```

M. Construction of the plasmid pNI-TX11 and pNI-TX12

The mutant NI-TX11 and NI-TX12 were identical to NI-TX1 with three and four single mutations respectively. NI-TX11 has three mutations N10H, Y27M and N29L. NI-TX12 has four mutations N10H, N11D, Y27M and N29L.

The desirable gene has been constructed through PCR with the plasmid pNI-TX6 a template. The 5' and 3' PCR primers TX10HD/N-1 and Uni-PCR-1r, and the PCR protocol for the introduction of the tripeptide GRR have been described in the construction of pNI-TX9.

The resulting PCR product was cut with restriction enzymes PinAI and HindIII, and was subsequently ligated into the PinAI/HindIII-linearized plasmid pNI-TX1 in a cassette mutagenesis. Tranformation in *E. coli* HB101 yielded both the plasmids pNI-11 and pNI-12. Their identities were established by nucleotide sequencing.

A. Construction of the plasmid pNI-BX1

The modification in NI-BX1 has been applied in the preparation of NI-TX2. The mutant NI-BX1 is a modified version of BcX, with a substitution of the (1–22) region of the latter by Tfx(1–31) sequence. The plasmid pNI-BX1 was

```
                   5' primer                     TX10HD/N-1
              7    8    9    10   11   12   13   14   15   16   17   18   19   20
              T    G    Y    H    D/   N    G    Y    F    Y    S    Y    W    N    D
5' GAA ACC GGT TAC CAC XAC GGT TAC TTT TAC AGC TAT TGG AAC GAT
        Pin AI 21   22
        G    H
      GGC  C
      X = G + A
```

N. Construction of the plasmid pNI-TX13

The mutant NI-TX13, is identical to the recombinant wild type TrX, but with the three mutations N10H, Y27M and N29L described in NI-TX11. The generation of this mutant requires the conversion of the residues at positions 1–4 in mutant NI-TX11 to those of TrX. Three residues Ala-1, Ser-2, Gly-4 in mutant NI-TX11 has been converted into Gln, Thr and Gln respectively. The construction of the plasmid pNI-TX13 was through ligation of oligonucleotides TrX1f and TrX8f (shown below) into the NheI/PinAI-linearized plasmid pNI-TX11 in a cassette mutagenesis.

constructed through the ligation of overlapping oligonucleotides Tfx-1, -2b, -3 and -4b, that encoded the Tfx(1–31) sequence, to the NheI/BspEI-linearized plasmid of pXYBc in a cassette mutagenesis.

```
                           TrX1f
             TrX    1    2    3    4    5    6    7    8
             fmet   Q    T    I    Q    P    G    T    G
5-CT AGC TAA GGA GG CTG CAG ATG CAA ACA ATA CAA CCA GGA A
         G ATT CCT CC GAC GTC TAC GTT TGT TAT GTT GGT CCT TGG CC
       NheI                      TrX8f                          PinAI
```

EXAMPLE 2

CONSTRUCTION OF THE BACILLUS CIRCULANS MUTANT XYLANASES NI-BX

The modifications in the fungal Trichoderma xylanases NI-TX2, NI-TX3, NI-TX7, NI-TX8 and NI-TX9 have also been repeated in the bacterial *B. circulans* xylanase (BcX).

```
               11   12   13   14   15   16   17   18   19   20   21   22   23   24   25   26
               D    G    Y    F    Y    S    F    W    T    D    A    P    G    T    V    S
                                                     ACC GAT GCC CCG  GGA ACT GTG AGT

3'-G CCG ATA AAG ATG TCG AAG ACC TGG CTA CGG  GGC CCT TGA  CAC TCA
                                            Tfx-4b 27   28   29   30   31
               M    E    L    G    P
              ATG GAG CTC GGC C
              TAC CTC GAG CCG GGG CC
                                 BspEI
```

The precursor plasmid pXYbc has previously prepared and published (Sung et al, 1993; Campbell et a. U.S. Pat. No. 5,405,769 issued on Apr. 11, 1995), and would only be briefly described. A synthetic gene encoding the *B. circulans* xylanase (BcX) was assembled through the enzymatic phosphorylation by T4 DNA kinase and ligation of overlapping synthetic oligonucleotides into a linearized plasmid by T4 DNA ligase (FIG. 4)(Sung et al, 1993), via the same protocol described above for pXyTv(3-190).

B. Construction of the plasmid pNI-BX2

This modification in NI-BX2 has been applied in the preparation of NI-TX3. The mutant NI-BX2 is a modified version of NI-BX1, but without the extra residues from the (−4) to (−1) positions as in the latter. The plasmid pNI-BX2 was prepared via substitution of the coding sequence for Tfx(1–6) in the NI-BX1 gene with a new coding sequence for TrX(1–6) minus the upstream extra residues. This was accomplished via ligation of the oligonucleotides Tfx(1–6)

−1 and Tfx(1–6)-2 into the NheI/PinAI-linearized plasmid pNI-BX1 in a cassette mutagenesis.

C. Construction of the plasmid pNI-BX3

The modification in NI-BX3 has been applied in the preparation of NI-TX7. The mutant NI-BX3 is a modified version of NI-BX1, but with its N-terminus extended by one Arg residue at the (−1) position. The construction of the plasmid pNI-BX3 was accomplished via ligation of the oligonucleotides Tf-(−1)R-1 and Tf-(−1)R-2 into the NheI/PinAI-linearized plasmid pNI-BX1 in a cassette mutagenesis.

D. Construction of the plasmid pNI-BX4

The mutant NI-BX4 is identical to NI-BX3, but with an Arg residue replaced by a Lys residue at the (−1) position. The construction of the plasmid pNI-BX4 was accomplished via ligation of the oligonucleotides Tf-(−1)K-1 and Tf-(−1)K-2 into the NheI/PinAI-linearized plasmid pNI-BX1 in a cassette mutagenesis.

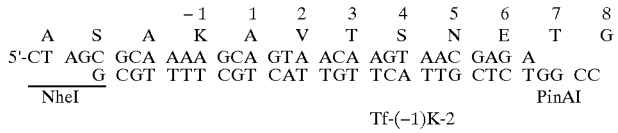

E. Construction of the plasmids pNI-BX4-K(−1)D and pNI-BX4-K(−1)E

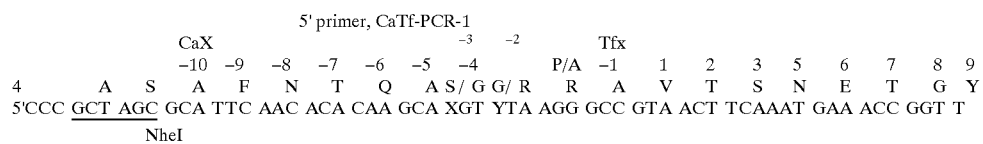

where X = A and G mixture
Y = G and C mixture.

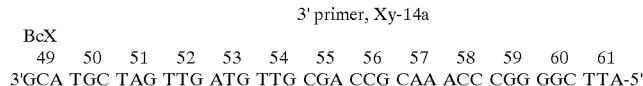

The mutant NI-BX4-K(−1)D and NI-BX4-K(−1)E are identical to NI-BX4 or NI-BX3, but with an acidic residue Asp or Glu substituting the basic residue at the (−1) position. The construction of the plasmids was accomplished via ligation of the heteroduplex oligonucleotides Tf-(−1)D-1 and Tf-(−1)E-2 into the NheI/PinAI-linearized plasmid pNI-BX1 in a cassette mutagenesis. Subcloning of the prepared plasmid yielded the target plasmids.

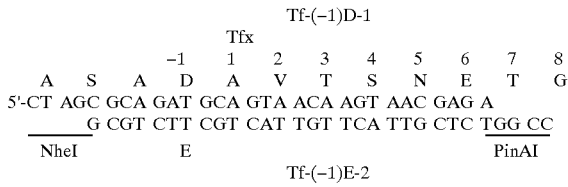

F. Construction of the plasmid pNI-BX5

The modification in NI-BX5 has been applied in the preparation of NI-TX8. The mutant NI-BX5 has (i) a substitution of its (1–29) sequence by the Tfx(1–29) aa sequence, (ii) an extension of an Arg residue at (−1) position (Tfx aa numbering), and (iii) a further extension upstream with an *C. acetobutylicum* xynB (23–31) sequence from (−10) to (−2) positions. The construction of the plasmid pNI-BX5 was accomplished via ligation of the oligonucleotides CaTf-(−1)R-1 and CaTf-(−1)R-2 into the NheI/PinAI-linearized plasmid pNI-BX1 in a cassette mutagenesis.

G. Construction of the plasmid pNI-BX6

PCR primers were constructed to generate variation at the positions-(−3) and (−2) of NI-BX5. Mixed bases encoded residues Ser and Gly at position-(−3), and Pro, Ala, Gly and Arg at position-(−2). The 5′ and 3′ primers are shown below:

The plasmid pNI-BX1 was used as a template for PCR. The PCR protocol has been described in the construction of NI-TX9. The yield of the PCR product was approximately 1 μg of a 200 bp fragment. This fragment was purified from an agarose gel.

The resulting PCR product was cut with restriction enzymes NheI and BamHI and was subsequently ligated into the NheI/BamHI-linearized plasmid pXYBc in a cassette mutagenesis. Tranformation in *E. coli* HB101 yielded plasmids harboring different xylanase genes encoding different residues at the (−3) and (−2) position. After the study of the enzymatic characteristics of the expressed xylanases in the Examples below, the most improved mutant was NI-BX6. Dideoxy nucleotide sequencing of NI-BX6 revealed residues Gly and Arg respectively in positions-(−3) and (−2).

H. Construction of the plasmid pNI-BX7

The mutant NI-BX7 is a modified version of NI-BX2, with the N-terminus extended upstream with a tripeptide GRR from the (−3) to (−1) positions (Tfx aa numbering).

The desirable gene has been constructed through PCR with the plasmid pNI-BX1 as a template. The PCR primers GRR-Tf(1–6)-1 and Uni-PCR-1r, and the PCR protocol for the introduction of the tripeptide GRR have been described in the construction of NI-TX9.

The resulting PCR product was cut with restriction enzymes PstI and HindIII, and was subsequently ligated into the PstI/HindIII-linearized plasmid pNI-TX3 in a cassette mutagenesis. Tranformation in *E. coli* HB101 yielded the plasmid pNI-BX7.

EXAMPLE 3

Production and Assays of Modified Xykabases (A) Production of xylanases

The culture condition was identical to the well-established protocol described for other *E. coli*-expressed xylanases. A 5 ml of overnight innoculant in 2YT medium (16 g yeast extract, 10 g bacto-tryptone, 5 g NaCl, 1 L of water) containing ampicillin (100 mg/L) was added to 2YT medium (1 L) with ampicillin. The cultures were grown for with shaking (200 rpm) at 37° C. After 16 hr, cells were harvested.

(B) Purification of modified xylanases

Protein samples were prepared from cells by first making an extract of the cells by grinding 10 g of the cell paste with 25 g of alumina powder. After grinding to smooth mixture, small amounts (5 mL) of ice cold buffer A (10 mM sodium acetate, pH 5.5 for BcX mutants) or buffer B (10 mM sodium acetate, pH 4.6 for TX mutants) were added and the mixture ground vigorously between additions. The alumina and cell debris were removed by centrifugation of the mixture at 8000×g for 30 min.

Before column chromatography, the supernatant (25 mL) of modified xylanases were pretreated in one of the following ways:

(1) NI-BX1, NI-BX2, NI-TX1, NI-TX2, NI-TX3, NI-TX4, NI-TX6, NI-TX7, NI-TX10, NI-TX11, NI-TX12, NI-TX13.

Dialysis overnight at 4° C. against 3 L buffer A, with dialysis tubing (3500 molecular weight cutoff). A slight precipitate formed in the dialysis bag, which is removed by centrifugation at 8000×g for 15 min.

(2) NI-BX3, NI-BX4, NI-BX5, NI-BX6, NI-BX7

Heating at 60° C. for 20 min, then 68° C. for 30 min and centrifugation to remove a large amount of precipitate. The supernatant was acidified to pH 4.6, frozen at −20° C. overnight thawed and centrifuged to remove more precipitate.

(3) NI-TX8, NI-TX9

Heating at 60° C. for 30 min and centrifugation to remove a large amount of precipitate. The supernatent was acidified to pH 4.6, frozen at −20° C. overnight, thawed and centrifuged to remove more precipitate.

(4) NI-TX5

Without dialysis or heating, the crude supernatant was directly acidified to pH 4.6, frozen at −20° C. overnight, thawed and centrifuged to remove more precipitate.

After the above pretreatment, the cell extract was pumped onto a 50 mL bed volume, S-sepharose fast flow, cation exchange column (Kabi-Pharmacia, Canada), equilibrated in buffer A. The xylanase was eluted with a 300 mL linear gradient of 0 to 0.3M NaCl in buffer A at a flow rate of 3 mL/min. The xylanase elutes at 100 to 150 mL of the gradient. The fractions are checked on SDS-PAGE, and those fractions having most of the xylanase were pooled, and concentrated by ultrafiltration using 3000 dalton molecular weight cutoff membranes (Amicon YM3). The concentrated material (5 mL) was then applied to a 1.5 cm×85 cm TSK-HW50S gel filtration column, equilibrated in 50 mM ammonium acetate pH 6. The xylanase eluted at a volume of 90 to 100 mL. These fractions were analyzed by SDS-PAGE, and the peaks pooled as pure xylanase. The protein was quantified using the extinction co-efficient at 280 nm. Typical purified yield from 10 g of cells was 25 mg of xylanase. All NI-TX and NI-BX xylanases have good solubility in the ammonium acetate buffer without glycerol.

(C) Standard assay for the measurement of enzymatic activity

The quantitative assay determined the number of reducing sugar ends generated from soluble xylan. The substrate for this assay was the fraction of birchwood xylan which dissolved in water from a 5% suspension of birchwood xylan (Sigma Chemical Co.). After removing the insoluble fraction, the supernatant was freeze dried and stored in a dessicator. The measurement of specific activity was performed as follows. Reaction mixtures containing 100 μL of 30 mg/mL xylan previously diluted in assay buffer (50 mM sodium citrate, pH 5.5 or the pH optimum of the tested xylanase), 150 μL assay buffer, 50 μL of enzyme diluted in assay buffer were incubated at 40° C. At various time intervals 50 μL portions were removed and the reaction stopped by diluting in 1 mL of 5 mM NaOH. The amount of reducing sugars was determined with the hydroxybenzoic acid hydrazide reagent (HBAH) (Lever, 1972, Analytical Biochem 47:273–279). A unit of enzyme activity was defined as that amount generating 1μmol reducing sugar in 1 minute at 40° C.

For the comparison between modified and the natural xylanases (Tables 4 and 5), the specific activities of the xylanases was normalized to the specific activity of the natural xylanase.

TABLE 4

Relative activity of NI-TX xylanases

| Xylanase | Relative activity % |
|---|---|
| natl TrX | 100* |
| TvX (3–190) | 102 |
| NI-TX1 | 98 |
| NI-TX2 | 92 |
| NI-TX5 | 95 |
| NI-TX6 | 99 |
| NI-TX7 | 90 |

*The data are normalized to the specific activity of the natural TrX of 770 U/mg.

TABLE 5

Relative activity of NI-BX xylanases

| Xylanase | Relative activity % |
|---|---|
| BcX | 100* |
| NI-BX1 | 92 |
| NI-BX3 | 89 |
| NI-BX6 | 92 |

*The data are normalized to the specific activity of BcX of 330 U/mg.

In both NI-TX (Table 4) and NI-BX xylanases (Table 5), the specific enzymatic activities of the modified xylanases at 40° C. are not significantly different from the natural xylanases.

EXAMPLE 4

Temperature/Activity Profiles of Modified Trichoderma Xylanases

This was a measure of the effect of temperature on the enzymatic activity of the xylanase in the hydrolysis of soluble xylan. The procedure was identical to the standard assay with changes in the incubation temperature and time. The enzymes (15 μg/mL) and soluble xylanase in 50 mM sodium citrate buffer of pH 5.5 were mixed and incubated in a circulating water bath at different temperatures. After 30 min, the amount of reducing sugars released from xylan was determined by HBAH and was calculated as a relative activity, with the value at 40° C. as 100%.

Figure 5:
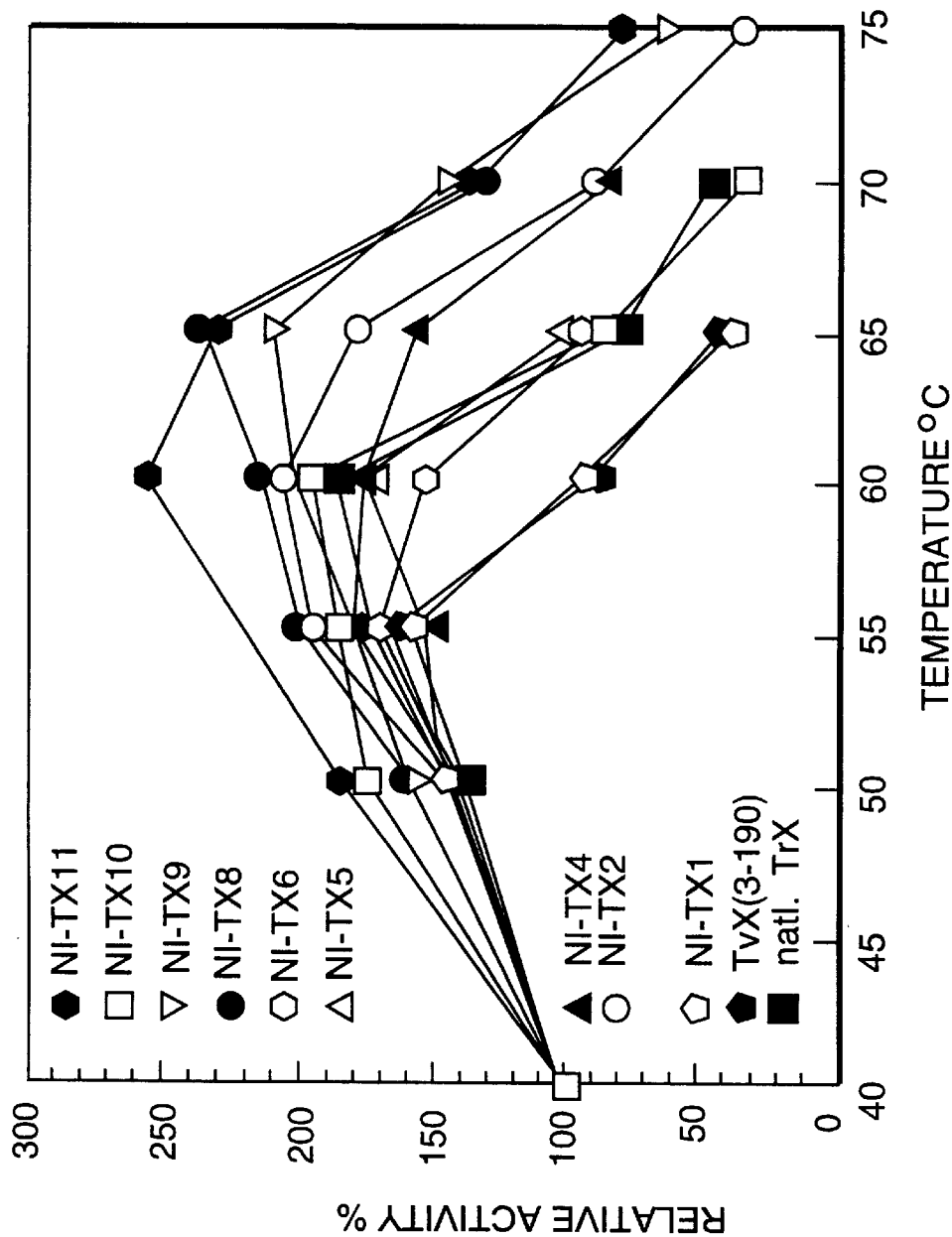
FIG. 5 shows the effect of temperature on the enzymatic activity of NI-TX mutant xylanases. Enzymatic activity was normalized to that at 40° C.

The effect of temperature on the hydrolysis of xylan is shown in FIG. 5. The E. coli-expressed TvX(3-190) showed much less activity at 55° C. or above than the natural TrX. As reported by Sung et al 1995, similarly low thermophilicity has been shown in the E. coli-expressed TrX.

The natural TrX was highly active up to 60° C. The advantage in thermotolerance of this enzyme over that expressed in E. coli is probably the result of posttranslational modifications in the Trichoderma host.

The mutant NI-TX1, with mutation Q162H, has an activity/temperature profile identical to that of TvX(3-190).

Substitution of the (1–29) region of NI-TX1 with the corresponding sequence of Tfx(1–29) and the N-terminus extension with the tetrapeptide ASHA at the (−4) to (−1) positions generated NI-TX2. If the effective temperature is defined as a temperature allowing 150% relative activity as at 40° C., this mutant showed a gain of 10° C. over TvX (3-190) or NI-TX1.

A mutant xylanase NI-TX3 with the substitution by Tfx (1–29) but without the N-terminus extension of residues ASHA at the (−4) to the (−1) positions as in NI-TX2, has a temperature/activity profile identical to the latter.

Another mutant NI-TX4 with a substitution of a shorter Tfx(10–29) sequence has a slightly lower thermophilicity than NI-TX2 and NI-TX3.

The chimeric xylanase NI-TX5, with a change of the tetrapeptide from Tfx at the (26–29) region showed a gain of 5° C. over TvX (3-190) or NI-TX1.

The mutant NI-TX6, with double mutations Y27M and N29L retained significant enzymatic activity up to 60° C. It showed the same temperature/activity profile as NI-TX5.

Another mutant NI-TX7 has the same thermophilicity as NI-TX2. NI-TX7 has the same amino acid sequence as NI-TX3 but with the N-terminus extension consisting of a tetrapeptide ASAR in the −4 to −1 positions. Although this mutant and NI-TX2 have shown that extension with these tetrapeptides has no significant effect on the temperature range of the chimeric Trichoderma xylanase, other N-terminal extensions have been explored.

NI-TX8 was synthesized and it showed a gain of 13° C. over TvX(3-190) or NI-TX1, and about 10° C. over natural TrX. It is of the same structure as NI-TX7 with an additional extension upstream of the N-terminus with the C. acetobutylicum xynB (23–31) sequence from the (−10) to (−2) positions.

A mutant NI-TX9 was constructed to test whether the C. acetobutylicum xynB (23–31) sequence in upstream extension of NI-TX8 can be replaced by a shorter tripeptide sequence GRR. This tripeptide has been identified in the study of NI-BX7 described later. The new mutant NI-TX9 of smaller size showed the same temperature/activity profile as NI-TX8.

This is the first report of enhancement of performance by an upstream extension to the N-terminus of a xylanase.

As for the identification of other residues contributing to the thermophilicity of the Family 11 xylanase, a mutant NI-TX10 was prepared, which was derived from NI-TX1 with two mutations N10H and N11D. The new mutant NI-TX10 showed a gain of 6° C. in its effective temperature as compared to its precursor NI-TX1.

Finally two mutant xylanases NI-TX11 and NI-TX12, derivatives of NI-TX1 with the triple mutation (N10H Y27M N29L) and the quadruple mutation (N10H N11D Y27M N29L) respectively, have been constructed. They were used to determine (i) the individual contribution of the mutations N10H and N11D, and (ii) their combined effect with two other advantageous mutations Y27M and N29L identified above. Both mutants NI-TX11 and NI-TX12 have shown identical temperature-activity profile with a gain of 13° C. in effective temperature. This result indicated that the N11D mutation has no effect on the thermophilicity of TrX. A conversion of the residues at position (1–4) in NI-TX11 to those of the wild type TrX yielded NI-TX13. The temperature-activity profile of both NI-TX11 and NI-TX13 remained identical.

This gain in the effective temperature for a relative activity of 150% by NI-TX11 or NI-TX13 (+130C) is greater than the theoretical sum of the gains by individual mutations N10H (+6° C., in NI-TX11) and Y27M/N29L (+4° C., in NI-TX2). This improvement is also greater than any gain via a direct substitution with any natural TfX sequence which may harbor the triple mutation, as shown in the chimeric mutants NI-TX2 (+10° C.), NI-TX3 (+10° C.) and NI-TX4 (+9° C.). Furthermore, the triple mutation of 3 residues in NI-TX11 or NI-TX13 represents a much smaller modification in TrX, as compared to the substitution with the TfX sequences of 31–20 residues as in the chimeric enzymes, and this may indirectly minimize other unwanted changes in the general characteristics of the Trichoderma xylanase.

EXAMPLE 5

Temperature/Activity Profiles of Modified Bacillus Xylanases

Figure 6:
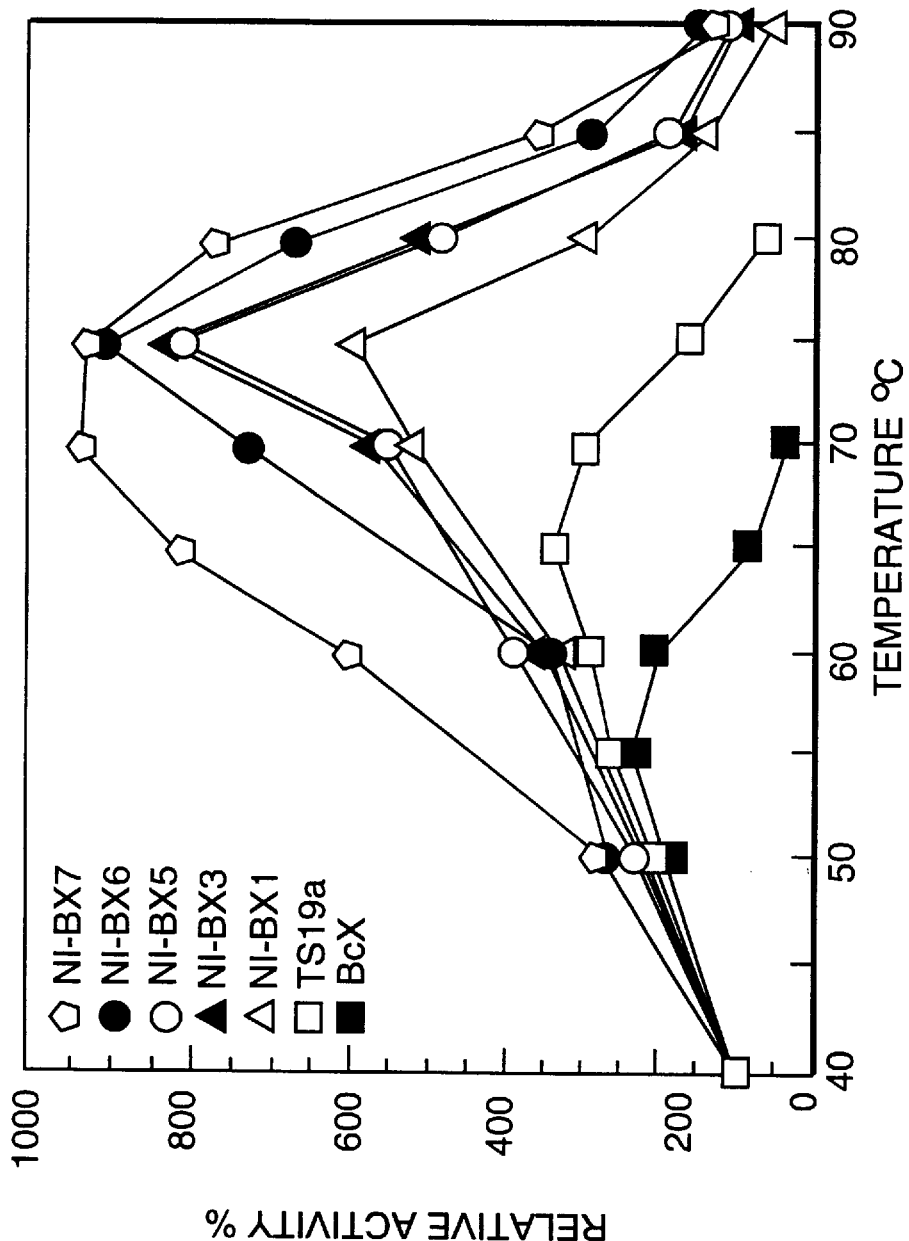
FIG. 6 shows the effect of temperature on the enzymatic activity of NI-BX mutant xylanases. Enzymatic activity was normalized to that at 400° C. The profile of BcX mutant TS19a of Campbell, et al is also presented.

The assay protocol was generally identical to the one for the NI-TX xylanases in Example 4. The effect of temperature on the hydrolysis of soluble xylan in 50 mM sodium citrate buffer of pH 5.5 by the NI-BX xylanases is shown in FIG. 6.

The natural BcX was active up to 60° C.

The mutant NI-BX1, with a Tfx(1–31) sequence replacing the BcX(1–22) sequence in its N-terminus, has high activity up to around 82° C. As discussed in the NI-TX section, we can define the effective temperature as a temperature allowing 150% relative activity as in 40° C. In this case, the gain in the thermophilicity of N-BX1 would be about 22° C. The mutant NI-BX2, without the extra residues ASHA in the (−4) to the (−1) position as in NI-BX1, showed the same temperature/activity profile.

Further modification by the insertion of an Arg residues at the (−1) position in NI-BX3 and NI-BX5 has improved the thermophilicity by 2.5° C. over NI-BX1 and NI-BX2.

The same gain has also been observed in NI-BX4 which has another basic residue Lys at the (−1) position. Replacement with acidic residue Glu or Asp causes a loss of around 10° C. in maximum temperature (data not shown). Therefore, these results have demonstrated the contribution to the thermotolerance of the extension at the (−1) position with basic amino acids (Arg, Lys), as opposed to the presence of neutral (His) and acidic (Asp, Glu) residues.

The mutant NI-BX6 showed a gain of 2.5° C. over NI-BX3 or 5° C. over NI-BX1. Thus the thermophilicity can be further improved via extension of the N-terminus through the addition of the *C. acetobutylicum* xynB (23–29) sequence from the (–10) to (–4) positions, Gly at the (–3) position and Arg in both (–2) and (–1) positions.

A mutant NI-BX7 was constructed to test whether the *C. acetobutylicum* xynB (23–31) sequence in upstream extension of NI-BX6 can be replaced by a shorter tripeptide sequence GRR. Although both NI-BX6 and NI-BX7 seemed to have identical effective temperature or top temperature limit, the latter mutant of smaller size showed a wider temperature range for enzymatic activity than the former. As described above in the mutant NI-TX9, the same tripeptide was also successful in elevating the effective temperature of the Trichoderma xylanase, without using the CaX sequence.

In summary, the modifications which have successfully increased the thermophilicity of the fungal Trichoderma xylanase, are generally applicable in the bacterial *Bacillus circulans* xylanase.

EXAMPLE 6

Comparison of the Thermophilicity of the NI-BX Xylanases With the Campbell, et al Prior Art.

The best improved *Bacillus circulans* (BcX) mutant TS19a of the Campbell et al. prior art had modifications to amino acids 3,4,8, and 22 (according to the BcX numbering system). This modified xylanase was compared with the NI-BX xylanases using the same protocols described above, with the results shown in FIG. 6. The temperature optima of the NI-BX xylanases are 8°–14° C. higher than that of TS19a. In addition, at optimum temperature the NI-BX6 and NI-BX7 xylanases of the present invention have 3-fold higher activity than that of Campbell, et al. This set of results demonstrates far superior performance of modified xylanases made by the present invention than with those of Campbell, et al.

EXAMPLE 7

Comparison of the Thermophilicity or NI-BX6 and NI-BX7 With the Natural Clostridium and T. Fusca Xylanases The N-terminal domain of the mutant xylanase NI-BX6 included an extension by a short sequence from the *Clostridium acetobutylicum* xynB (CaX). The N-terminal domain of the mutant xylanase NI-BX7 included an extension by the tripeptide GRR. NI-BX6 and NI-BX7 had a sequence of amino acids and substituted by a short sequence from a thermostable xylanase TfxA of *Thermomonospora fusca*. The thermophilicity of NI-BX6 and NI-BX7 were assessed in comparison with published data on these natural Thermomonospora and Clostridium xylanases.

The mutants NI-BX6 and NI-BX7, with high activity up to 85° C., are superior to the *Clostridium acetobutylicum* xynB (CaX) with a much lower temperature optimum of 43° C. (Zappe et al. 1987, Zappe et al. 1990).

There was no data available on the temperature profile of *T. fusca* xylanase TfxA. The published data on the thermophilicity of the fermentation supernatant of *T. fusca* (Casimir-Schenkel et al. 1992) was available. This supernatant includes six xylanases, of which TfXA is one. The effect of temperature on the activity of NI-BX6 and NI-BX7 was measured according to the protocol described for the fermentation supernatant of *T. fusca* (Casimir-Schenkel et al. 1992). This included the addition of the mutant xylanase to xylan in 50 mM sodium phosphate buffer (pH 7) and incubation at 70, 80 and 90° C. for exactly 10 min.

The data shows that the chimeric Bacillus xylanase demonstrated greater thermophilicity than the *T. fusca* xylanase supernatant, and hence is very likely greater than TfXA (Table 6).

This example demonstrates the surprising result that insertion of the short sequences in the chimeric modifications can increase the thermotolerance of the xylanase well beyond that of the thermophilic xylanases that are the source of the short sequences.

TABLE 6

Temperature profile of relative enzymatic activity at pH 7.0

| Temperature °C. | Relative activity (% of maximum)*- | | |
|---|---|---|---|
| | NI-BX6 | NI-BX7 supernatan t** | T. fisca |
| 70 | 100 | 100 | 100 |
| 80 | 96 | 110 | 58 |
| 90 | 36 | 20 | 11 |

*The enzymatic activity at 70° C. was calculated as 100%.
**Published data by Casimir-Schenkel et al. 1992 which is incorporated herein by reference.

In addition to higher temperature for enzymatic activity, some new mutants have also gained greater enzymatic activity, as compared to the wild-type enzyme. The relative activities of some NI-BX xylanases (NI-BX6, NI-BX7) at their respective temperature optima (75° C.) were 4-fold as that of the wild type BcX (55° C.) (see FIG. 6).

In summary, the modifications which have successfully increased the thermophilicity of the fungal Trichoderma xylanase, are generally applicable in the bacterial *Bacillus circulars* xylanase.

EXAMPLE 8 pH/Activity Profiles of Modified Trichoderma Xylanases

This was a measure of the effect of different pH on the enzymatic activity of the xylanase in the hydrolysis of soluble xylan. The procedure was identical to the standard assay with changes in the incubation temperature and time. The Trichoderma enzymes (15 µg/mL) and soluble xylanase in 50 mM sodium citrate buffers of pH 4–8 were incubated together at 65° C. After 30 min, the amount of reducing sugars released from xylan was determined by HBAH and was expressed as a relative activity, with the value at pH optimum as 100%.

Figure 7:
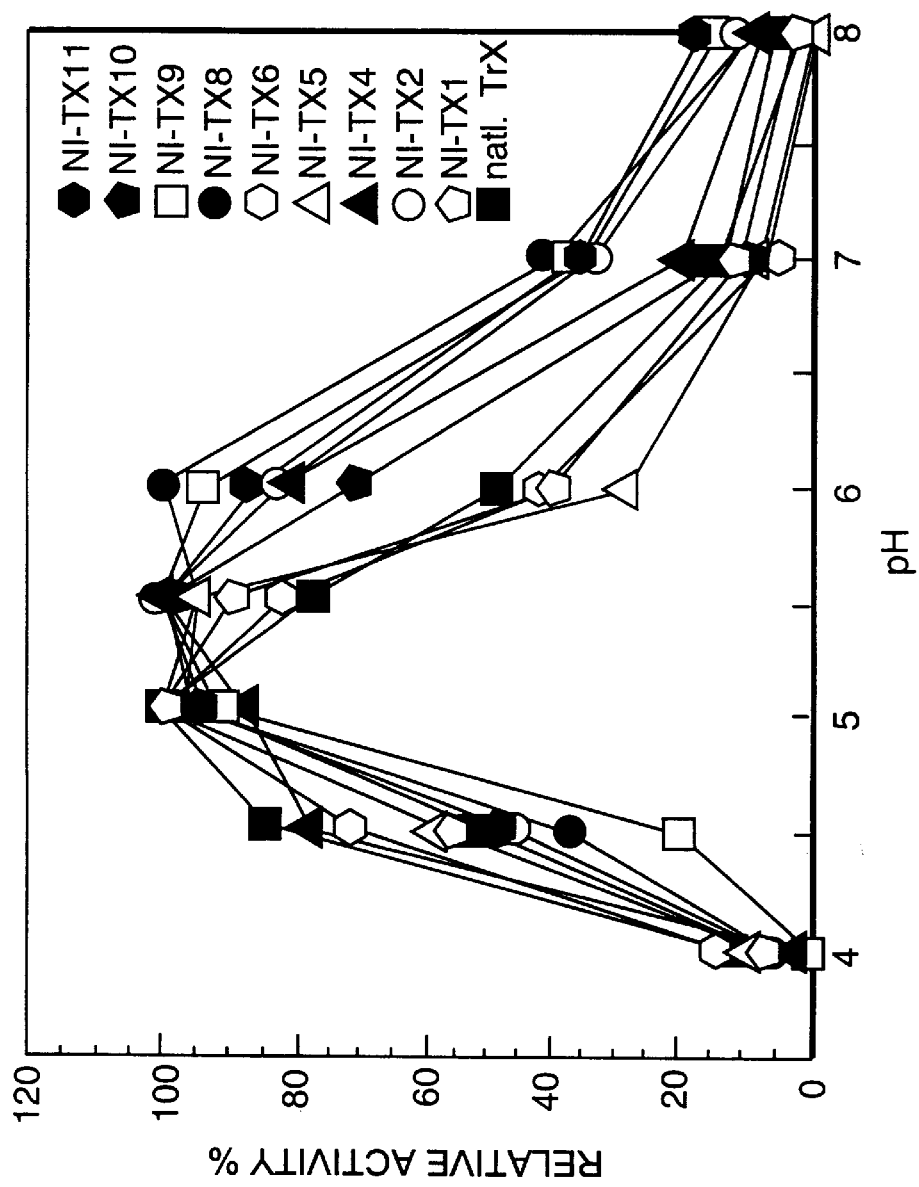
FIG. 7 shows the effect of pH on the enzymatic activity of NI-TX modified Trichoderma xylanases at 65° C. The data are normalized to the maximum enzymatic activity.

The effect of pH on the enzymatic activity of different NI-TX xylanases was shown in FIG. 7.

The natural TrX, NI-TX1, NI-TX5, NI-TX6 showed the same pH/activity profile, with high activity up to pH 5.5 and a significant loss of activity at pH 6.

The substitution with Tfx(1–29) in the mutants NI-TX2, NI-TX3 and NI-TX8 results in full activity up to pH 6.0, and significant activity at pH 7. This represents a gain of 1 pH unit over the natural TrX. The mutant NI-TX9 demonstrated a pH-activity profile identical to NI-TX8, thus indicating the upstream CaX sequence can be replaced by the tripeptide GRR.

The analogue NI-TX10 with the double mutation (N10H N11D) showed a gain of 0.5 pH unit in its upper limit for activity as compared to its precursor NI-TX1. NI-TX11, NI-TX12 and NI-TX13 showed a gain of 0.6 pH unit.

EXAMPLE 9 pH Profiles of Modified Bacillus Xylanases

The test procedure was identical to the protocol for the modified Trichoderma xylanases in Example 8. The *Bacillus*

Figure 8:
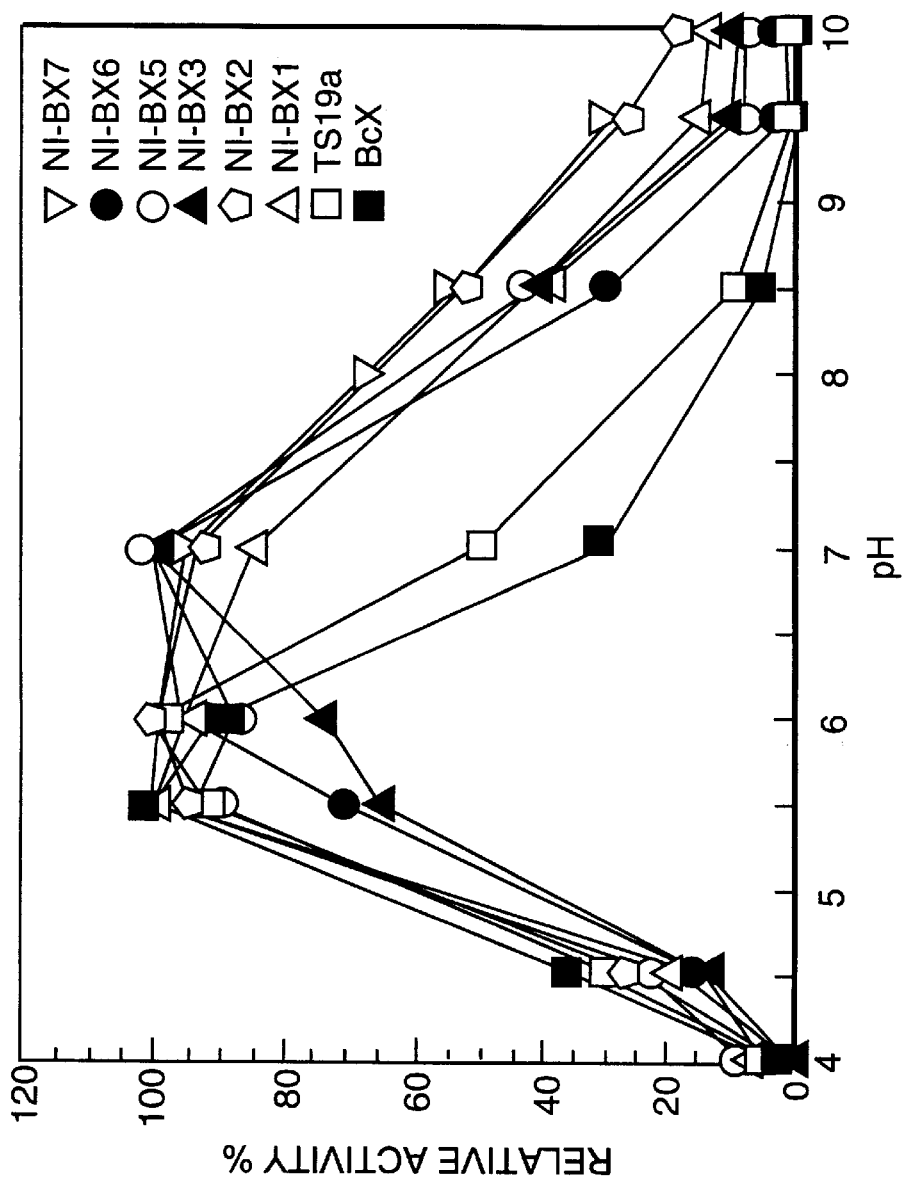
FIG. 8 shows the effect of pH on the enzymatic activity of NI-BX modified xylanases at 65° C. The profile of BcX mutant TS19a is also presented. The data are normalized to the maximum enzymatic activity.

*circulans* xylanases were incubated with soluble xylan at 65° C. in sodium citrate (pH 4–8) and sodium borate buffers (pH 9.5 and 10). As shown in FIG. 8, the natural BcX is fully active up to pH 6.0.

The substitution of longer sequence with Tfx(1–33) in the mutants NI-BX1, NI-BX2, NI-BX3, NI-BX5, NI-BX6, and NI-BX7 has extended the activity to above pH 7.0 (FIG. 8). This represents a gain of 1.5–2 pH units over BcX.

EXAMPLE 10

Comparison of the pH/Activity Profile of the Modified Bacillus Xylanases With That of Campbell, et al The pH range of the best xylanase TS19a of the prior art of Campbell et al. was measured and compared with the NI-BX xylanase according to the protocol described in Example 8. The results are shown in FIG. 8. The pH optima of the NI-BX xylanases are 1–1.5 unit higher than that of TS19a, while TS19a itself has only a minor improvement (0.5 pH unit) over natural BcX. This result demonstrates the superior performance of the xylanases of the present invention relative to those of Campbell, et al.

EXAMPLE 11

Comparison of the pH/Activity Profiles of the Modidied Bacillus Xylanases With the Natural Xylanases of Clostridium Acetpbitulicum and *T. Fusca*.

Since the N-terminal domain of the NI-BX xylanases was constituted by short sequences from the *Clostridium acetobutylicum* xynB (CaX) and the xylanase TfxA of *Thermomonospora fusca*, the pH ranges of the modified Bacillus xylanases was compared to the published data of these two natural xylanases.

The NI-BX mutant xylanases, with maximal activity up to pH 7 at 65° C. (FIG. 8), has a higher maximum pH than the *Clostridium acetobutylicum* xynB (CaX) with a pH optimum of 6.0 at 43° C. (Zappe et al. 1987, Zappe et al. 1990).

Figure 9:
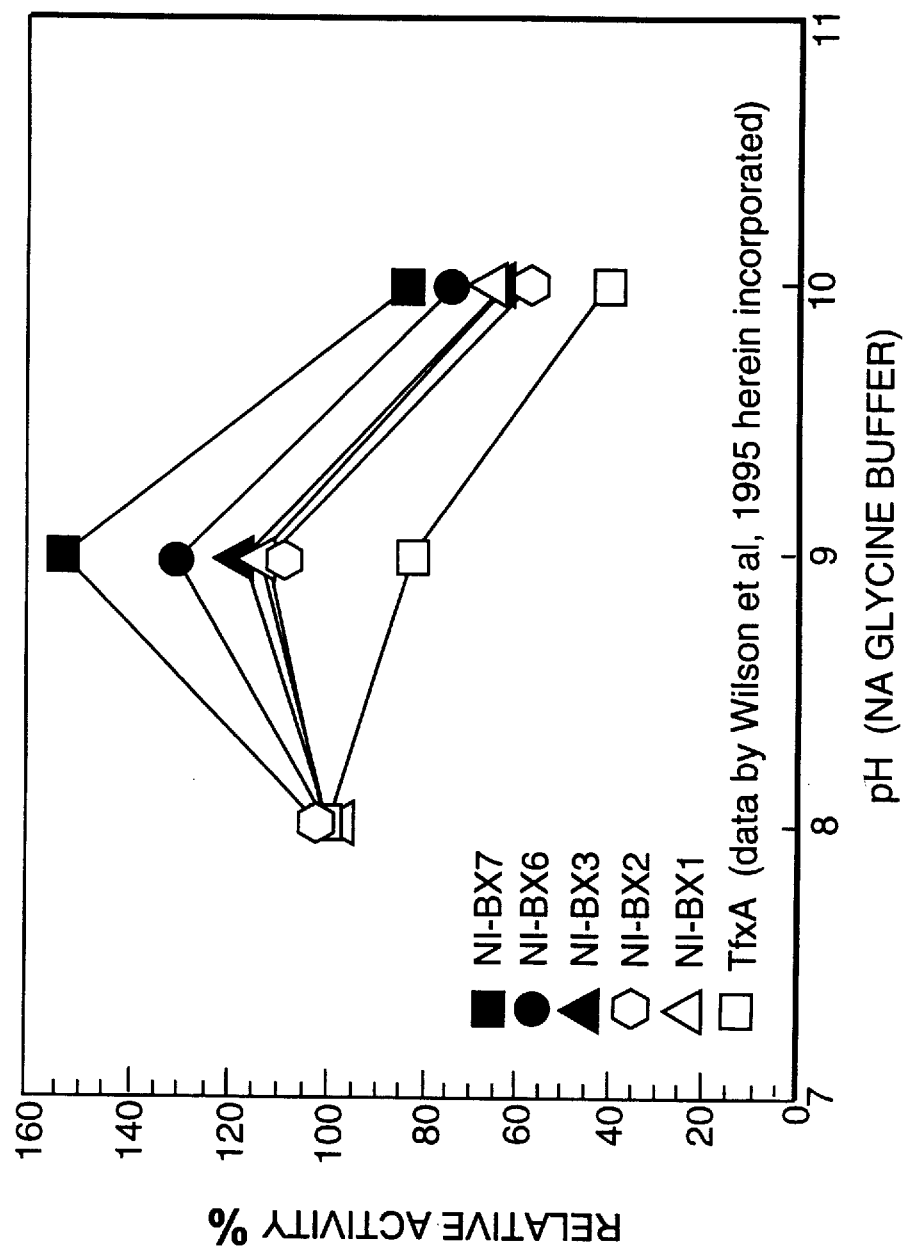
FIG. 9 shows the effect of pH on the enzymatic activity of the modified Bacillus xylanases at 50° C. Data on TfxA published by Wilson et al (PCT, 1995) is included. For the purpose of comparison with TfxA, the enzymatic activity of all modified Bacillus xylanases was normalized to the pH 8 results.

As for the *T. fusca* xylanase TfxA, its pH range has already been disclosed (Wilson et al, PCT/1995). For comparative study, the effect of pH on the enzymatic activity of NI-BX xylanases was therefore determined according to the protocol as described for TfxA (Wilson et al, PCT/1995). This included the addition of the xylanase to xylan in 0.05M sodium glycine buffers of pH 8–10 and incubation at 50° C. for 30 min. As shown in FIG. 9, the Bacillus xylanases NI-BX1, NI-BX2, NI-BX3, NI-BX6, and NI-BX7 all showed pH optima of 9 while the pH optimum of TfxA was 8.

This example shows the surprising result that the xylanases of the present invention have a higher pH range than either of the xylanases used to donate short sequences of amino acids.

EXAMPLE 12

Thermostability of Modified Trichoderma Xylanases

This was a measure of the tolerance of xylanase to storage at a set temperature, without any xylan present. The following parameters were generally used in both NI-TX and NI-BX xylanases. The xylanase (150 μg/mL) in assay buffer (50 mM sodium citrate, pH 5.5 or 4.5) was incubated at a set temperature. Aliquots were removed at set intervals. After cooling to 20° C., the residual enzymatic activity of the heated samples was determined via the HBAH assay of Example 3 at 40° C. The enzymatic activity was normalized as a percentage of the activity of the "0 min" aliquot.

Figure 10:
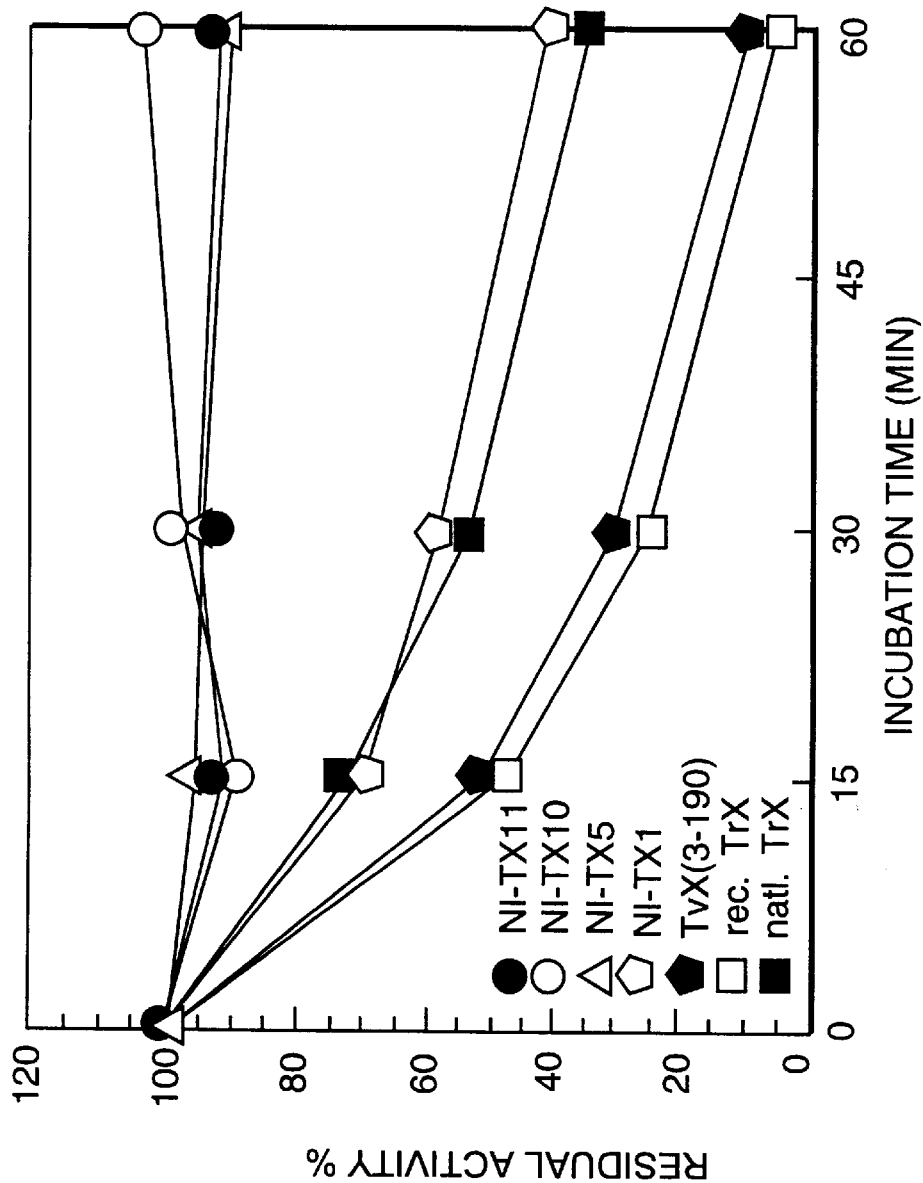
FIG. 10 shows the thermostability of modified Trichoderma xylanases NI-TX1, NI-TX5, NI-TX10, NI-TX11, TvX(3-190) and the natural TrX at 53° C. Enzymatic activity was normalized to that at 0 min of incubation.

FIG. 10 shows that chimeric xylanase NI-TX5, NI-TX10, and NI-TX11 have an improved storage stability at 53° C. over the natural TrX. The replacement of the (26–29) region by the SMEL tetrapeptide sequence of Tfx in the case of NI-TX5 has allowed it to retain all of its enzymatic activity after incubation for 60 min.

NI-TX1, TvX(3-190), and Trx expressed in *E. coli* show no improvement in thermostability over the natural TrX.

Figure 11:
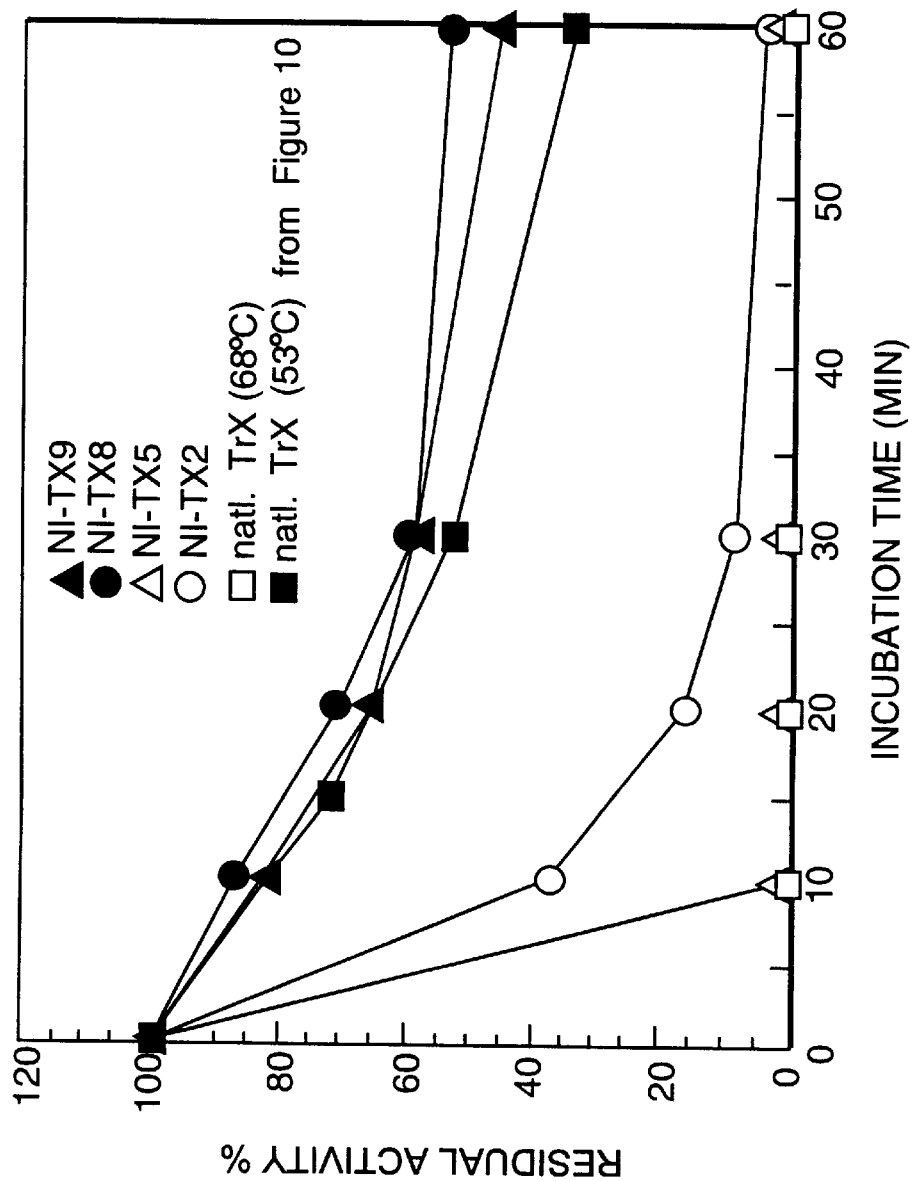
FIG. 11 shows the thermostability of chimeric xylanases NI-TX2, NI-TX5, NI-TX8, NI-TX9 and natural TrX at 68° C. The profile of natural TrX at 53° C. was also included for comparison. Enzymatic activity was normalized to that at 0 min of incubation.

At a higher incubation temperature of 68° C., the natural TrX, NI-TX1 and NI-TX5 lost all enzymatic activity in less than 10 min (FIG. 11).

At the same temperature, the chimeric xylanase NI-TX2 has retained 40% of enzymatic activity after 10 min.

The chimeric xylanase NI-TX8 has kept 55% of its activity after 60 min, thus representing a tolerance of storage temperature which is about 15° C. higher than that by the natural TrX.

In summary, the chimeric modifications in NI-TX2, NI-TX8, and NI-TX9 ie. the replacement of the (1–29) region of the Trichoderma xylanase by the Tfx(1–29) sequence, the upstream extension with either the *C. acetobutylicum* xynB (23–31) sequence from the (–10) to (–2) positions and Arg at the (–1) position, or the tripeptide GRR have further increased the thermostability.

EXAMPLE 13

Thermostability of Modified Bacillus Xylanases

Figure 12:
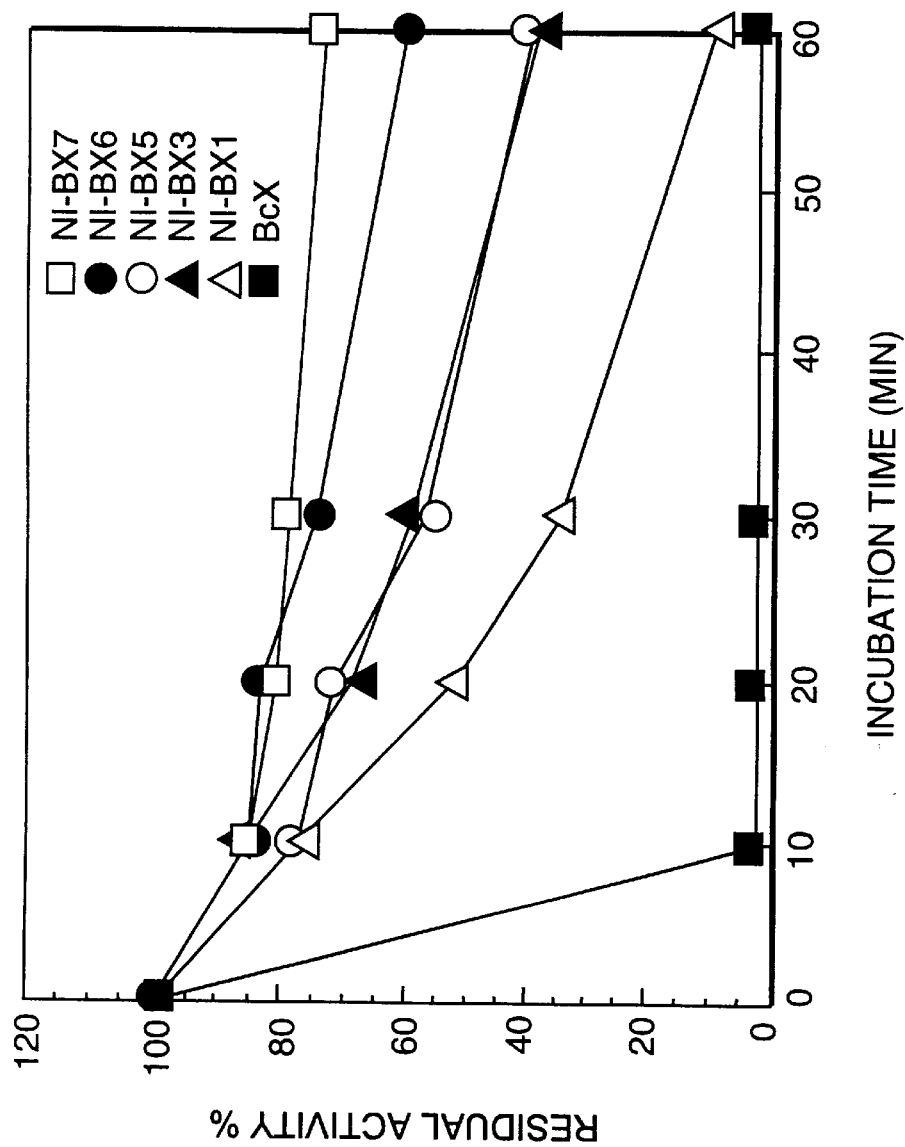
FIG. 12 shows the thermostability of NI-BX and BcX at 70° C. Enzymatic activity was normalized to that at 0 min of incubation.

The NI-BX modified Bacillus xylanases and BcX were incubated at 70° C. and pH 5.5 (FIG. 12). The natural xylanase BcX lost all enzymatic activity as expected in less than 10 min. In contrast, the mutant xylanase NI-BX1 retained most of the activity after 20 to 30 min. This indicated that the thermostability of the *Bacillus circulans* xylanase can be increased via the replacement of the BcX (1–22) sequence by the Tfx(1–31) sequence. Further increase in thermostability among NI-BX3, NI-BX5, NI-BX6, and NI-BX7 was achieved by the extension of the N-terminus through either the addition of the *C. acetobutylicum* xynB (23–29) sequence from the (–10) to (–4) positions, Gly at the (–3) position and Arg in both (–2) and (–1) positions or the tripeptide GRR. For NI-BX6 and NI-BX7, the gain in thermostability is about 15° C. relative to the natural enzyme BcX. Thus the modifications that successfully increase the thermostability of the fungal Trichoderma xylanase are generally applicable in the *Bacillus circulans* xylanase.

EXAMPLE 14

Evaluation of Performance of Modified Trichoderma Xylanases in Treatment of Pulp The assay described above in the Examples 3 through 13 involves hydrolysis of soluble xylan and this procedure has been successful in the identification of thermophilic modified xylanases in the NI-TX and NI-BX series. However, in the pretreatment of pulp in the bleaching process, xylanase would interact with the insoluble xylan in pulp. It is therefore important to confirm that the performance improvements identified using the soluble xylan substrate would be observed in the treatment of pulp. Therefore, the performance of the modified xylanases was evaluated in the treatment of brownstock pulp prior to bleaching.

Samples of natural and modified enzymes were sent to Iogen Corporation of Ottawa, Canada for testing on pulp. Iogen manufactures and supplies xylanase enzymes to the pulp industry and has developed tests to assess the performance of xylanase enzymes in treating pulp. The test involves adding the enzymes to pulp for a specified period and then measuring the effect of the enzyme on the subsequent bleachability of the pulp. The test were carried out using a commercial softwood Kraft pulp of Kappa number 25.6.

Figure 13:
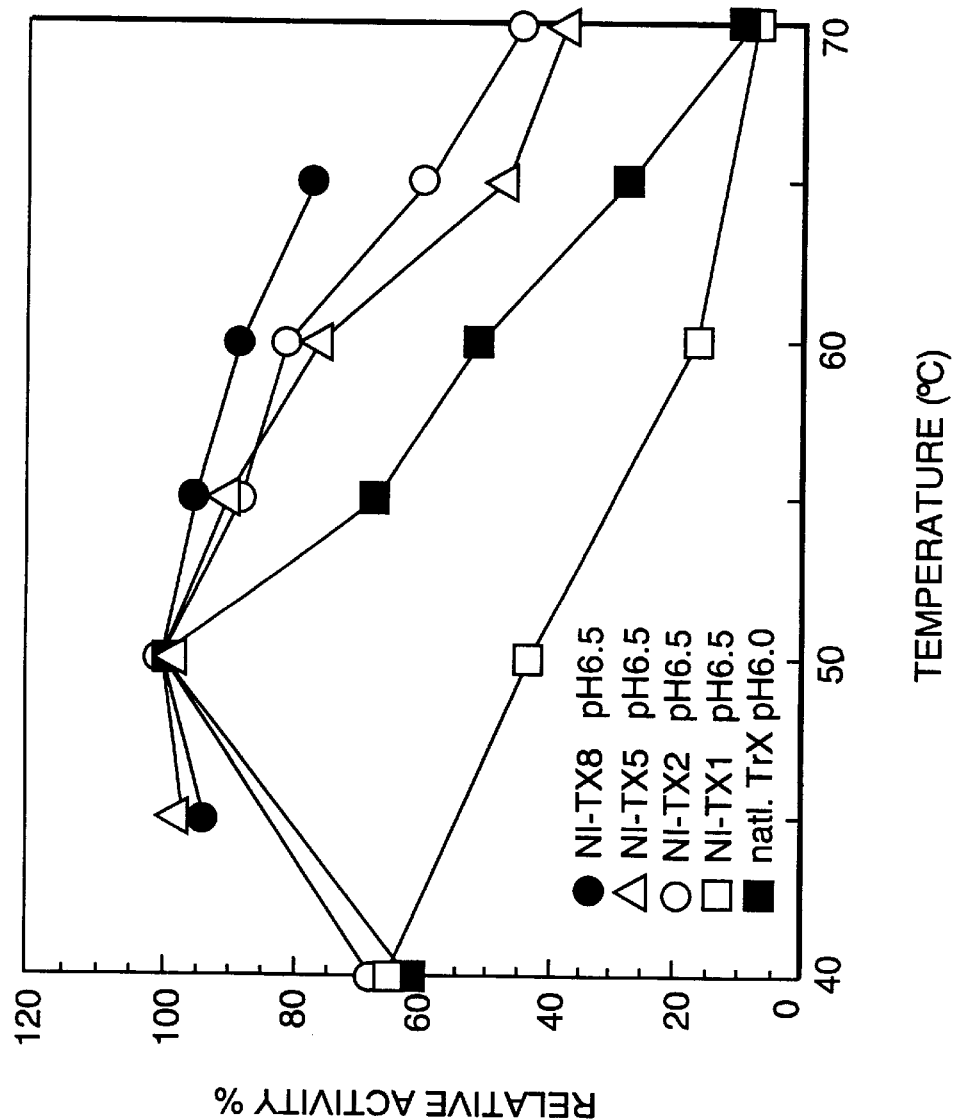
FIG. 13 shows the effect of temperature on the performance of NI-TX xylanase, recombinant and natural TrX in enhancing the bleaching of pulp (tests carried out by Iogen Corporation).

The results of the Iogen pulp testing of Trichoderma xylanases is shown in FIG. 13. At pH 6.0, the optimum pH for the natural TrX in treating pulp, good performance was achieved up to 52° C. The natural TrX was not active on pulp at pH 6.5.

The E. coli-expressed NI-TX1 with a single point mutation Q162H was ineffective on pulp at temperatures higher than 40° C. By contrast, the mutants NI-TX5, NI-TX2 and NI-TX8 could function up to 60, 61, and 65° C. respectively at pH 6.5.

Although the absolute temperatures tolerated by the enzymes are lower on pulp than in the hydrolysis of soluble xylan, the improvements by the modified xylanases in temperature (+8 to 13° C.) and pH (+0.5 unit) in the treatment of pulp were consistent with the gains in their thermophilicity and alkalophilicity in xylan hydrolysis described in Examples 4 and 8.

The temperature and pH ranges tolerated by the enzymes in pulp treatment is encouraging, based on these preliminary tests. Much more extensive testing of temperature and pH range using different pulps and treatment techniques would likely increase the range of conditions in which the modified xylanases are effective on pulp.

EXAMPLE 15

Evaluation of Performance of Modified Bacillus Xylanases in Treatment of Pulp

Figure 14:
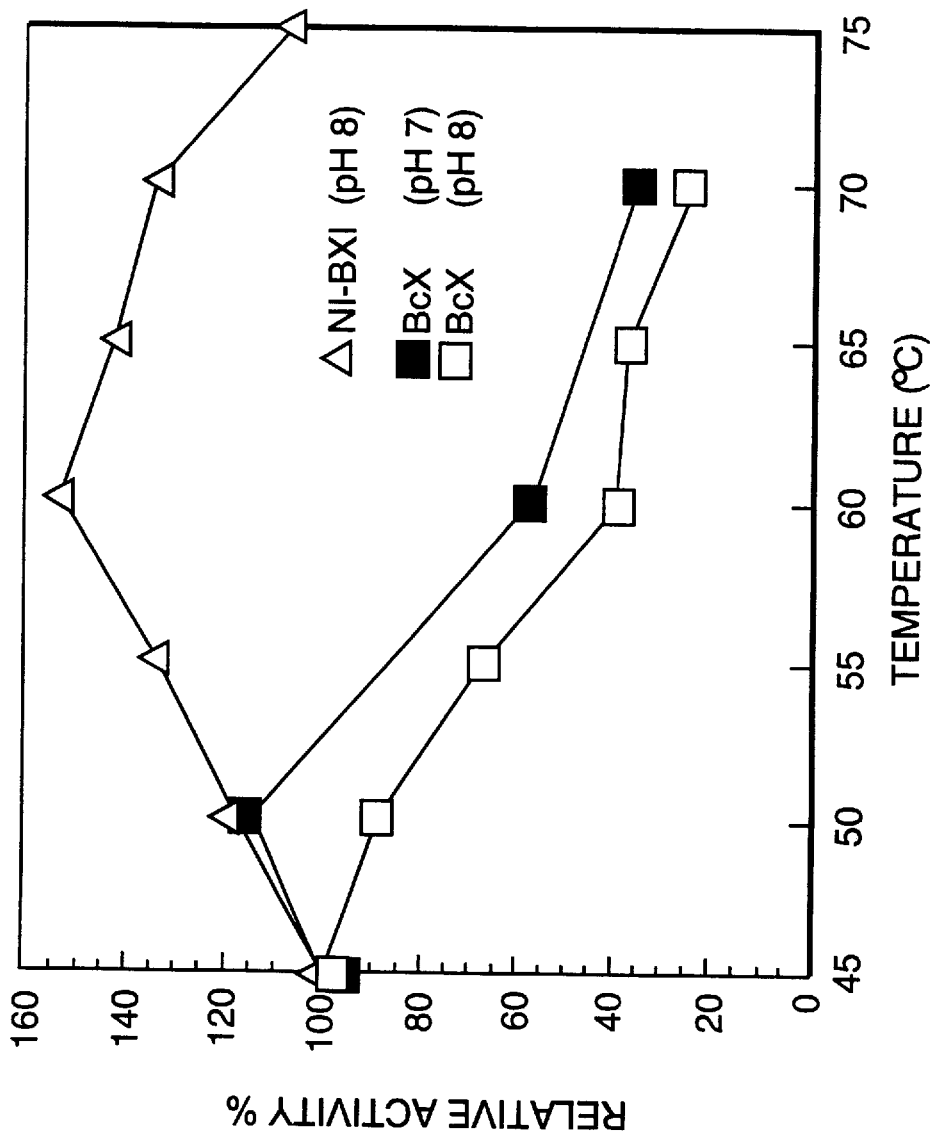
FIG. 14 shows the effect of temperature on the performance of NI-BX1 and wild-type BcX in enhancing the bleaching of pulp (tests carried out by Iogen Corporation).

The B. circulans xylanases were also tested in the treatment of pulp by Iogen Corporation (FIG. 14).

At pH 8.0, the natural BcX showed poor performance at temperatures higher than 400° C. When the pH was lowered to 7, BcX was only effective up to 50° C.

By contrast, the mutant NI-BX1 was active up to 75° C. at pH 8.0.

Although the absolute temperature tolerated by the NI-BX1 enzyme is lower on pulp than in the hydrolysis of soluble xylan, the improvements by the modified xylanase in temperature (+28° C.) and pH (+1 unit) in the treatment of pulp were consistent with the gains in their temperature tolerance and pH range in xylan hydrolysis described in Examples 5 and 9.

The temperature and pH ranges tolerated by the enzymes in pulp treatment is encouraging, based on these preliminary tests. Much more extensive testing of temperature and pH range using different pulps and treatment techniques would likely increase the range of conditions in which the modified xylanases are effective on pulp.

REFERENCES

Arase, A., Yomo, T., Urabe, I., Hata, Y., Katsube, Y. and Okada, H. (1993) FEBS Lett. 316:123–127.

Casimir-Schenkel, J., Davis, S., Fiechter, A., Gysin, B., Murray, E., Perrolaz, J.-J. and Zimmermann, W. European Patent application no. 91810652.7, published on 04.03.92. Publication no. 0 473 545 A2.

Campbell, R. L., Rose, D. R., Sung, W. L., Yaguchi, M. and Wakarchuk, W. U.S. Pat. No. 5,405,769 issued on Apr. 11, 1995.

Campbell, R. L., Wakarchuk, W. W., Sung, W. L., Yaguchi, M., Rose, D. R., Ishikawa, K. PCT publication No. WO 94/24270, published Oct. 27, 1994.

Fontes, C. M. G. A., Hazelwood, G. P., Morag, E., Hall, J., Hirst, B. H., and Gilbert, H. J. (1995) Biochem. J. 307:151–158.

Gilkes, et al (1991). Microbiol. Review 55:303–315.

Irwin, D., Jung, E. D. and Wilson, D. B. (1994) Appl. Environ. Microbiol. 60:763–770.

Lever, M. (1972) Analytical Biochemistry 47:273–279.

Lüthi, E., Jasmat, N. B., and Bergquist, P. L. (1990) Appl. Environ. Microbiol. 56:2677–2683.

Mathrani, I. M. and Ahring, B. K. (1992). Appl. Microbiol. Biotechnol. 38:23–27.

Nissen, A. M., Anker, L., Munk, N., Lange, N. K. in Xylans and Xylanases, edited by J. Visser, G. Beldman, M. A. Kustrers-van-Someran, and A. G. J. Voragen, published by Elsevier, Amsterdam, 1992, p. 325–337.

Sakka, K., Kojima Y., Kondo, T., Karita, S., Ohmiya, K. and Shimada, K. (1993) Biosci. Biotech. Biochem. 57:273–277.

Simpson, H. D., Haufler, U. R., and Daniel, R. M. (1991) Biochem. J. (1991) 277:413–417.

Sung. W. L. Yao. F.-L., Zahab, D. M. and Narang, S. A. (1986) Proc. Natl. Acad. Sci. USA 83:561–565.

Sung, W. L., Luk, C. K., Zahab, D. M. and Wakarchuk, W. (1993) Protein Expression Purif. 4:200–206.

Sung, W. L., Luk, C. K., Chan, B., Wakarchuk, W., Yaguchi, M., Campbell, R., Willick, G., Ishikawa, K. and Zahab, D. M. (1995) Biochem. Cell. Biol. 73:253–259.

Tolan et al (1995) Pulp and Paper Canada, December 1995.

Wakarchuk, W. W., Campbell, R. L., Sung, W. L., Davoodi, J., and Yaguchi, M.(1994). Protein Science 3:467–475.

Wakarchuck W. W., Sung, W. L., Campbell, R. L., Cunningham, A., Watson, D. C. and Yaguchi, M. (1994) Protein Engineering 7:1379–1386.

Wilson, D. B., Jung, E. D., Changas, G. S., Irvin, D. C. PCT international publication on 11 May 1995. Publication No. WO 95/12668.

Winterhalter C. and Liebl, W. (1995) Appl. Environ. Bicrobiol. 61:1810–1815.

Zappe, H., Jones, W. A., and Woods, D. R. (1987) Appl. Microbiol. Biotechnol. 27:57–63.

Zappe, H., Jones, W. A., and Woods, D. R. (1990) Nucleic Acids Res. 18:2179.

We claim:

1. A method of improving the bleachability of wood pulp, the method comprising treating the pulp with a Family 11 xylanase enzyme selected from the group consisting of the Family 11 xylanases of Trichoderma, Aspergillus, Streptomyces, and Bacillus having the amino acid tyrosine or phenylalanine in position 14 and having at least 8 amino acid residues in a N-terminus upstream from position 10, as determined by the amino acid numbering of *Trichoderma reesei* xylanase II or the corresponding position in the other xylanases when the amino acids are aligned, said xylanase enzyme having been modified to exhibit enhanced thermophilicity, alkalophilicity, or thermostability with respect to a wild type enzyme of said xylanase enzyme by having a substitution mutation at position 10 relative to a wild type enzyme from which said xylanase enzyme is derived for approximately 5 minutes to three hours, at a temperature between approximately 55° C. to 75° C.

2. The method of claim 1 wherein the xylanase treatment is carried out at pH 7.5 to 9.0.

3. A method of improving the bleachability of wood pulp, the method comprising treating the pulp with a Family 11 xylanase enzyme selected from the group consisting of the Family 11 xylanases of Trichoderma, Aspergillus, Streptomyces, and Bacillus having the amino acid tyrosine or phenylalanine in position 14, as determined by the amino acid numbering of *Trichoderma reesei* xylanase II or the corresponding position in the other xylanases when the amino acids are aligned, said xylanase enzyme having been modified to exhibit enhanced thermophilicity, alkalophilicity, or thermostability relative to a wild type enzyme of said xylanase enzyme by substituting a sequence of amino acids in a N-terminal region of said xylanase enzyme with that of a corresponding aligned sequence of amino acids from *Thermomonospora fusca* xylanase A to form a chimeric xylanase, and an upstream extension of the N-terminus of the chimeric xylanase with the addition of from 0 to 10 amino acids for 5 minutes to three hours at 55° C. to 75° C.

4. The method of claim 3 wherein the xylanase treatment is carried out at pH 7.5 to 9.0.

5. A method of improving the bleachability of wood pulp, the method comprising treating the pulp with a Family 11 xylanase enzyme selected from the group consisting of the Family 11 xylanases of Trichoderma, Aspergillus, Streptomyces, and Bacillus having the amino acid tyrosine or phenylalanine in position 14 and having at least 8 amino acid residues in a N-terminus upstream from position 10, as determined by the amino acid numbering of *Trichoderma reesei* xylanase II or the corresponding position in the other xylanases when the amino acids are aligned, said xylanase enzyme having been modified to exhibit enhanced thermophilicity, alkalophilicity, or thermostability with respect to a wild type enzyme of said xylanase enzyme by having a substitution mutation at position 10 relative to a wild type enzyme from which said xylanase enzyme is derived, wherein the Family 11 xylanase is selected from the group consisting of *Trichoderma reesei* xylanase I, *Trichoderma reesei* xylanase II, Trichoderma harzianum Xylanase, *Trichoderma viride* Xylanase, *Streptomyces lividans* xylanase B, and *Streptomyces lividans* xylanase C, for approximately 5 minutes to three hours, at a temperature between approximately 55° C. to 75° C.

6. The method of claim 5 wherein the xylanase treatment is carried out at pH 7.5 to 9.0.

7. A method of improving the bleachability of wood pulp, the method comprising treating the pulp with a Family 11 xylanase enzyme selected from the group consisting of the Family 11 xylanases of Trichoderma, Aspergillus, Streptomyces, and Bacillus having the amino acid tyrosine or phenylalanine in position 14, as determined by the amino acid numbering of *Trichoderma reesei* xylanase II or the corresponding position in the other xylanases when the amino acids are aligned, said xylanase enzyme having been modified to exhibit enhanced thermophilicity, alkalophilicity, or thermostability relative to a wild type enzyme of said xylanase enzyme by substituting a sequence of amino acids in a N-terminal region of said xylanase enzyme with that of a corresponding aligned sequence of amino acids from *Thermomonospora fusca* xylanase A to form a chimeric xylanase, and an upstream extension of the N-terminus of the chimeric xylanase with the addition of from 0 to 10 amino acids, wherein the Family 11 xylanase is selected from the group consisting of *Trichoderma reesei* xylanase I, *Trichoderma reesei* xylanase II, *Trichoderma harzianum* xylanase, *Trichoderma viride* xylanase, *Bacillus circulans* xylanase A, *Bacillus subtilis* xylanase A, *Aspergillus niger* xylanase A, *Aspergillus kawachii* xylanase C, *Aspergillus tubigensis* xylanase A, *Streptomyces lividans* xylanase B, and *Streptomyces lividans* xylanase C, for approximately 5 minutes to three hours, at a temperature between approximately 55° C. to 75° C.

8. The method of claim 7 wherein the xylanase treatment is carried out at pH 7.5 to 9.0.

* * * * *